US007700827B2

(12) United States Patent
Meagher et al.

(10) Patent No.: US 7,700,827 B2
(45) Date of Patent: Apr. 20, 2010

(54) METAL RESISTANT PLANTS AND PHYTOREMEDIATION OF ENVIRONMENTAL CONTAMINATION

(75) Inventors: Richard B. Meagher, Athens, GA (US); Yujing Li, Athens, GA (US); Om P. Dhankher, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 1032 days.

(21) Appl. No.: 10/450,731

(22) PCT Filed: Dec. 13, 2001

(86) PCT No.: PCT/US01/48105

§ 371 (c)(1),
(2), (4) Date: Dec. 4, 2003

(87) PCT Pub. No.: WO02/48335

PCT Pub. Date: Jun. 20, 2002

(65) Prior Publication Data

US 2005/0198707 A1    Sep. 8, 2005

Related U.S. Application Data

(60) Provisional application No. 60/255,001, filed on Dec. 13, 2000, provisional application No. 60/300,525, filed on Jun. 22, 2001.

(51) Int. Cl.
*A01H 5/00* (2006.01)
*C12N 15/09* (2006.01)
*C12N 15/82* (2006.01)
*C12N 15/31* (2006.01)

(52) U.S. Cl. .................. 800/278; 800/288; 800/317; 800/320; 800/298; 435/430.1; 435/468

(58) Field of Classification Search ............... 536/23.7, 536/23.6; 435/69.1; 800/278, 298, 320.1, 800/317

See application file for complete search history.

(56) References Cited

U.S. PATENT DOCUMENTS

| 4,728,427 | A | 3/1988 | Revis et al. ............... 210/611 |
| 5,320,663 | A | 6/1994 | Cunningham .............. 75/432 |
| 5,393,426 | A | 2/1995 | Raskin et al. .............. 210/602 |
| 5,668,294 | A | 9/1997 | Meagher et al. ............ 800/205 |
| 5,728,300 | A | 3/1998 | Kapulnik et al. ........... 210/602 |
| 5,741,427 | A | 4/1998 | Watts et al. ................. 210/747 |
| 5,853,576 | A | 12/1998 | Kapulnik et al. ........... 210/150 |
| 5,874,242 | A | 2/1999 | Mensa-Wilmot ........... 435/69.1 |
| 5,965,792 | A | 10/1999 | Schroeder et al. .......... 800/278 |
| 5,965,796 | A | 10/1999 | Meagher et al. ............ 800/278 |
| 6,576,816 | B2 | 6/2003 | Terry et al. ................. 800/306 |
| 6,750,042 | B2 * | 6/2004 | Summers et al. ............ 435/69.1 |
| 2002/0016983 | A1 | 2/2002 | Terry et al. ................. 800/306 |

FOREIGN PATENT DOCUMENTS

| WO | WO 94/29226 | 12/1994 |
| WO | WO 98/04700 | 2/1998 |
| WO | WO 00/71695 A1 | 11/2000 |
| WO | WO 02/33105 A3 | 4/2002 |

OTHER PUBLICATIONS

Chen et al. J. Biological Chemistry, vol. 261 (32), pp. 15030-15038 (1986).*
Salt et al. Biotechnology, vol. 13, pp. 468-474, 1995(.*
Peter Goldbrough . Ann Arbor Press, pp. 221-228, 1999).*
Guerinot et al. Plant Physiology (2001), vol. 125, pp. 164-167.*
An, Y-Q et al. (1996) "Strong, constitutive expression of the *Arabidopsis* ACT2/ACT8 actin subclass in vegetative tissues" *Plant J.* 10:107-121.
Baker, AJM (2000) "Metal Hyperaccumulator Plants: A review of the Ecology and Physiology of a Biological Resource for Phytoremediation of Metal-Polluted Soils"; *Phytoremediation of contaminated soil and water* (Terry, N. and Baneulos, G.S., eds.). Boca Raton FL. CRC Press LLC. p. 85-107.
Baker, AJM et al. (1989) "Terrestrial Higher Plants which Hyperaccumulate Metallic Elements—A Review of their Distribution, Ecology and Phytochemistry"; *Biorecovery* 1:81-126.
Bariola, PA et al. (Jan. 1999) "Regulation of S-Like Ribonuclease Levels in Arabidopsis Antisense Inhibition of *RNS1* or *RNS2* Elevates Anthocyanin Accumulation"; *Plant Physiol.* 119:331-342.
Bent, AF et al. (1994) "*RTPS2* of *Arabidopsis thaliana* ; A Leucine-Rich Repeat Class of Plant Disease Resistance Genes"; *Science* 265:1856-1860.
Bhattacharjee, H et al. (1996) Spatial Proximity of $Cys^{113}$, $Cys^{172}$, and $Cys^{422}$ in the Metalloactivation Domain of the ArsA ATPase; *J. Biol. Chem.* 271:(40):24465-24470.
Bizily, SP et al. (Jun. 1999) "Phytoremediation of methylmercury pollution: *merB* expression in *Arabidopsis thaliana* confers resistance to organomercurials"; *Proc. Natl. Acad. Sci. USA* 96:6808-6813.
Bizily, SP et al. (Feb. 2000) "Phytodetoxification of hazardous organomercurials by genetically engineered plants"; *Nat. Biotech.* 18(2):213-217.
Brown, SL et al. (1995) "Zinc and Cadmium Uptake by Hyperaccumulator *Thlaspi caerulescens* and Metal Tolerant *Silene vulgaris* Grown on Sludge-Amended Soils"; *Environ. Sci. Technol.* 29:1581-1585.

(Continued)

*Primary Examiner*—Medina A Ibrahim
(74) *Attorney, Agent, or Firm*—Greenlee, Winner and Sullivan, P.C.

(57) ABSTRACT

The present disclosure provides a method of producing transgenic plants which are resistant to at least one metal ion by transforming the plant with a recombinant DNA comprising a nucleic acid encoding a bacterial arsenic reductase under the control of a plant expressible promoter, and a nucleic acid encoding a nucleotide sequence encoding a phytochelatin biosynthetic enzyme under the control of a plant expressible promoter. The invention also relates a method of phytoremediation of a contaminated site by growing in the site a transgenic plant expressing a nucleic acid encoding a bacterial arsenate reductase and a nucleic acid encoding a phytochelatin biosynthetic enzyme.

16 Claims, 26 Drawing Sheets

OTHER PUBLICATIONS

Brown, SL et al. (1995) Zinc and Cadmium Uptake by Hyperaccumulator *Thalspi caerulescens* Grown in Nutrient Solution; *Soil Science Society Am. J.* 59:125-133.

Butcher, BG et al. (May 2000) "The chromosomal arsenic resistance genes of *Thiobacillus ferrooxidans* have an unusual arrangement and confer increased arsenic and antimony resistance to *Escherichia coli*"; *App. Env. Microbiol.* 66(5):1826-1833.

Carey, J. "Can Flowers Cleanse the Earth?"; *Business Week* Feb.19, 1996, p. 54.

Carlin, A et al. (1995) "The *ars* Operon of *Escherichia coli* Confers Arsenical and Antimonial Resistance"; *J. Bacteriol.* 177(4):981-986.

Castresana, C et al. (1988) "Both positive and negative regulatory elements mediate expression of a photoregulated CAB gene from *Nicotiana plumbaginifolia* "; *EMBO J.* 7:1929-1936.

Chen, CM et al. (1994) Plasmid R773 arsenical resistance operon genes, arsA, arsB and arsC, complete cds., NCBI Accession No. J02591.

Chen, C-M et al. (1986) "Nucleotide Sequence of the Structural Genes for an Anion Pump"; *J. Biol. Chem.* 261:15030-15038.

Clemens, S et al. (Jun. 1999) "Tolerance to toxic metals by a gene family of phytochelatin synthases from plants and yeast"; *The EMBO J.* 18(12):3325-3333.

Cobbett, CS (1998) "The glutathione-deficient, cadmium-sensitive mutant, *cad2-1*, of *Arabidopsis thaliana* is deficient in γ-glutamylcysteine synthetase"; *Plant J.* 16(1):73-78.

Cobbett, CS (Jul. 2000) "Phytochelatins and Their Roles in Heavy Metal Detoxification"; *Plant Physiol.* 123:825-832.

Cohill, PR et al. (2001) "Transgenic *Chlorella* as a Phytoremedial Bioreactor"; *FASEB J.* 15(5):A877. (Abstract only.).

Condit, CM et al. (1990) "Characterization of the Expression of the Petunia Glycine-Rich Protein-1 Gene Product"; *Plant Physiol.* 93:596-602.

Cruz, LJ et al. (May 2000) "Immunogenicity Comparison of a Multi-antigenic Peptide Bearing V3 Sequences of the Human Immunodeficiency Virus Type 1 with TAB9 Protein in Mice"; *J. Pept. Sci.* 65:217-224.

Dey, S et al. (1994) "High level arsenite resistance in *Leishmania tarentolae* is mediated by an active extrusion system"; *Mol. Biochem. Parasitology* 67:49-57.

Dhanker, OP et al. (Spring 2002) "Resistance and accumulation of arsenic by plants expressing bacterial arsenate reductase and γ-glutamylcysteine synthatase"; In vitro *Cellular & Dev. Biology Animal* 38:67. (Abstract only.).

Dhanker, OP et al. (Nov.2002) "Engineering tolerance and hyperaccumulation of arsenic in plants by combining arsenate reductase and gammaglutamylcysteine synthetase expression"; *Nat. Biotech.* 20(11): 1140-1145.

Ebbs et al. (1997) "Heavy Metals in the Environment"; *J. Environ. Quality* 26:1424-1430.

Gladysheva, TB et al. (1994) "Properties of the Arsenate Reductase of Plasmid R773"; *Biochemistry* 33:7288-7293.

Goldsbrough, P (2000) "Metal Tolerance in Plants. The Role of Phytochelatins and Metallothioneins"; *Phytoremediation of Contaminated Soil and Water*, (Terry, N. and Banuelos, G., eds.). CRC Press, Boca Raton, FL. pp. 221-233.

Grec, S et al. (Jan. 2000) "Cryptic polyadenylation sites within the coding sequence of three yeast genes expressed in tobacco"; *Gene* 242:87-95.

Ha, S-B et a. (Jun. 1999) "Phytochelatin Synthase Genes from Arabidopsis and the Yeast *Schizosaccharomyces pombe* "; *Plant Cell* 11:1153-1163.

Heidecker, G et al. (1986) "Structural Analysis of Plant Genes"; *Ann Rev. Plant Physiol.* 37:439-466.

Kandasamy, MK et al. (Oct. 1999) "Actin-Organelle Interaction: Association With Chloroplast in Arabidopsis Leaf Mesophyll Cells"; *Cell Motility Cytoskeleton* 44:110-118.

Kovari, IA et al. (1997) "Expression of tomato gamma-Glu-Cys synthetase in the Arabidopsis cad2 mutant restores cadmium tolerance"; *American Society of Plant Biologists (ASPB)* Abstract No. 574; from internet.

Li, Y et al. (Nov. 2001) "Rapid Isolation of Monoclonal Antibodies. Monitoring Enzymes in the Phytochelatin Synthesis Pathway"; *Plant Physiol.* 127:711-719.

Li, Y et al. (Jun. 2001) "Overexpression of enzymes involved in the biosynthesis of phytochelatin in *Arabidopsis thaliana* enhances arsenate and mercury resistance"; $12^{th}$ *Int. Conference on Arabidopsis Research.* U. Wisconsin. (Abstract Preview).

Liu, J et al. (1995) "Identification of an essential Cysteinyl Residue in the ArsC Arsenate Reductase of Plasmid R773"; *Biochemistry* 34:13472-13476.

McGrath, JM et al. (1992) "Sequence of the fourth and fifth Photosystem II Type I chlorophyll *a/b*-binding protein genes of *Arabidopsis thaliana* and evidence for the presence of a full complement of the extended CAB gene family"; *Plant Mol. Biol.* 19:725-733.

McGrath, SP et al. (1993) "The Potential for the use of Metal-accumulating Plants for the in situ Decontamination of Metal-polluted Soils"; Integrated *Soil and Sediment Research: a basis for proper prediction*, Eijsackers, H.J.P. and Hamers, T., (eds.). Dordrecht, The Netherlands: Kluwer Academic Publishers, pp. 673-676.

McLean, BG et al. (1990) "Tissue-Specific Expression of Divergent Actins in Soybean Root"; *Plant Cell* 2:335-344.

Meagher, R.B. (Apr.2000) "Phytoremediation of toxic elemental and organic pollutants"; *Curr. Opin. Plant Biol.* 3:153-162.

Meagher, RB et al. (Dec. 2001) "Pink water, green plants, and pink elephants"; *Nat. Biotech.*19(12):1120-1121.

Meagher, RB et al. (2000) "Engineered Phytoremediation of Mercury Pollution in Soil and Water Using Bacterial Genes"; *Phytoremediation of /Contaminated Soil and Water* 201-213.

Mobley, HLT et al. (1983) "Cloning and Expression of R-Factor Mediated Arsenate Resistance in *Escherichia coli*"; *Mol. Gen. Genet.* 191:421-426.

Oden,KL et al (1994) "Arsenate reduction mediated by the plasmid-encoded ArsC protein is coupled to glutathione"; 12(2):301-306.

Palanivelu, R et al. (May 2000) "Conserved expression of *Arabidopsis thaliana* poly (A) binding protein 2 (PAB2) in distinct vegetative and reproductive tissues"; *Plant J.* 22:199:210.

Raskin, I. (1996) "Plant genetic engineering may help with environmental cleanup"; *Proc. Natl. Acad. Sci.USA* 93:3164-3166.

Rensing, C et al. (1997) "The *zntA* gene of *Escherichia coli* encodes a Zn(II)-translocating P-type ATPase"; *Proc. Natl. Acad. Sci. USA* 94:14326-14331.

Robinson, BH et al. (1997) "The potential of the high-biomass nickel hyperaccumulator *Berkheya coddii* for phtoremediation and phytomining"; *J. Geochem. Explor.* 60:115-126.

Rosen, BP (1995) "Resistance Mechanisms to Arsenicals and Antimonials": *J. Basic & Clin. Physiol. & Pharmacology* 6(3-4):251-263.

Rosen, BP (May 1999) "Families of arsenic transporters"; *Trends Microbiol* 7:207-212.

Rosen, BP et al. (1991) "Molecular Analysis of an Anion Pump; Purification of the ArsC Protein"; *Arch Biochem. Biophys.* 284:381-385.

Rosen, BP (1996) "Bacterial resistance to heavy metals and metalloids"; *JBIC* 1:273-277.

Rosenstein, R et al. (1992) "Expression and Regulation of the Antimonite, Arsenite, and Arsenate Resistance Operon of *Staphylococcus xylosus* Plasmid pSX267"; *J. Bacteriol.* 174(11):3676-3683.

Rugh, CL et al. (1998) "Development of transgenic yellow poplar for mercury phytoremediation"; *Nature Biotechnol.* 16:925-928.

Rugh, CL et al. (1996) "Mercuric ion reduction and resistance in transgenic *Arabidopsis thaliana* plants expressing a modified bacterial *merA* gene"; *Proc. Natl. Acad. Sci. USA* 93:3182-3187.

Salt, DE et al. (1995) "Phytoremediation: A Novel Strategy for the Removal of Toxic Metals from the Environment Using Plants"; *Biotechnology* 13:468-474.

Shi, W et al. (1994) "Identification of a Putative Metal Binding Site in a New Family of Metalloregulatory Proteins"; *J. Biol. Chem.* 269:19826-19829.

Shirley, BW et al. (1987) "5' proximal sequences of a soybean ribulose-1,5-bisphosphate carboxylase small subunit gene direct light and phytochrome controlled transcription"; *Nuc. Acids Res.* 15:6501-6514.

Shirley, BW et al. (1992) Soybean SRS1 mRNA for ribulose-1,5-bisphosphate carboxylase (Rubisco) small subunit, partial cds, *Glycine max*, NCBI Accession No. X58684.

Shirley et al. (1991) "Comparison of the expression of two highly homologous members of the soybean ribulose-1,5-bisphosphate carboxylase small subunit gene family"; *Plant Mol. Biol.* 14:909-925.

Silver, S et al. (1996) "Bacterial Heavy Metal Resistance: New Surprises"; *Ann. Rev. Microbiol.* 50:753-789.

Tainer, JA et al. (1984) "The reactivity of anti-peptide antibodies is a function of the atomic mobility of sites in a protein"; *Nature* 312:127-134.

Tam and Lu (1989) "Vaccine engineering. Enhancement of immunogenicity of synthetic peptide vaccines related to hepatitis in chemically defined models consisting of T- and B-cell eptopes"; *Proc. Natl. Acad. Sci. USA* 86:9084-9088.

Tsai, M-L et al. (1997) "Efflux Mechanisms of Resistance to Cadmium, Arsenic and Antimony in Prokaryotes and Eukaryotes"; *Zoological Studies* 36:1-16.

Vatamaniuk, OK et al. (Jun. 1999) "AtPCS1, a phytochelatin synthase from Arabidopsis: Isolation and in vitro reconstitution"; *Proc. Natl. Acad. Sci. USA* 96:7110-7115.

Vatamaniuk, OK et al. (Oct. 2000) "Mechanism of *Heavy Metal Ion Activation of Phytochelatin (PC) Synthase*"; *J. Biol. Chem.* 275(40):31451-31459.

Watanabe, K et al. (Feb. 1999) *E. coli* B gshI gene for γ-glutamykysteine synthetase, NCBI Accession No. X03954.

Wood, V et al. (Jun. 2003) *S. pombe* chromosome I cosmid c3H1, NCBI Accession No. Z68144.

Wu, J et al. (1993) "Metalloregulated Expression of the *ars* Operon"; *J. Biol. Chem.* 268:52-58.

Xu, C et al. (1998) "Metalloid Resistance Mechanisms in Prokaryotes"; *J. Biochem.* 123:16-23.

Zhu, YL et al. (Dec. 1999) "Cadmium Tolerance and Accumulation in Indian Mustard is Enhanced by Overexpressing γ-Glutamylcysteine Synthetase"; *Plant Physiol.* 121:1169-1177.

Zhu, YL et al (Jan. 1999) "Overexpression of Glutathione Synthetase in Indian Mustard Enhances Cadmium Accumulation and Tolerance"; *Plant Physiol.* 119:73-79.

\* cited by examiner

FIG. 6A
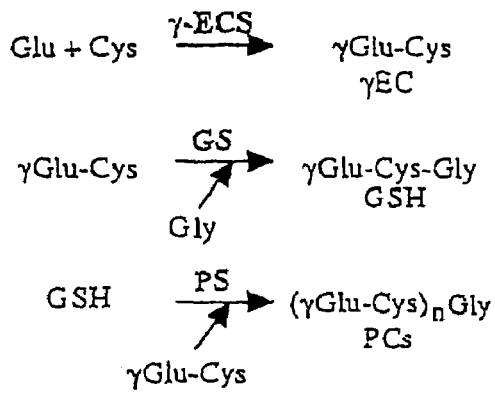
FIG. 6B
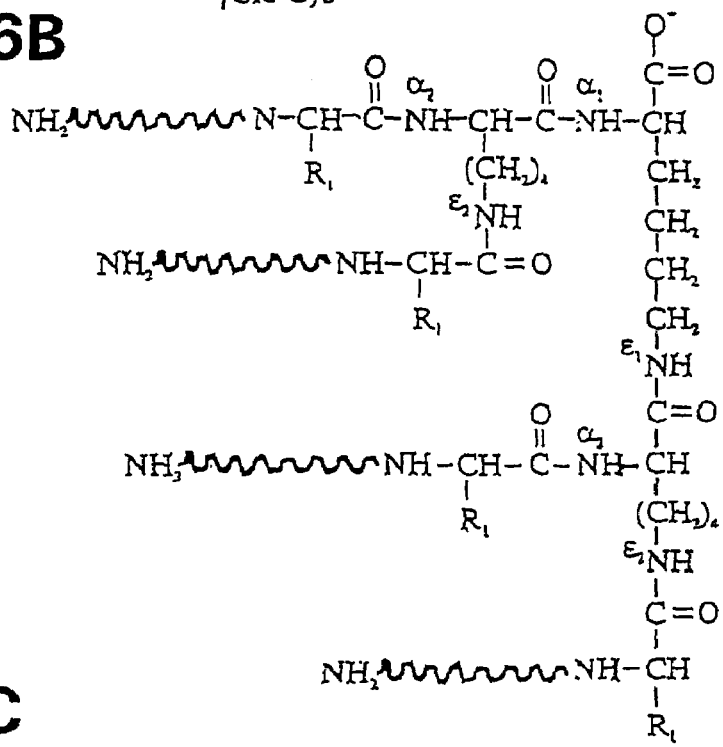
FIG. 6C
ECS-NMAP
2                                  31
IPDVSQALAW LEKHPQALKG IQRGLERETL
GS-NMAP
2                                  31
IKLGIVMDPI ANINIKKDSS FAMLLEAQRR
PS-NMAP
2                                  30
NIVKRAVPEL LRGMTNATPN IGLIKNKVY FIG. 7A
FIG. 7B
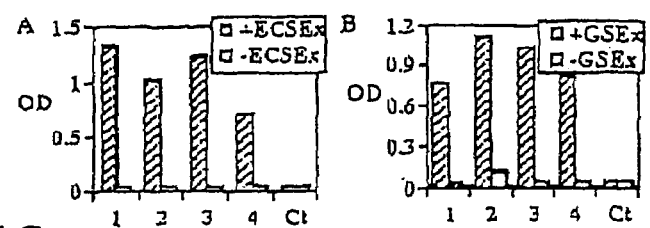
FIG. 7C
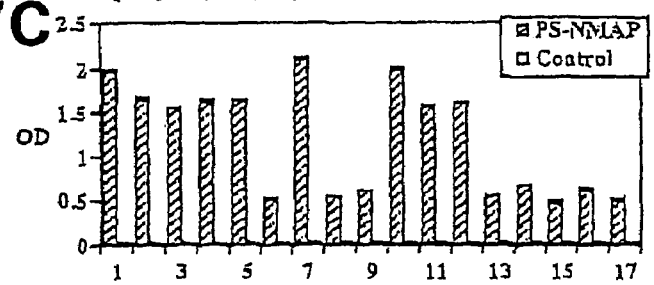
FIG. 7D
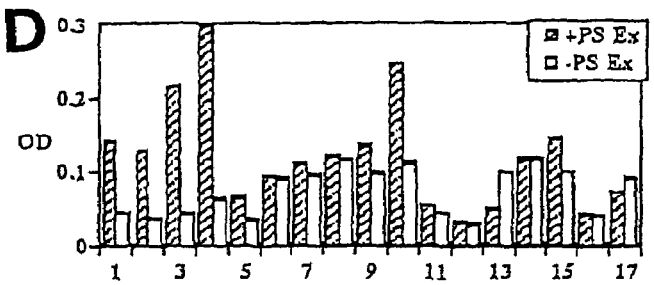

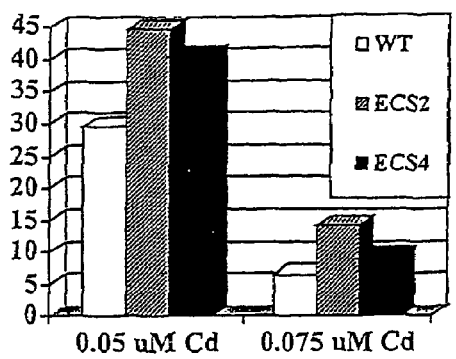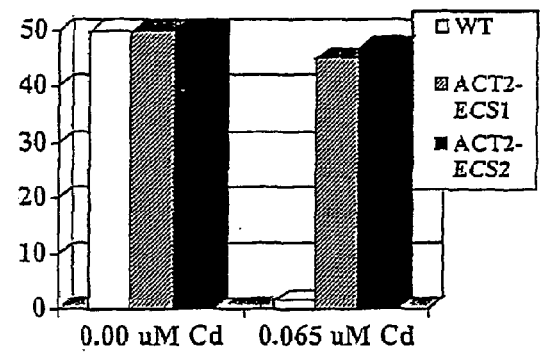
FIG. 10A  FIG. 10B

```
   1 GCGCCCAATA CGCAAACCGC CTCTCCCCGC GCGTTGGCCG ATTCATTAAT
  51 GCAGCTGGCA CGACAGGTTT CCCGACTGGA AAGCGGGCAG TGAGCGCAAC
 101 GCAATTAATG TGAGTTAGCT CACTCATTAG GCACCCCAGG CTTTACACTT
 151 TATGCTTCCG GCTCGTATGT TGTGTGGAAT TGTGAGCGGA TAACAATTTC
 201 ACACAGGAAA CAGCTATGAC CATGATTACG CCAAGCTTGC ATGCCTGCAG
 251 GTCGAC
            >SeqEd (include) of: act2-allg. Check: 2510
            from: 1 to: 1377>
            ATTA TGATCTCAAA TACATTGATA CATATCTCAT CTAGATCTAG
 301 GTTATCATTA TGTAAGAAAG TTTTGACGAA TATGNNACGA CAAAATGGCT
 351 AGACTCGATG TAATTGGTAT CTCAACTCAA CATTATACTT ATACCAAACA
 401 TTAGTTAGCA AAATTTAAAC AACTATTTTT ATGTATGCAA GAGTCAGCAT
 451 ATGTATAATT GATTCAGAAT CGTTTTGACG AGTTCGGATG TAGTAGTAGC
 501 CATTATTTAA TGTACATACT AATCGTGAAT AGTGATATGA TGAAACATTG
 551 TATCTTATTG TATAAATATC CATAAACACA TCATGAAAGA CACTTTCTTT
 601 CACGGTCTGA ATTAATTATG ATACAATTCTAATAGAAAAC GAATTAAATT
 651 ACGTTGAATT GTATGAAATC TAATTGAACA AGCCAACCACGACGACGACT
 701 AACGTTGCCT GGATTGACTC GGTTTAAGTT AACCACTAAA AAAACGGAGC
 751 TGTCATGTAA CACGCGGATC GAGCAGGTCA CAGTCATGAA GCCATCAAAG
 801 CAAAAGAACT AATCCAAGGG CTGAGATGAT TAATTAGTTT AAAAATTAGT
 851 TAACACGAGG GAAAAGGCTG TCTGACAGCC AGGTCACGTT ATCTTACCT
 901 GTGGTCGAAA TGATTCGTGT CTGTCGATTT TAATTATTTT TTTGAAAGGC
 951 CGAAAATAAA GTTGTAAGAG ATAAACCCGC CTATATAAAT TCATATATTT
                                          Tc+1
1001 TCCTCTCCGC TTTGAATTGT CTCGTTGTCC TCCTCACTTT CATCAGCCGT
1051 TTTGAATCTC CGGCGACTTG ACAGAGAAGA ACAAGGAAGA AGACTAAGAG
1101 AGAAAGTAAG AGATAATCCA GGAGATTCAT TCTCCGTTTT GAATCTTCCT
                                                 intron 0
1151 CAATCTCATC TTCTTCCGCT CTTTCTTTCC AAGGTAATAG GAACTTTCTG
1201 GATCTACTTT ATTTGCTGGA TCTCGATCTT GTTTTCTCAA TTTCCTTGAG
1251 ATCTGGAATT CGTTTAATTT GGATCTGTGA ACCTCCACTA AATCTTTTGG
1301 TTTTACTAGA ATCCATCTAA GTTGACCGAT CAGTTAGCTC CATTATAGCT
```

FIG. 12B1

```
1351 ACCAGAATTT GGCTTGACCT TGATGGAGAG ATCCATGTTC ATGTTACCTG

1401 GGAAATGATT TGTATATGTG AATTGAAATC TGAACTGTTG AAGTTAGATT

1451 GAATCTGAAC ACTGTCAATG TTAGATTGAA TCTGAACACT GTTTAAGTTA

1501 GATGAAGTTT GTGTATAGAT TCTTCGAAAC TTAGGATTT GTAGTGTCGT

1551 ACGTTGAACA GAAAGCTATT TCTGATTCAA TCAGGGTTTA TTTGACTGTA
                                            ┐ exon 1
1601 TTGAACTCTT TTTGTGTGTT TGCAG CTCAT AAA
                                        ┘        <SeqEd (include)
                     of: act2-allg. check: 2510 from: 1 to: 1377<
                                               GGATCC   BamHI
                                                    <51 base
         pair polylinker inlcuding SmaI, XboI, HindIII, NotI,
         NcoI added during pcr of act2-3' and <
                                                 C GGGCTCGAGA)multi-
1651 AGCTTGCGGC CGCCATGG                                   )linker
                      >SeqEd (include) of: act2-allg.
                   check: 2510 from: 2675 to: 3123>
                                TA A GCTCTCAAG ATCAAAGGCT TAAAAAGCTG
                                ↳ Actin2 stop codon.
1701 GGGTTTTATG AATGGGATCA AAGTTTCTTT TTTTCTTTTA TATTTGCTTC   Actin2-
                                                             3' end.
1751 TCCATTTGTT TGTTTCATTT CCCTTTTTGT TTTCGTTTCT ATGATGCACT

1801 TGTGTGTGAC AAACTCTCTG GGTTTTTACT TACGTCTGCG TTTCAAAAAA

1851 AAAAACCGCT TTCGTTTTGC GTTTTAGTCC CATTGTTTTG TAGCTCTGAG

1901 TGATCGAATT GATGCCTCTT TATTCCTTTT GTTCCCTATA ATTTCTTTCA

1951 AAACTCAGAA RAAAAACCTT GAAACTCTTT GCAATGTTAA TATAAGTATT

2001 GTATAAGATT TTTATTGATT TGGTTATTAG TCTTACTTTT GCTACCTCCA

2051 TCTTCACTTG GAACTGATAT TCTGAATAGT TAAAGCGTTA CATGTCTTCC

2101 ATTCACAAAT GAACTTA
                      <SeqEd (include) of: act2-allg.
                    check: 2510 from: 2675 to: 3123<
                    <SacI/EcoRI sites incorporated
              during PCR of Act2-3' end< ↓
                                GAG CTCGAATTC A CTGGCCGTCG TTTTACAACG

2151 TCGTGACTGG GAAAACCCTG GCGTTACCCA ACTTAATCGC CTTGCAGCAC

2201 ATCCCCCTTT CGCCAGCTGG CGTAATAGCG AAGAGGCCCG CACCGATCGC
                                                              ┐ puc19
2251 CCTTCCCAAC AGTTGCGCAG CCTGAATGGC GAATGGCGCC TGATGCGGTA  │

2301 TTTTCTCCTT ACGCATCTGT GCGGTATTTC ACACCGCATA TGGTGCACTC ↓

2351 TCAGTACAAT CTGCTCTGAT GCCGCATAGT TAAGCCAGCC CCGACACCCG

2401 CCAACACCCG CTGACGCGCC CTGACGGGCT TGTCTGCTCC CGGCATCCGC

2451 TTACAGACAA GCTGTGACCG TCTCCGGGAG CTGCATGTGT CAGAGGTTTT

2501 CACCGTCATC ACCGAAACGC GCGAGACGAA AGGGCCTCGT GATACGCCTA
```

FIG. 12B2

```
2551 TTTTTATAGG TTAATGTCAT GATAATAATG GTTTCTTAGA CGTCAGGTGG
2601 CACTTTTCGG GGAAATGTGC GCGGAACCCC TATTTGTTTA TTTTTCTAAA
2651 TACATTCAAA TATGTATCCG CTCATGAGAC AATAACCCTG ATAAATGCTT
2701 CAATAATATT GAAAAAGGAA GAGTATGAGT ATTCAACATT TCCGTGTCGC
2751 CCTTATTCCC TTTTTTGCGG CATTTTGCCT TCCTGTTTTT GCTCACCCAG
2801 AAACGCTGGT GAAAGTAAAA GATGCTGAAG ATCAGTTGGG TGCACGAGTG
2851 GGTTACATCG AACTGGATCT CAACAGCGGT AAGATCCTTG AGAGTTTTCG
2901 CCCCGAAGAA CGTTTTCCAA TGATGAGCAC TTTTAAAGTT CTGCTATGTG
2951 GCGCGGTATT ATCCCGTATT GACGCCGGGC AAGAGCAACT CGGTCGCCGC
3001 ATACACTATT CTCAGAATGA CTTGGTTGAG TACTCACCAG TCACAGAAAA
3051 GCATCTTACG GATGGCATGA CAGTAAGAGA ATTATGCAGT GCTGCCATAA
3101 CCATGAGTGA TAACACTGCG GCCAACTTAC TTCTGACAAC GATCGGAGGA
3151 CCGAAGGAGC TAACCGCTTT TTTGCACAAC ATGGGGGATC ATGTAACTCG
3201 CCTTGATCGT TGGGAACCGG AGCTGAATGA AGCCATACCA AACGACGAGC
3251 GTGACACCAC GATGCCTGTA GCAATGGCAA CAACGTTGCG CAAACTATTA
3301 ACTGGCGAAC TACTTACTCT AGCTTCCCGG CAACAATTAA TAGACTGGAT
3351 GGAGGCGGAT AAAGTTGCAG GACCACTTCT GCGCTCGGCC CTTCCGGCTG
3401 GCTGGTTTAT TGCTGATAAA TCTGGAGCCG GTGAGCGTGG GTCTCGCGGT
3451 ATCATTGCAG CACTGGGGCC AGATGGTAAG CCCTCCCGTA TCGTAGTTAT
3501 CTACACGACG GGGAGTCAGG CAACTATGGA TGAACGAAAT AGACAGATCG
3551 CTGAGATAGG TGCCTCACTG ATTAAGCATT GGTAACTGTC AGACCAAGTT
3601 TACTCATATA TACTTTAGAT TGATTTAAAA CTTCATTTTT AATTTAAAAG
3651 GATCTAGGTG AAGATCCTTT TTGATAATCT CATGACCAAA ATCCCTTAAC
3701 GTGAGTTTTC GTTCCACTGA GCGTCAGACC CCGTAGAAAA GATCAAAGGA
3751 TCTTCTTGAG ATCCTTTTTT TCTGCGCGTA ATCTGCTGCT TGCAAACAAA
3801 AAAACCACCG CTACCAGCGG TGGTTTGTTT GCCGGATCAA GAGCTACCAA
3851 CTCTTTTTCC GAAGGTAACT GGCTTCAGCA GAGCGCAGAT ACCAAATACT
3901 GTCCTTCTAG TGTAGCCGTA GTTAGGCCAC CACTTCAAGA ACTCTGTAGC
3951 ACCGCCTACA TACCTCGCTC TGCTAATCCT GTTACCAGTG GCTGCTGCCA
4001 GTGGCGATAA GTCGTGTCTT ACCGGGTTGG ACTCAAGACG ATAGTTACCG
4051 GATAAGGCGC AGCGGTCGGG CTGAACGGGG GGTTCGTGCA CACAGCCCAG
```

FIG. 12B3

```
4101  CTTGGAGCGA  ACGACCTACA  CCGAACTGAG  ATACCTACAG  CGTGAGCTAT
4151  GAGAAAGCGC  CACGCTTCCC  GAAGGGAGAA  AGGCGGACAG  GTATCCGGTA
4201  AGCGGCAGGG  TCGGAACAGG  AGAGCGCACG  AGGGAGCTTC  CAGGGGGAAA
4251  CGCCTGGTAT  CTTTATAGTC  CTGTCGGGTT  TCGCCACCTC  TGACTTGAGC
4301  GTCGATTTTT  GTGATGCTCG  TCAGGGGGGC  GGAGCCTATG  GAAAAACGCC
4351  AGCAACGCGG  CCTTTTTACG  GTTCCTGGCC  TTTTGCTGGC  CTTTTGCTCA
4401  CATGTTCTTT  CCTGCGTTAT  CCCCTGATTC  TGTGGATAAC  CGTATTACCG
4451  CCTTTGAGTG  AGCTGATACC  GCTCGCCGCA  GCCGAACGAC  CGAGCGCAGC
4501  GAGTCAGTGA  GCGAGGAAGC  GGAAGA
```

```
   1  GCGCCCAATA CGCAAACCGC CTCTCCCCGC GCGTTGGCCG ATTCATTAAT
  51  GCAGCTGGCA CGACAGGTTT CCCGACTGGA AAGCGGGCAG TGAGCGCAAC
 101  GCAATTAATG TGAGTTAGCT CACTCATTAG GCACCCCAGG CTTTACACTT
 151  TATGCTTCCG GCTCGTATGT TGTGTGGAAT TGTGAGCGGA TAACAATTTC
 201  ACACAGGAAA CAGCTATGAC CATGATTACG CCAAGCTTGC ATGCCTGCAG
 251  GTCGAC
          >SeqEd (include) of: act2-allg. check: 2510
          from: 1 to: 1377>
           ATTA TGATCTCAAA TACATTGATA CATATCTCAT CTAGATCTAG    Actin2-5'
 301  GTTATCATTA TGTAAGAAAG TTTTGACGAA TATGNNACGA CAAAATGGCT
 351  AGACTCGATG TAATTGGTAT CTCAACTCAA CATTATACTT ATACCAAACA
 401  TTAGTTAGCA AAATTTAAAC AACTATTTTT ATGTATGCAA GAGTCAGCAT
 451  ATGTATAATT GATTCAGAAT CGTTTTGACG AGTTCGGATG TAGTAGTAGC
 501  CATTATTTAA TGTACATACT AATCGTGAAT AGTGATATGA TGAAACATTG
 551  TATCTTATTG TATAAATATC CATAAACACA TCATGAAAGA CACTTTCTTT
 601  CACGGTCTGA ATTAATTATG ATACAATTCT AATAGAAAAC GAATTAAATT
 651  ACGTTGAATT GTATGAAATC TAATTGAACA AGCCAACCAC GACGACGACT
 701  AACGTTGCCT GGATTGACTC GGTTTAAGTT AACCACTAAA AAAACGGAGC
 751  TGTCATGTAA CACGCGGATC GAGCAGGTCA CAGTCATGAA GCCATCAAAG
 801  CAAAAGAACT AATCCAAGGG CTGAGATGAT TAATTAGTTT AAAAATTAGT
 851  TAACACGAGG GAAAAGGCTG TCTGACAGCC AGGTCACGTT ATCTTTACCT
 901  GTGGTCGAAA TGATTCGTGT CTGTCGATTT TAATTATTTT TTTGAAAGGC
 951  CGAAAATAAA GTTGTAAGAG ATAAACCCGC CTATATAAAT TCATATATTT
                                         pTch1
1001  TCCTCTCCGC TTTGAATTGT CTCGTTGTCC TCCTCACTTT CATCAGCCGT
1051  TTTGAATCTC CGGCGACTTG ACAGAGAAGA ACAAGGAAGA AGACTAAGAG
1101  AGAAAGTAAG AGATAATCCA GGAGATTCAT TCTCCGTTTT GAATCTTCCT
                        exon0                intron0
1151  CAATCTCATC TTCTTCCGCT CTTTCTTTCC AAGGTAATAG GAACTTTCTG
1201  GATCTACTTT ATTTGCTGGA TCTCGATCTT GTTTTCTCAA TTTCCTTGAG
```

FIG. 13B2

```
1251  ATCTGGAATT CGTTTAATTT GGATCTGTGA ACCTCCACTA AATCTTTTGG
1301  TTTTACTAGA ATCGATCTAA GTTGACCGAT CAGTTAGCTC GATTATAGCT
1351  ACCAGAATTT GGCTTGACCT TGATGGAGAG ATCCATGTTC ATGTTACCTG
1401  GGAAATGATT TGTATATGTG AATTGAAATC TGAACTGTTG AAGTTAGATT
1451  GAATCTGAAC ACTGTCAATG TTAGATTGAA TCTGAACACT GTTTAAGTTA
1501  GATGAAGTTT GTGTATAGAT TCTTCGAAAC TTTAGGATTT GTAGTGTCGT
1551  ACGTTGAACA GAAAGCTATT TCTGATTCAA TCAGGGTTTA TTTGACTGTA
1601  TTGAACTCTT TTTGTGTGTT TGCAG TCAT AAA
```
                                    ↳ Xhon 0
                                    <SeqEd (include)
of: act2-allg. check: 2510 from: 1 to: 1377<
                                    GGATCC ← BamHI
                                    <51 base
pair polylinker including SmaI, XhoI, HindIII, NotI,
NcoI added during pcr of act2-3' and <
                                    >SeqEd
(include) of: pbi1012.seq  check: 5349 from: 2528
to: 4421>
            ⟋ ATG GuS.              C CGGGTAGGTC  ⟍
```
1651  AGTCCCTT AT G TTACGTCCT GTAGAAACCC CAACCCGTGA ATCAAAAAA    ↓ GuS
1701  CTCGACGGCC TGTGGGCATT CAGTCTGGAT CGCGAAAACT GTGGAATTGA
1751  TCAGCGTTGG TGGGAAAGCG CGTTACAAGA AAGCCGGGCA ATTGCTGTGC
1801  CAGGCAGTTT TAACGATCAG TTCGCCGATG CAGATATTCG TAATTATGCG
1851  GGCAACGTCT GGTATCAGCG CGAAGTCTTT ATACCGAAAG GTTGGGCAGG
1901  CCAGCGTATC GTGCTGCGTT TCGATGCGGT CACTCATTAC GGCAAAGTGT
1951  GGGTCAATAA TCAGGAAGTG ATGGAGCATC AGGGCGGCTA TACGCCATTT
2001  GAAGCCGATG TCACGCCGTA TGTTATTGCC GGGAAAAGTG TACGTATCAC
2051  CGTTTGTGTG AACAACGAAC TGAACTGGCA GACTATCCCG CCGGGAATGG
2101  TGATTACCGA CGAAAACGGC AAGAAAAAGC AGTCTTACTT CCATGATTTC
2151  TTTAACTATG CCGGAATCCA TCGCAGCGTA ATGCTCTACA CCACGCCGAA
2201  CACCTGGGTG GACGATATCA CCGTGGTGAC GCATGTCGCG CAAGACTGTA
2251  ACCACGCGTC TGTTGACTGG CAGGTGGTGG CCAATGGTGA TGTCAGCGTT
2301  GAACTGCGTG ATGCGGATCA ACAGGTGGTT GCAACTGGAC AAGGCACTAG
2351  CGGGACTTTG CAAGTGGTGA ATCCGCACCT CTGGCAACCG GGTGAAGGTT
2401  ATCTCTATGA ACTGTGCGTC ACAGCCAAAA GCCAGACAGA GTGTGATATC
2451  TACCCGCTTC GCGTCGGCAT CCGGTCAGTG GCAGTGAAGG CCAACAGTT
2501  CCTGATTAAC CACAAACCGT TCTACTTTAC TGGCTTTGGT CGTCATGAAG
2551  ATGCGGACTT ACGTGGCAAA GGATTCGATA ACGTGCTGAT GGTGCACGAC
2601  CACGCATTAA TGGACTGGAT TGGGGCCAAC TCCTACCGTA CCTCGCATTA
2651  CCCTTACGCT GAAGAGATGC TCGACTGGGC AGATGAACAT GGCATCGTGG
```

FIG. 13B3

```
2701  TGATTGATGA AACTGCTGCT GTCGGCTTTA ACCTCTCTTT AGGCATTCGT
2751  TTCGAAGCGG GCAACAAGCC GAAAGAACTG TACAGCGAAG AGGCAGTCAA
2801  CGGGGAAACT CAGCAAGCGC ACTTACAGGC GATTAAAGAG CTGATAGCGC
2851  GTGACAAAAA CCACCCAAGC GTGGTGATGT GGAGTATTGC CAACGAACCG
2901  GATACCCGTC CGCAAGTGCA CGGGAATATT TCGCCACTGG CGGAAGCAAC
2951  GCGTAAACTC GACCCGACGC GTCCGATCAC CTGCGTCAAT GTAATGTTCT
3001  GCGACGCTCA CACCGATACC ATCAGCGATC TCTTTGATGT GCTGTGCCTG
3051  AACCGTTATT ACGGATGGTA TGTCCAAAGC GGCGATTTGG AAACGGCAGA
3101  GAAGGTACTG GAAAAGAAC TTCTGGCCTG GCAGGAGAAA CTGCATCAGC
3151  CGATTATCAT CACCGAATAC GGCGTGGATA CGTTAGCCGG GCTGCACTCA
3201  ATGTACACCG ACATGTGGAG TGAAGAGTAT CAGTGTGCAT GGCTGGATAT
3251  GTATCACCGC GTCTTTGATC GCGTCAGCGC CGTCGTCGGT GAACAGGTAT
3301  GGAATTTCGC CGATTTTGCG ACCTCGCAAG GCATATTGCG CGTTGGCGGT
3351  AACAAGAAAG GGATCTTCAC TCGCGACCGC AAACCGAAGT CGGCGGCTTT
3401  TCTGCTGCAA AAACGCTGGA CTGGCATGAA CTTCGGTGAA AAACCGCAGC
        ┌─Stop GuS
3451  AGGGAGGCAA ACAA┃TGA┃ATC AACAACTCTC CTGGCGCACC ATCGTCGGCT
3501  ACAGCCTCGG GAATTGCTAC CG
```

←disrupted NcoI site (fused bluntec SacI in GUS to blunted NcoI in pActzB)

```
                <SeqEd (include) of:
         pbil012.seq check: 5349 from: 2528 to: 4421<
                CATGG
                >SeqEd (include) of:
         act2-allg. check: 2510 from: 2675 to: 3123>
                        ┌TAA┐GCTCTCAAGA TCAAAGGCTT
                        └Stop Act 2
3551  AAAAAGCTGG GGTTTTATGA ATGGGATCAA AGTTTCTTTT TTTCTTTTAT
3601  ATTTGCTTCT CCATTTGTTT GTTTCATTTC CCTTTTTGTT TTCGTTTCTA
3651  TGATGCACTT GTGTGTGACA AACTCTCTGG GTTTTTACTT ACGTCTGCGT
3701  TTCAAAAAAA AAAaCCGCTT TCGTTTTGCG TTTTAGTCCC ATTGTTTTGT
3751  AGCTCTGAGT GATCGAATTG ATGCCTCTTT ATTCCTTTTG TTCCCTATAA
3801  TTTCTTTCAA AACTCAGAAR AAAAACCTTG ÄAACTCTTTG CAATGTTAAT
3851  ATAAGTATTG TATAAGATTT TTATTGATTT GGTTATTAGT CTTACTTTTG
3901  CTACCTCCAT CTTCACTTGG AACTGATATT CTGAATAGTT AAAGCGTTAC
```

Act 2-3' end.

```
3951  ATGTCTTCCA TTCACAAATG AACTTA
                <SeqEd (include) of:
         act2-allg. check: 2510 from: 2675 to: 3123<
                    <SacI/EcoRI sites
         incorporated during PCR of Act2-3' end<
                        GAGC TCGAATTCAC TGGCCGTCGT
4001  TTTACAACGT CGTGACTGGG AAAACCCTGG CGTTACCCAA CTTAATCGCC
4051  TTGCAGCACA TCCCCCTTTC GCCAGCTGGC GTAATAGCGA AGAGGCCCGC
4101  ACCGATCGCC CTTCCCAACA GTTGCGCAGC CTGAATGGCG AATGGCGCCT
```

FIG. 13B4

```
4151  GATGCGGTAT TTTCTCCTTA CGCATCTGTG CGGTATTTCA CACCGCATAT
4201  GGTGCACTCT CAGTACAATC TGCTCTGATG CCGCATAGTT AAGCCAGCCC
4251  CGACACCCGC CAACACCCGC TGACGCGCCC TGACGGGCTT GTCTGCTCCC
4301  GGCATCCGCT TACAGACAAG CTGTGACCGT CTCCGGGAGC TGCATGTGTC
4351  AGAGGTTTTC ACCGTCATCA CCGAAACGCG CGAGACGAAA GGGCCTCGTG
4401  ATACGCCTAT TTTTATAGGT TAATGTCATG ATAATAATGG TTTCTTAGAC
4451  GTCAGGTGGC ACTTTTCGGG GAAATGTGCG CGGAACCCCT ATTTGTTTAT
4501  TTTTCTAAAT ACATTCAAAT ATGTATCCGC TCATGAGACA ATAACCCTGA
4551  TAAATGCTTC AATAATATTG AAAAAGGAAG AGTATGAGTA TTCAACATTT
4601  CCGTGTCGCC CTTATTCCCT TTTTTGCGGC ATTTTGCCTT CCTGTTTTTG
4651  CTCACCCAGA AACGCTGGTG AAAGTAAAAG ATGCTGAAGA TCAGTTGGGT
4701  GCACGAGTGG GTTACATCGA ACTGGATCTC AACAGCGGTA AGATCCTTGA
4751  GAGTTTTCGC CCCGAAGAAC GTTTTCCAAT GATGAGCACT TTTAAAGTTC
4801  TGCTATGTGG CGCGGTATTA TCCCGTATTG ACGCCGGGCA AGAGCAACTC
4851  GGTCGCCGCA TACACTATTC TCAGAATGAC TTGGTTGAGT ACTCACCAGT
4901  CACAGAAAAG CATCTTACGG ATGGCATGAC AGTAAGAGAA TTATGCAGTG
4951  CTGCCATAAC CATGAGTGAT AACACTGCGG CCAACTTACT TCTGACAACG
5001  ATCGGAGGAC CGAAGGAGCT AACCGCTTTT TTGCACAACA TGGGGGATCA
5051  TGTAACTCGC CTTGATCGTT GGGAACCGGA GCTGAATGAA GCCATACCAA
5101  ACGACGAGCG TGACACCACG ATGCCTGTAG CAATGGCAAC AACGTTGCGC
5151  AAACTATTAA CTGGCGAACT ACTTACTCTA GCTTCCCGGC AACAATTAAT
5201  AGACTGGATG GAGGCGGATA AAGTTGCAGG ACCACTTCTG CGCTCGGCCC
5251  TTCCGGCTGG CTGGTTTATT GCTGATAAAT CTGGAGCCGG TGAGCGTGGG
5301  TCTCGCGGTA TCATTGCAGC ACTGGGGCCA GATGGTAAGC CCTCCCGTAT
5351  CGTAGTTATC TACACGACGG GGAGTCAGGC AACTATGGAT GAACGAAATA
5401  GACAGATCGC TGAGATAGGT GCCTCACTGA TTAAGCATTG GTAACTGTCA
5451  GACCAAGTTT ACTCATATAT ACTTTAGATT GATTTAAAAC TTCATTTTTA
5501  ATTTAAAAGG ATCTAGGTGA AGATCCTTTT TGATAATCTC ATGACCAAAA
5551  TCCCTTAACG TGAGTTTTCG TTCCACTGAG CGTCAGACCC CGTAGAAAAG
5601  ATCAAAGGAT CTTCTTGAGA TCCTTTTTTT CTGCGCGTAA TCTGCTGCTT
5651  GCAAACAAAA AAACCACCGC TACCAGCGGT GGTTTGTTTG CCGGATCAAG
5701  AGCTACCAAC TCTTTTTCCG AAGGTAACTG GCTTCAGCAG AGCGCAGATA
5751  CCAAATACTG TCCTTCTAGT GTAGCCGTAG TTAGGCCACC ACTTCAAGAA
5801  CTCTGTAGCA CCGCCTACAT ACCTCGCTCT GCTAATCCTG TTACCAGTGG
5851  CTGCTGCCAG TGGCGATAAG TCGTGTCTTA CCGGGTTGGA CTCAAGACGA
```

FIG. 13B5

```
5901  TAGTTACCGG ATAAGGCGCA GCGGTCGGGC TGAACGGGGG GTTCGTGCAC
5951  ACAGCCCAGC TTGGAGCGAA CGACCTACAC CGAACTGAGA TACCTACAGC
6001  GTGAGCTATG AGAAAGCGCC ACGCTTCCCG AAGGGAGAAA GGCGGACAGG
6051  TATCCGGTAA GCGGCAGGGT CGGAACAGGA GAGCGCACGA GGGAGCTTCC
6101  AGGGGGAAAC GCCTGGTATC TTTATAGTCC TGTCGGGTTT CGCCACCTCT
6151  GACTTGAGCG TCGATTTTTG TGATGCTCGT CAGGGGGGCG GAGCCTATGG
6201  AAAAACGCCA GCAACGCGGC CTTTTTACGG TTCCTGGCCT TTTGCTGGCC
6251  TTTTGCTCAC ATGTTCTTTC CTGCGTTATC CCCTGATTCT GTGGATAACC
6301  GTATTACCGC CTTTGAGTGA GCTGATACCG CTCGCCGCAG CCGAACGACC
6351  GAGCGCAGCG AGTCAGTGAG CGAGGAAGCG GAAGA
```

METAL RESISTANT PLANTS AND PHYTOREMEDIATION OF ENVIRONMENTAL CONTAMINATION

CROSS REFERENCE TO RELATED APPLICATIONS

This application is filed under 35 U.S.C. 371 based on PCT US01/48105, filed Dec. 13, 2001, which international application claims benefit of U.S. Provisional Applications 60/255,001, filed Dec. 13, 2000, and 60/300,525, filed Jun. 22, 2001.

ACKNOWLEDGMENT OF FEDERAL RESEARCH SUPPORT

This invention was made, at least in part, with funding from the United States Department of Energy (Grant No. DE-FG07-96ER20257). Accordingly, the United States Government has certain rights in this invention

BACKGROUND OF THE INVENTION

The field of this invention is the area of plant molecular biology, in particular the genetic engineering of plants to express chimeric genes determining resistance to heavy metals and/or thio-reactive metals, for example, a plant-expressible arsenate reductase coding sequence and/or a phytochelatin biosynthetic enzyme (and optionally, a mercuric ion reductase gene) and the use of such plants in the phytoremediation of environmental pollutants including arsenate, arsenite, cobalt, copper, zinc, mercury, platinum, palladium, antimonate and cadmium ions.

As a consequence of the industrial revolution there has been a significant increase in anthropogenic emission of heavy metals into the biosphere (Ayers, 1992). Mining, smelting, vehicle exhausts, and toxic run-off agricultural products are the source of most anthropogenic pollution of soils and sediments (Nriagu, 1980). These activities have led to solid contaminated particularly with heavy metals such as Cu, Zn, Pb, Ni, Cd, Hg and As. Cadmium is a toxic metal widely spread in the environment and in foods consumed by man (Sherlock, 1984). Major uses of cadmium include electroplating (35%), paint pigments (25%), plastic stabilizers (15%), and batteries (15%) (Nriagu, 1980). One serious soil-related pollution problem is the elevated level of cadmium in agricultural products such as phosphate fertilizers and cadmium containing sewage sludges (Nicholson and Jones, 1994); Ryan et al., 1982) and cadmium accumulation in plants grown on the cadmium-contaminated soil and sediments. Chronic exposure to such soils and consumption of contaminated food pose a serious threat to human and animal health (Sherlock, 1984). Cadmium exposure causes anemia, hypertension, hepatic, renal and cardiovascular disorders.

Physical remediation methods like soil removal and burial are impractical because the expense involved in large-scale removal is too great. Moreover, unlike organic waste, which can be mineralized, metals are immutable and can not be degraded into harmless constituents (Meagher, 2000). Phytoremediation, the use of green plants to remove toxic contaminants from soil and water, is an environmental friendly and cost effective solution for cleaning up metal contaminated sites and it has been suggested that plants might play a significant role in the phytoremediation of toxic heavy metals such as Hg, As, Cd, Cr, Zn, Ni, and Pb from contaminated soil and water (Raskin, 1996).

For a successful phytoremediation strategy, plants must be able to tolerate and hyperaccumulate the toxic metals aboveground (Goldsbrough, 1998). A number of plant species can hyperaccumulate metals in their aboveground tissues to levels far exceeding those present in soil or in the non-hyperaccumulating species growing nearby (Baker and Brooks, 1989). Hyperaccumulation is usually defined as levels of metal ions greater than 0.1%-1% of the dry weight of the plant (Baker, 2000). At these concentrations the recovery of metals from the plant tissues is potentially economical (Baker, 2000). Recovery of even low hyperaccumulated concentrations of most toxic metals such as As, Cd, and Hg could be economically viable as an alternative to the extreme expense of physical remediation methods. In the past few years, interest has been shown to exploit plants' natural properties to remediate toxic heavy metals soils through phytoextraction and phytomining (Brown et al., 1995b; McGrath et al., 1993); Robinson et al., 1997). Unfortunately, most of these hyperaccumulator species are small and slow growing, therefore, their potential for large scale remediation of polluted sites is limited (Ebbs et al., 1997).

Bacterial cells have developed more assertive solutions to exposure to environmental toxins (Meagher, 2000). Bacteria have evolved mechanisms to reduce, oxidize or modify metal ions to less toxic forms and eliminate these toxic metals from their cytoplasm by specific transporters (Tsai et al., 1997). One such system is the ars operon which provides resistance to arsenate and arsenite. Resistance to arsenate is acquired by first reducing it to arsenite by the action of the arsC protein in conjunction with glutathione.

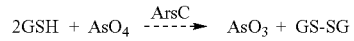

$$2GSH + AsO_4 \xrightarrow{ArsC} AsO_3 + GS\text{-}SG$$

Arsenite is then pumped from the cell by the arsA/arsB complex (Rosen, 1999). The manipulation of bacterial arsenic resistance gene may provide resistance to arsenate and other metal ions. Bacterial genes modified for plant expression have been successfully expressed in plants for phytoremediation purposes. Transgenic plants expressing modified bacterial merA and merB genes have been shown to efficiently extract of elemental and methylmercury from contaminated media (Bizily et al., 1999; Rugh et al., 1998; Rugh et al., 1996). Similarly, transgenic Indian mustard plants overexpressing *E. coli* thio-rich peptides showed enhanced accumulation and tolerance to Cd (Zhu et al., 1999a; Zhu et al. 1999b).

Genetically engineered high biomass transgenic plants expressing genes responsible for hyperaccumulation hold potential for making phytoremediation a viable commercial technology (Brown et al., 1995a; Rugh et al., 1998). Higher plants can extract pollutants from the soil or water through their root systems, store and concentrate the pollutants in their cells and/or convert toxic pollutants to less toxic forms. Roots are more directly in contact with heavy metals in the environment than shoots and root growth usually responds more rapidly to metal exposure than shoot growth. Plants may produce up to $100 \times 10^6$ miles of roots per acre and thus plants are in contact with a vast expanse of soil surface area (Dittmer, 1937). Plant roots can also reach reasonable depths into the soil surface area (Stone and Kalisz, 1991). Therefore, one phytoremediation approach for heavy metals is to use plant roots to extract, the vascular system to transport, and leaves as a sink to concentrate the heavy metals aboveground. Our initial aim was to study whether ArsC protein reduces other structurally related metal ions. Herein, we disclose that the expression of arsC gene modified for expression in plants enables bacterial cells and transgenic plants including, but not limited to, transgenic *Arabidopsis* plants to grow on otherwise toxic levels of Cd(II) by reducing it to Cd(0).

There is a long felt need in the art for the in situ remediation of toxic metal ions including but not limited to arsenate; mercury, arsenite, antimony, zinc, copper, cobalt, platinum, palladium, and cadmium ions and ion complexes thereof. The present invention enables phytoremediation and/or revegetation of contaminated environments, especially those contaminated with cadmium, via the plant-expressible arsenate reductase and/or phytochelatin biosynthetic sequences and/or mercury reductase coding sequences disclosed herein.

SUMMARY OF THE INVENTION

The present invention provides nucleic acid sequences which mediate resistance to cadmium ions and ion complexes in transgenic plants or plant cells which express these sequences encoding arsenate reductase, as specifically exemplified, arsC, operably linked to transcriptional and translational control sequences which are functional in plants. Preferably the coding sequence is that of plant-expressible bacterial arsC, desirably the gene from the bacterial resistance plasmid R773. Other suitable arsenate reductase coding sequences include those bacterial arsenate reductase sequences available on GenBank (see Table 3). Where cadmium resistance is desired, the promoter used can be constitutive, tissue-specific or inducible, but is desirably constitutive, e.g., from a plant actin 2 gene, a plant ubiquitin or from the cauliflower mosaic virus 35C or 19S gene.

A further aspect of the present invention are transgenic plant cells, plant tissue and plants which have been genetically engineered to contain and express a plant-expressible cadmium resistance coding sequence operably linked to transcriptional and translational control sequences which are functional in plants. Preferably the coding sequence is that of plant-expressible arsC (such as that derived from R773 arsC) and the plant-expressible transcriptional control sequence directs ArsC expression in the above-ground plant tissue, e.g., a light regulated promoter. As specifically exemplified herein, the transcriptional control sequences are from the rubisco small subunit gene of soybean, but chlorophyll A/B binding protein promoters are also light-regulated and could be used as well.

Also provided by the present invention are methods for effecting arsenate resistance in plants by stably transforming a plant to contain and express a nucleotide sequence of a plant-expressible cadmium resistance coding sequences operably linked to transcriptional and translational control sequences which are functional in plants. Preferably the coding sequence is that of plant-expressible arsC which encodes arsenate reductase. The sequence of the protein and its coding sequence are available under GenBank Accession No. J02591. See also SEQ ID NO:3 and SEQ ID NO:4. As specifically exemplified, the plant-expressible cadmium resistance coding sequences are those from the resistance plasmid R773 arsC gene, adapted for plant gene expression (See FIG. 1). The plant-expressible transcriptional control sequences should only direct expression in above-ground plant tissue(s). Light-regulated promoters such as those from soybean SRS1 or chlorophyll binding protein genes. Where arsenate resistance and/or hyperaccumulation is desired, the plant should also contain and express at least one phytochelatin biosynthetic enzyme coding sequence, preferably expressed under the control of a strong constitutive promoter such as 35S or 19S of CaMV, ubiquitin or a plant actin 2 promoter.

The present invention further provides both plant-expressible constitutive and plant-expressible inducible (in response to light) phytochelatin biosynthetic sequences for use in the genetic engineering of plants to provide plants which are tolerant of heavy metal ions and which can take up and sequester heavy metals ions from contaminated soil or water environment. As specifically exemplified, the constitutive promoter is the ACT2 promoter from *Arabidopsis thaliana* or the light regulated SRS1 promoter from soybean, and the biosynthetic enzymes are γECS and PCS. The heavy metals include, without limitation, mercuric ion, cadmium as well as divalent ions of zinc, cobalt, copper, thio active metal ions, in addition to arsenate and arsenite. Desirably, where arsenate resistance and/or accumulation is needed, the expression of any endogenous arsenate reductase gene in root is reduced (or eliminated) through antisense, co-suppression, interfering RNA or a knockout of the gene. Also within the scope of the present invention are recombinant DNA molecules, recombinant bacterial and eukaryotic cells, and recombinant plant cells, plant tissue and plants which contain and express at least one phytochelatin biosynthetic coding sequence (GS, ECS, PCS).

It is possible to silence gene activities of interest using a dominant transgene approach based on double stranded RNA expression that leads to cosuppression of the target gene (Jorgensen et al., 1999; Plasterk and Ketting, 2000; Chuang and Myerowitz, 2000). This technology is applicable to silencing of the endogenous plant arsenate reductase gene. In a demonstration project, PCR is used to amplify the 3' untranslated region of the *A. thaliana* arsenate reductase gene and it is cloned in reverse and forward orientations flanking a GUS (β-glucuronidase) spacer region to create the desired stem-loop RNA product where the stem region of the RNAi (interfering RNA) is made from the 3' untranslated region of the *Arabidopsis* gene. RNAi constructs to suppress the arsenate reductase gene (acr2) are expressed from a CaMV 35S or an ACT2 promoter. These are constitutive promoters, and thus, the endogenous plant gene is silenced throughout the plant. The plant-expressible light-regulated ArsC (bacterial coding sequence) provides for arsenate reductase in above ground plant tissue. By this strategy, uptake and transport of arsenate by roots leads to efficient reduction and sequestration in above ground plant tissue (where at least one phytochelatin biosynthetic enzyme is also expressed at least in above ground tissue and/or throughout the plant). Diagrams of the construct and the RNAi expression product are shown in FIG. 15.

Also within the scope of the present invention are methods for the bioremediation of arsenate and/or cadmium-contaminated environments, including soil, sediments, mine tailings, water, industrial waste, groundwater and air. Environments contaminated with other metal ions (copper, cobalt, zinc, antimonate, mercury, palladium, platinum, e.g.) can also be remediated using the transgenic plants of the present invention. The recombinant organisms including, but not limited to, recombinant unicellular organisms (e.g., bacteria, blue green bacteria, yeasts and the like, transgenic plants or transgenic macroalgae expressing the bacteria-derived arsC coding sequence are useful in the bioremediation when planted in contaminated environments or when irrigated with water contaminated with cadmium, arsenate, arsenite, mercury, zinc, cobalt or copper. Where cadmium resistance is desired, it is not essential that the transgenic plant be transformed to contain and express a phytochelatin biosynthetic enzyme coding sequence. Where mercury resistance and/or phytoremediation is desired, the transgenic plant contains and expresses at least one phytochelatin biosynthetic enzyme coding sequence and a mercuric reductase (merA) coding sequence.

Where hyperaccumulation of arsenic from arsenate-contaminated environments for phytoremediation is desired, it is preferred that expression of arsenic reductase is restricted to above-ground tissue and overexpression of at least one phytochelatin biosynthetic enzyme (PCS, GS and/or gamma-ECS) is achieved throughout the plant.

Also provided in the present invention are methods for producing highly specific antibodies against a protein of interest, especially for detecting the presence of that protein in a plant, for example, a transgenic plant. The immunogen in this instance is a branched "multiple antigen peptide" (MAP) in which oligopeptides of about 25-35 (especially 29-30) amino acids corresponding in sequence to the N-terminus of the protein of interest are presented in the MAP format.

BRIEF DESCRIPTION OF THE DRAWINGS

FIGS. 6A-6C illustrate phytochelatin (PC) synthesizing enzymes and MAP peptides. FIG. 6A: Three enzymes are required for PC synthesis: The PCs are non-ribosomally synthesized peptides made with the structure (γ-Glu-Cys)$_n$Gly, where n is generally 2-11. γECS catalyzes the condensation of glutamate (Glu) and cysteine (Cys) to form γGlu-Cys, which contains an unconventional peptide bond between the γ-carboxyl group of Glu and the α-amino group of Cys. GS (glutathione synthase) catalyzes the formation of a peptide bond between glycine (Gly) and the carboxyl group of Cys in γGlu-Cys, resulting in the synthesis of the tripeptide glutathione (GSH). GS is not highly specific and other amino acids, commonly alanine (β-Ala) or serine (Ser), can be substituted for Gly in this reaction. PS (phytochelatin synthase) catalyzes the addition of multiple γGlu-Cys units to GSH or its relatives, resulting in the synthesis of phytochelatins. FIG. 6B: Diagram of a Multiple Antigenic Peptide (MAP). MAPs were synthesized for all three PC synthesizing enzymes. The four-fold redundant MAP structure shown is built from a core of three lysines. The first lysine residue, which is attached to the support resin during synthesis, becomes the C-terminal residue in the MAP. The two lysines added during the second round of amino acid additions provide the four amino groups on which the four redundant peptides are built. The amino groups of the core lysines added in the first ($\alpha_1$, $\epsilon_1$) and second ($\alpha_2$, $\epsilon_2$) addition cycles are indicated. The first residue of the redundant peptide is drawn with its amino acid side-chain indicated as $R_1$. The remaining N-terminal portion of the redundant peptide is shown with a squiggly line. FIG. 6C: Three N-terminal peptides were synthesized as MAPs in this study. The peptides for γECS (ECS-NMAP) (SEQ ID NO:11) and, GS (GS-NMAP) (SEQ ID NO:12) were 30 amino acids long, while that for PS (PS-NMAP) (SEQ ID NO:13) was 29 residues long. Numbers indicate residue locations in the sequence relative to the first encoded residue, the initiator methionine, which was omitted from each sequence.

FIGS. 7A-7D summarize the results obtained in ELISA assays with peptide and crude extracts as antigens. FIG. 7A: Secreted antibodies from four hybridomas were reactive with γECS protein in crude bacterial extracts. The ELISA reactivity of the four best mAbs with bacterial extracts expressing γECS from pET15b vector (+ECSEx) as compared to bacterial extracts with the empty vector (−ECSEx). FIG. 7B: Secreted antibodies from four hybridomas were reactive with GS protein expressed from a pBluescript (+GSEx) in contrast to crude bacterial extracts from strains with an empty vector (GSEx). FIG. 7C: Secreted antibody from 17 hybridomas were reactive with microtiter plate wells containing 10 ng PS-NMAP (synthetic peptide, PS-NMAP) and blocked with bovine serum albumin in contrast to sample wells only blocked with BSA (Control). FIG. 7D: A subset of the secreted antibody from the same 17 hybridomas shown in FIG. 7C were reactive with PS protein in crude bacterial extracts expressed from pET15b (+PSEx) in contrast to empty vector controls (−PSEx). Optical density titer values in FIGS. 7A-7D are given for 25 μL of the hybridoma cell supernatant.

FIGS. 8A-8C: Western analysis of several monoclonal antisera to γECS, GS, and PS crude protein extracts from *E. coli* are presented in FIG. 8A, 8B, and 8C, respectively. The cell supernatants or purified monoclonal antiserum from each of the best three or four cell lines reacting with each protein were used as the source of antibody. The reactivity of crude bacterial protein extracts from bacteria over-expressing the protein of interest were compared to control bacterial extracts from strains with an empty vector. The background observed in all control wells for γECS and some control wells for GS antibody result from endogenous expression of these *E. coli* proteins. FIGS. 8D-8F: Western analysis of monoclonal antisera mAbECS1 and mAbGS1 to γECS and GS expressed in transgenic *Arabidopsis* plant extracts are shown in D and F respectively Extracts from the different sets of independent recombinant plants are labeled numerically. *E. coli* extracts expressing protein and wild-type plant extracts lacking protein are labeled Ec and WT, respectively. The molecular weight in kilodaltons (kd) of the native *E. coli* proteins is listed in the left margin.

FIG. 9A: Leaf cells from transgenic plants expressing bacterial γECS labeled with mAbECS1. FIGS. B and 9C: Leaf cells from transgenic plants expressing bacterial GS labeled with mAbGS1 (FIG. 9B) and mAbGS2 (FIG. 9C). FIG. 9D: Wild-type plant cells reacted with mAbGS1.

FIGS. 10A-10B provide comparisons of growth of ECS-expressing the transgenic *brassica* plants of Zhu et al. (1999) vs those of the present invention. FIG. 10A: the data for relative growth (harvest fresh weight of plants minus controls at time zero divided by the control weight) of two *Brassica juncia* line expression 35S promoter-regulated ECS vs control plants (wild type, WT). FIG. 10B: The data on total growth (harvest fresh weight of plants) of two lines of *Arabidopsis* plants expressing ACT2-regulated ECS vs control plants (WT).

FIGS. 12B1-12B4 provide an annotated sequence for pACTB. The ACT2 sequences include exon O, intron IVSL and exon I. See also SEQ ID NO:14.

DETAILED DESCRIPTION OF THE INVENTION

Figure 1:
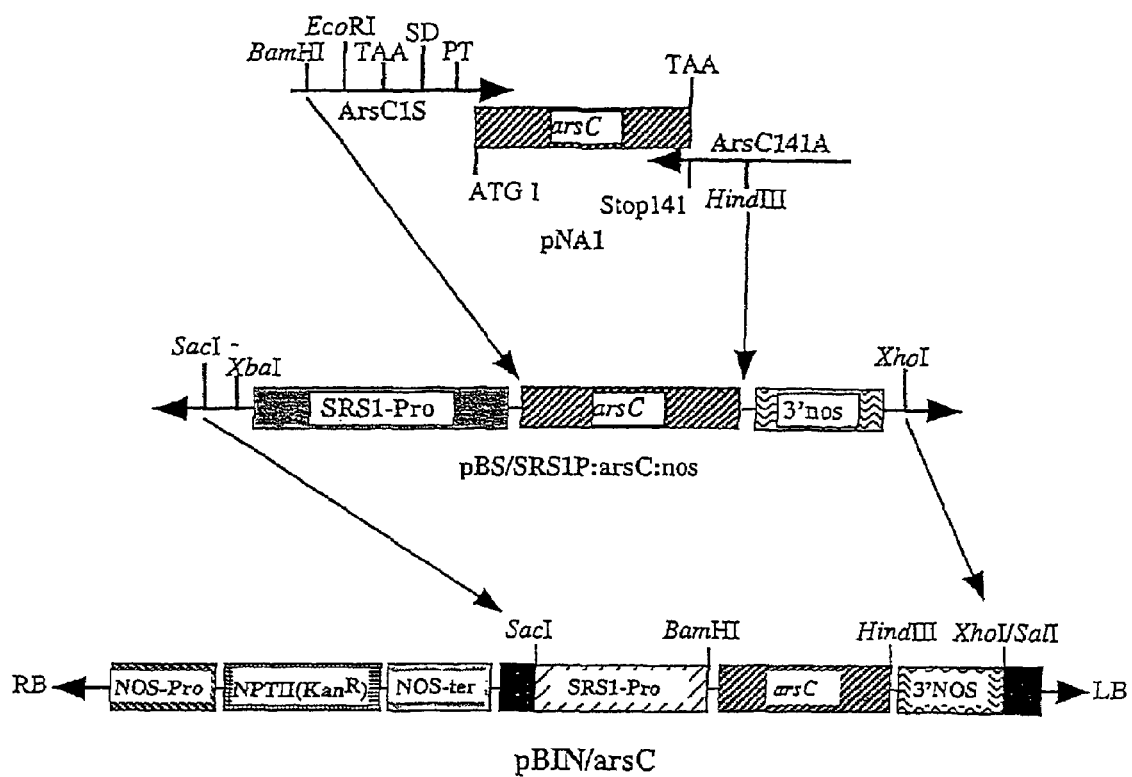
FIG. 1 schematically illustrates the construction of the plant-expressible arsC construct and the insertion into the plant transformation vector pBIN4.

Genetically engineered high biomass transgenic plants expressing genes responsible for hyperaccumulation and/or metal ion detoxification or sequestration make phytoremediation a viable commercial technology. Higher plants can extract pollutants from the soil or water through their root systems, store and concentrate the pollutants in their cells and/or convert toxic pollutants to less toxic forms. Roots are more directly in contact with heavy metals in the environment than shoots and root growth usually responds more rapidly to metal exposure than shoot growth. Plants may produce up to $100 \times 10^6$ miles of roots per acre and thus plants are in contact with a vast expanse of soil surface area. Plant roots can also reach reasonable depths into the soil surface area. Therefore, one phytoremediation approach for heavy metals is to use plant roots to extract, the vascular system to transport, and leaves as a sink to concentrate the heavy metals aboveground using phytochelatins. Effective levels of plant phytochelatins or other metal resistance protein(s) are accomplished by "overexpressing" (as compared to the expression levels in a wild type plant) one or more enzymes involved in the biosynthesis of the phytochelatins. In the present invention either the γ-ECS (γglutamylcysteine synthase), GS (glutathione synthase) or PCS (phytochelatin synthase) coding sequence, for example, those coding sequences disclosed in GenBank Accession Nos. X03954, 28377 and Z68144, respectively, have been expressed under the regulatory control of the constitutive ACT2 promoter, as specifically exemplified, that derived from *Arabidopsis thaliana*, or the light-regulated SRS1 promoter, as specifically exemplified, that from *Glycine max*. Combinations of two or three of these coding sequences can also be used. The PCS gene from *A. thaliana* is also disclosed in Vatamaniuk et al. (1999) *Proc. Natl. Acad. Sci. USA* 96:7110-7115. These two promoters driving expression of gamma-ECS, PS and/or GS provide surprisingly improved results as compared with those reported by Zhu et al. (1999) Zhu et al. (1999) *Plant Physiology* 119(1):73-80 and Zhu et al. (1999) *Plant Physiology* 1121:1169-1177. The SRS1-regulated constructs direct the expression of the operably linked coding sequences in leaf but not roots, they are extremely resistant and they hyperaccumulate metals in the above-ground plant tissues. Transgenic plants genetically engineered to express phytochelatin synthetic coding sequences under the regulatory control of the promoters specifically exemplified herein are tolerant to higher levels of mercuric, arsenate and cadmium ions than are prior art plants, and the present plants also accumulate such ions within plant tissue to higher levels than those levels achieved in prior art plants. Whereas the prior art plants reported by Zhu et al. (supra) appear to grow about 1.5 to 2 times better than wild type control plants in the presence of cadmium, the plants of the present invention grow about times better than the wild type control plants in the presence of 65 μM mercury or 250 μM arsenate. Both arsenate reductase and phytochelatin biosynthetic enzyme chimeric genes can be combined in a single plant genome by cotransformation of two constructs, by sequential transformation or by cross-breeding singly transformed plants, each containing one of the genetic constructs of interest, with selection for progeny having both the arsenate reductase coding sequence and the phytochelatin biosynthetic coding sequence(s). Alternatively, the two (or more) chimeric genes can be combined in a single plant by conventional breeding and screening (phenotypic or for molecular markers) to obtain the plant(s) which express(es) both the arsenate reductase sequence and the at least one phytochelatin biosynthetic enzyme coding sequence.

In plants, the constitutive plant-expressible transcription and translation regulatory element effects the expression of a downstream plant-expressible metal resistance coding sequence. Constitutive promoters include the ACT2 promoter of *Arabidopsis* (or the corresponding promoters from other plants). See, e.g., An et al. (1996) *The Plant Journal* 10:107-121 and hereinbelow. Data are presented for cadmium resistance in *Arabidopsis thaliana* genetically engineered to contain and express plant-expressible phytochelatin biosynthetic sequences, in particular, those encoding γECS, GS and PCS coding sequences. Plants in which a phytochelatin synthetic coding sequence is co-expressed together with an arsenate reductase coding sequence are further improved in metal resistance. Similar results are obtained in other plants, including monocots, dicots and gymnosperms, after stable transformation and regeneration according to methods well known and readily accessible to one of ordinary skill in the art.

The transgenic metal-resistant plants of the present invention are useful in the phytoremediation and/or revegetation of soils contaminated with divalent cadmium or mercury cations or arsenate or arsenite ions, and they are also useful for removing and sequestering these ions from water, wastewater and aqueous environments contaminated with cadmium, mercury, arsenate or arsenite. The plants of the present can be grown in soil or aquaculture, with contaminated water or waste water being applied for ion removal. These transgenic plants of the present invention can also be used in phytomining of contaminated soil, sediment, water and mine tailings, effecting the concentration of the heavy metals and allowing harvesting or removal. The choice of plants into which a phytochelatin biosynthetic sequence operably linked to an ACT2 or an SRS1 promoter (and optionally, a plant-expressible arsenate reductase coding sequence) is introduced is determined by the climate, soil and moisture conditions of the site where the plants are to be grown, as well understood by those of ordinary skill in the art. Mercury resistance is enhanced when a plant-expressible mercury reductase is also expressed (see, e.g. U.S. Pat. No. 5,668,294).

The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

As used herein expression directed by a particular sequence is the transcription of an associated downstream sequence. If appropriate and desired for the associated sequence, there the term expression also encompasses translation (protein synthesis) of the transcribed RNA. When expression of a sequence of interest is "up-regulated," the expression is increased. With reference to up-regulation of expression of a sequence of interest operably linked to the SRS1 transcription regulatory sequence, expression is increased in the presence light.

In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer (light) is available to the plant or plant tissue The ACT2 promoter as used in the present invention is constitutively active, providing high levels of expression of an associated coding sequence.

One DNA portion or sequence is downstream of second DNA portion or sequence when it is located 3' of the second sequence. One DNA portion or sequence is upstream of a second DNA portion or sequence when it is located 5' of that sequence. For plant gene expression, the 3' nontranslated sequence can be chosen from a number available in the art, and that specifically exemplified is that from the ACT2 gene of *Arabidopsis* (See An et al. (1996) vide infra).

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is a polynucleotide which is substantially separated from other polynucleotide sequences which naturally accompany a native phytochelatin biosynthetic sequence. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other phytochelatin biosynthetic. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction.

As used herein, the term "cadmium resistance" means that a non-naturally occurring organism is not inhibited by the presence of at least one ionic form of cadmium at concentrations (levels) at which a naturally occurring (wild-type) counterpart of the non-naturally occurring organism is inhibited or exhibits symptoms of toxicity. It is not intended that the term cadmium resistance refer to resistance to unlimited concentrations of cadmium ions, but rather the term is relative in that it relies on comparison to the properties of a parental strain. Resistance to other metal. ions is analogous. Resistance is measured relative to the sensitivity of a comparison wild-type plant to the toxic metal, and resistance is not to unlimited levels.

A "cadmium resistance coding sequence" is one which encodes a protein capable of mediating resistance to at least one cadmium ion, including, but not limited to, divalent cations of cadmium. Also within the scope of this definition are mutant sequences which determine proteins capable of mediating resistance to divalent cations of cadmium or other cadmium-containing ions or ion complexes.

With respect to a coding sequence, the term "plant-expressible" means that the coding sequence (nucleotide sequence) can be efficiently expressed by plant cells, tissue and whole plants. The art understands that a plant-expressible coding sequence has a GC composition consistent with good gene expression in plant cells, a sufficiently low CpG content so that expression of that coding sequence is not restricted by plant cells, and codon usage which is consistent with that of plant genes. Where it is desired that the properties of the plant-expressible metal resistance gene are identical to those of the naturally occurring cadmium resistance gene, the plant-expressible homolog will have a synonymous coding sequence or a substantially synonymous coding sequence. A substantially synonymous coding sequence is one in which there are one or more codons which encode a similar amino acid to a comparison sequence, or if the amino acid substituted is not similar in properties to the one it replaces, that change has no significant effect on enzymatic activity for at least one substrate of that enzyme. As discussed herein, it is well understood that in most cases, there is some flexibility in amino acid sequence such that function is not significantly changed. The skilled artisan understands such conservative changes in amino acid sequence, and the resultant similar protein can be readily tested without the expense of undue experimentation using procedures such as those disclosed herein. Where it is desired that the plant-expressible gene have different properties, there can be variation in the amino acid sequence as compared to the wild-type gene, and the properties of metal resistance can be readily determined as described herein, again without the expense of undue experimentation.

"Plant-expressible transcriptional and translational regulatory sequences" are those which can function in plants, plant tissue and plant cells to effect the transcriptional and translational expression of the nucleotide sequences with which they are associated. Included are 5' sequences to a target sequence to be expressed which qualitatively control gene expression (turn on or off gene expression in response to environmental signals such as light, or in a tissue-specific manner) and quantitative regulatory sequences which advantageously increase the level of downstream gene expression. An example of a sequence motif which serves as a translational control sequence is that of the ribosome binding site sequence. Polyadenylation signals are examples of transcription regulatory sequences positioned downstream of a target sequence, and there are several well known in the art of plant molecular biology; these include the 3' flanking sequences of the nos gene. Adaptation of a bacterial merA coding sequence for expression in plants cells is taught in U.S. Pat. No. 5,668, 294 and in Rugh et al. (1996). The upstream untranslated sequence taught therein can be utilized to improve expression of other sequences in plants as well.

A "non-naturally occurring recombinant nucleic acid molecule", e.g., a recombinant DNA molecule, is one which does not occur in nature; i.e., it is produced either by natural processes using methods known to the art but is directed by man to produce a desired result, or it has been artificially produced from parts derived from heterologous sources, which parts may be naturally occurring or chemically synthesized molecules or portions thereof, and wherein those parts have been joined by ligation or other means known to the art.

A "transgenic plant" is one which has been genetically modified to contain and express heterologous DNA sequences, either as regulatory RNA molecules or as proteins. As specifically exemplified herein, a transgenic plant is genetically modified to contain and express at least one heterologous DNA sequence operably linked to and under the regulatory control of transcriptional control sequences which function in plant cells or tissue or in whole plants. As used herein, a transgenic plant also encompasses progeny of the initial transgenic plant where those progeny contain and are capable of expressing the heterologous coding sequence under the regulatory control of the plant-expressible transcription control sequences described herein. Seeds containing transgenic embryos are encompassed within this definition.

When plant expression of a heterologous gene or coding sequence of interest is desired, that coding sequence is operably linked in the sense orientation to a suitable promoter and advantageously under the regulatory control of DNA sequences which quantitatively regulate transcription of a downstream sequence in plant cells or tissue or in planta, in the same orientation as the promoter, so that a sense (i.e., functional for translational expression) mRNA is produced. A transcription termination signal, for example, as polyadenylation signal, functional in a plant cell is advantageously placed downstream of the mercury resistance coding sequence, and a selectable marker which can be expressed in a plant, can be covalently linked to the inducible expression unit so that after this DNA molecule is introduced into a plant cell or tissue, its presence can be selected and plant cells or tissue not so transformed will be killed or prevented from growing. In the present invention, the cadmium resistance coding sequence can serve as a selectable marker for transformation of plant cells or tissue. Where constitutive gene expression is desired, suitable plant-expressible promoters include the 35S or 19S promoters of Cauliflower Mosaic Virus, the nos, ocs or mas promoters of the *Agrobacterium tumefaciens* Ti plasmids, a constitutive promoter such as a constitutive Act2 promoter such as that from *Arabidopsis* and others known to the art can be used. Where tissue specific expression of the plant-expressible cadmium resistance coding sequence is desired, the skilled artisan will choose from a number of well-known sequences to mediate that form of gene expression. Environmentally regulated promoters are also well known in the art, and the skilled artisan can choose from well known transcription regulatory sequences to achieve the desired result.

The polynucleotides may also be produced by chemical synthesis, e.g., by the phosphoramidite method described by Beaucage and Caruthers (1981) *Tetra. Letts.* 22: 1859-1862 or the triester method according to Matteuci et al. (1981) *J. Am. Chem. Soc.* 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature,* 334: 31-36. Many useful vectors for expression in bacteria, yeast, fungal, mammalian, insect, plant or other cells are well known in the art and may be obtained such vendors as Stratagene, New England Biolabs, Clontech, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art which is appropriate for the particular type of cell, including without limitation, transformation, lipofection or electroporation.

It is recognized by those skilled in the art that the DNA sequences may vary due to the degeneracy of the genetic code and codon usage. All DNA sequences which code for a phytochelatin biosynthetic protein and/or a mercury ion reductase and/or an arsenate reductase are included in this invention.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that the sequences of the exemplified phytochelatin biosynthetic enzymes, arsenate reductase and/or mercury reductase or the constitutive (ACT2) or light-regulated (SRS1) promoters of the present invention peptide can be used to identify and isolate additional, nonexemplified nucleotide sequences which are functionally equivalent to the sequences whose use is described herein.

Hybridization procedures are useful for identifying polynucleotides with sufficient homology to the subject regulatory sequences to be useful as taught herein. The particular hybridization techniques is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}$P, $^{35}$S, or the like. Non-radioactive labels include, for example, ligands such as biotin or thyroxine, as well as enzymes such as hydrolases or peroxidases, or a chemiluminescer such as luciferin, or fluorescent compounds like fluorescein and its derivatives. Alternatively, the probes can be made inherently fluorescent as described in International Patent Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak (1987) *DNA Probes*, Stockton Press, New York, N.Y., pp. 169-170, hereby incorporated by reference.

As used herein, moderate to high stringency conditions for hybridization are conditions which achieve the same, or about the same, degree of specificity of hybridization as the conditions employed by the current inventors. An example of high stringency conditions are hybridizing at 68° C. in 5×SSC/5× Denhardt's solution/0.1% SDS, and washing in 0.2×SSC/ 0.1% SDS at room temperature. An example of conditions of moderate stringency are hybridizing at 68° C. in 5×SSC/5× Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) *Current Protocols in Molecular Biology*, John Wiley & Sons, New York, N.Y., for further guidance on hybridization conditions.

Specifically, hybridization of immobilized DNA in Southern blots with $^{32}$P-labeled gene specific probes was performed by standard methods (Maniatis et al.) In general, hybridization and subsequent washes were carried out under moderate to high stringency conditions that allowed for detection of target sequences with homology to an exemplified coding or promoter sequence of the present invention. For double-stranded DNA gene probes, hybridization can be carried out overnight at 20-25° C. below the melting temperature (Tm) of the DNA hybrid in 6×SSPE 5× Denhardt's solution, 0.1% SDS, 0.1 mg/ml denatured DNA. The melting temperature is described by the following formula (Beltz, G. A., Jacobe, T. H., Rickbush, P. T., Chorbas, and F. C. Kafatos [1983] *Methods of Enzymology*, R. Wu, L, Grossman and K Moldave [eds] Academic Press, New York 100:266-285).

Tm=81.5° C.+16.6 Log [Na+]+0.41(+G+C)−0.61(% formamide)−600/length of duplex in base pairs.

Washes are typically carried out as follows: twice at room temperature for 15 minutes in 1×SSPE, 0.1% SDS (low stringency wash), and once at TM-20° C. for 15 minutes in 0.2× SSPE, 0.1% SDS (moderate stringency wash).

For oligonucleotide probes, hybridization was carried out overnight at 10-20° C. below the melting temperature (Tm) of the hybrid 6×SSPE, 5× Denhardt's solution, 0.1% SDS, 0.1 mg/ml denatured DNA. Tm for oligonucleotide probes was determined by the following formula: TM(° C.)=2(number T/A base pairs+4(number G/C base pairs) [Suggs, S. V., T. Miyake, E. H., Kawashime, M. J. Johnson, K. Itakura, and R. B. Wallace (1981) *ICB-UCLA Symp. Dev. Biol. Using Purified Genes*, D. D. Brown (ed.), Academic Press, New York, 23:683-693].

Washes were typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan. Other methods may become known in the future.

Thus, substitution, insertion, and deletion variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant polynucleotide to function in the same capacity as the polynucleotide from which the probe was derived. Preferably, this homology is greater than 80%, more preferably, this homology is greater than 85%, even more preferably this homology is greater than 90%, and most preferably, this homology is greater than 95%. The degree of homology or identity needed for the variant to function in its intended capacity depends upon the intended use of the sequence. It is well within the skill of a person trained in this art to make substitution, insertion, and deletion mutations which are equivalent in function or are designed to improve the function of the sequence or otherwise provide a methodological advantage. Methods for confirming promoter activity are known in the art.

The cadmium resistance protein (ArsC protein, arsenate reductase) is exemplified by that from R733 (Mobley et al., 1983; Rosenstein et al., 1992; Wu and Rosen, 1993; Day et al., 1994; Gladysheva et al. 1994; Oden et al., 1994; Shi et al., 1994; Carlin et al., 1995; Liu et al., 1995a; Liu et al., 1995b; Rosen, 1995; Bhattacharjee and Rosen, 1996). The amino acid sequence is given in SEQ ID NO:4. In addition to reducing cadmium ions, the ArsC protein also reduces arsenate, antimonate and tellurium.

Because cadmium resistant plants are useful for revegetation of contaminated soils (e.g., subsequent to mining operations) and/or bioremediation of soils and/or aquatic environments contaminated with ionic heavy metals including cadmium, the naturally occurring ArsC coding sequence derived from the bacterial resistance plasmid R773 was incorporated in transgenic plants under the regulatory control of the Cauliflower Mosaic Virus 35S plant-expressible promoter. The ArsC protein was produced at even greater levels than with the Rubisco promoter, and the transgenic plants exhibited greater resistance to cadmium ions than did control plants lacking this gene or plants carrying the SRSI-promoted ArsC sequence.

An additional benefit of the cadmium resistant plants is their ability to harvest metals; precious and semi-precious metals can be reduced and thereby trapped in plant tissues. These metals include can include cadmium, arsenic, antimony and tellurium where the corresponding metal ions are reduced by the ArsC gene product in those plants.

The present inventors have constructed DNA sequences which encode a cadmium resistance protein which is expressed in plant cells. See FIG. 1. The deduced amino acid sequence for the naturally occurring arsenate reductase protein (ArsC) is given in Table 2. The open reading frame extends from an ATG beginning at nucleotide 3286 through the stop codon ending at nucleotide 3711. Surprisingly, transgenic plants and plant cells expressing the ArsC protein were resistant to cadmium ions.

The function of the ArsC protein synthesized by *E. coli* cells expressing the arsC coding sequence from plasmid R773 is reflected in the cadmium resistance phenotypes of strains (See Table 1). Control cells were sensitive to cadmium cation and totally inactive in the reduction of cadmium ions.

Similar resistance to cadmium is observed in transgenic plant cells and tissues and in transgenic plants.

While the transgenic plants expressing the heterologous ArsC coding sequence were resistant to cadmium, at least some of these plants were hypersensitive to arsenate, presumably due to arsenite production. Arsenite is more toxic than arsenate.

Toxic ionic mercury (divalent) is efficiently reduced to Hg(0) by mercuric ion reductase. Hg(0) can be transpired up the vascular system of plants and out of leaves if the merA gene is expressed in all above and below ground organs. If merA only is expressed in roots then Hg(0) is reoxidized to Hg(II) in leaves by native catalase and peroxidase enzymes. By overexpression thiol rich peptides like glutathione and phytochelatins, Hg(II) can be trapped in a relatively inert form above-ground for later harvest.

Hyperaccumulation of toxic reactive metals depends upon making plants that are both highly metal ion tolerant and have the capacity to store enormous amounts of the metal above-ground. Greatly expanding aboveground sinks for thiol-reactive metals by elevating the levels of thiol-rich mercury-binding peptides in plants increases the ability to hyperaccumulate mercury and other toxic cations including but not limited to cadmium. Phytochelatins (PCs) are small peptides that are synthesized non-ribosomally from common amino acids precursors in a three-step enzymatic pathway.

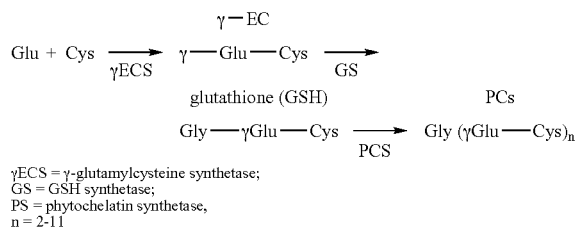

$\gamma$ECS = $\gamma$-glutamylcysteine synthetase;
GS = GSH synthetase;
PS = phytochelatin synthetase,
n = 2-11

We have cloned the $\gamma$ECS and GS genes by PCR from *E. coli* DNA starting with the public DNA database and genomic DNA. PCS genes from fission yeast and *Arabidopsis* were obtained in a collaborative arrangement with Julian Schroeder (U.C. San Diego) (Clemens et al., 1999; Cobbett, 1999; Vatamaniuk et al., 1999). We have modified the sequences of these genes by PCR to have the appropriate sites for cloning to make perfect (in-frame) translational fusions with our actin and SRS1 light regulated vectors and in the case of *Arabidopsis* PCS for detection in *E. coli* and plants. The sequences of all four modified clones were confirmed. We made monoclonal antibodies specific to each of the three enzymes $\gamma$ECS, GS, and PCS (fission yeast), to monitor their expression. The *Arabidopsis* PCS protein was tagged with an HA (hemagglutinin) epitope to allow monitoring with the commercially available HA-specific antibody. All four enzymes confer increased metal tolerance to *E. coli*, when expressed from the standard lac promoter in pBluescript vectors. We have cloned all four enzymes individually in *Arabidopsis*. All three enzymatic products ($\gamma$EC, GSH, and PC) can, in theory, bind mercury and contribute to mercury tolerance and accumulation. It is believed that the Gs-Hg and PC-Hg complexes are pumped into vacuoles for storage.

The most efficacious remediation of arsenate requires that plants extract arsenic from soil and hyperaccumulate it above ground in leaves and stems. To accomplish this, the chemical species of arsenic must be changes in different parts of the plant. The bacterial ArsC enzyme uses glutathione as a hydrogen/electron donor in the electrochemical reduction of the oxyanion arsenate to the oxyanion arsenite. While arsenate is a phosphate analogue, arsenite is chemically very different, being a highly reactive species with strong affinity toward thiol groups such as those in GSH, PCs and metallothioneins (Mts). Converting arsenate to arsenite favors the trapping of arsenic in thiol complexes. While all eukaryotic cells have some arsenate reduction capacity, we believe that this capacity must be enhanced in plants to be used for phytoremediation (via hyperaccumulation) and that the thiol sinks for the arsenite produced must also be increased in the plant cells. This is accomplished by genetic modification of the plant cells and plants to express heterologous PC synthetic genes and arsenate reductase, especially in the above ground tissue (leaves, shoots, stems).

The ArsC coding sequence has been cloned into *Arabidopsis* and tobacco under the control of two different promoters, the constitutive CaMV 35C promoter, and the light inducible SRS1 promoter from soybean. A new SRS1 plant expression cassette construct (SRS1pt) containing the SRS1p (promoter), convenient cloning sites and the nos transcription terminator (NOSt). ArsC was subcloned under the control of these regulatory elements to make SRS1p/ArsC. ArsC was also subcloned unto a standard 35Sp vector (pBIN19) to make 35Sp/ArsC. This construct is expressed in all tissues including leaves, stems and shoots, at relatively high levels.

Transgenic plant lines expressing 35Sp/ArsC were hypersensitive to arsenate. Leaves and roots grew more slowly than wild type controls on 75 µM arsenate and turned yellow; At 150 µM arsenate, the leaves with either ArsC transgene were extremely stunted, whereas SRSp/ArsC roots grew better than 35Sp/ArsC roots. This is due to the lack of ArsC protein synthesis in roots under the control of the light-regulated promoter and the resulting lower levels of arsenite produced. A study of the protein levels produced indicated that the ArsC protein was produced well in leaves with either promoter. Levels in roots and leaves were similar with the 35Sp construct, and there was no detectable protein in the roots for the SRS1p construct although leaves showed ArsC protein.

The percentage of arsenite is higher in leaves of ArsC plants than controls as determined by X-ray Absorption Near Edge Spectroscopy (XANES). Wild type and transgenic plants were grown on medium with sublethal levels of arsenate (50 µM). The results for four SRS1p/ArsC lines were examined. Leaves were harvested and the percent of each oxyanion was estimated. No free arsenite was detected in controls. The remaining 91-97% of the arsenic appeared to be in the form of thiol complexes.

We had expected the ArsC expressing plants to be more sensitive to arsenate because the ArsC product (arsenite) is so toxic. Arsenate itself should not be very toxic in most growth media because the media contain large amounts of phosphate (about 10 mM). Phosphate competes with arsenate for uptake and binding. Quantifying the speciation between arsenate and arsenite is performed using XANES. In both wild type and transgenic plants, approximately 95% of the arsenic in leaves was present in thiol complexes, consistent with a GSH conjugate of As(III) being stored in vacuoles. This suggests that most of the arsenate was already reduced in the control plants. The remaining arsenic was primarily arsenate in wild type plants, whereas in transgenic plants the reduced arsenite oxyanion usually predominant. Without wishing to be bound by theory, it is believed that plants have an efficient endogenous arsenite reductase. Most of the arsenite produced by the arsenate reductase reaction is bound in thiol complexes to reduce toxicity.

Hyperaccumulation of arsenic depends on plants that are tolerant of arsenate and its metabolites and have the capacity to store large quantities of arsenic metabolites in above ground tissue (to allow for harvesting and disposal). Two classes of thiol-rich chemical sinks for arsenite are tested in transgenic plants and each can confer arsenic tolerance. PC and GSH enable the formation of thiol-bound arsenic compounds with the result that toxicity is reduced and plant growth in the presence of arsenate is more robust.

The ACT2pt vector has been used to drive exceptionally high levels of constitutive transgenic expression of GS throughout the plant. The ACT2p contains intron (IVSL) which enhances expression 20-fold. The ACT2 poly(A) region (Act2t) ensures efficient transcription termination, and it contains multiple polyadenylation sites.

Exceptional high levels of transgene expression are required to create arsenic sinks of size sufficient to make an effective hyperaccumulator. The levels of PC pathway intermediates (gamma-EC, GSH and PC) are judged to need to be in excess of 1% of the total cell protein. Three vector systems were used for all three PC synthesizing enzymes in order to compare their activity and to avoid potential co-suppression problems. For strong constitutive expression and as an alternative promoter to CaMV's 35S promoter a novel actin promoter expression vector, Act2p was developed. It uses the promoter (p) and terminator (t) from the constitutive ACT2 gene (An et al., 1996). In controlled experiments with 30 independent Act2p/reporter lines and 30 independent 35Sp/reporter lines the Act2pt vector gives about 5-10 times higher levels of reporter expression than the 35Sp vector. In several independent experiments using the ACT2p vector we have never observed co-suppression of the endogenous ACT2 gene or the transgene, even when multiple copies were present. We never obtained a plant with low levels of ACT2p driven expression, whole 10-20% of the 35Sp plants had no detectable reporter expression. Furthermore, the lowest ACT2pt plants were equivalent to the highest 35Sp plants. This apparent insensitivity to cosuppression offers a significant advantage in the multigene strategy being used.

The most efficacious remediation of arsenic requires that plants extract arsenate from soil, transport it to above ground organs and hyperaccumulate it above ground in leaves and stems. To achieve the above ground accumulation of arsenic we needed strong leaf and stem specific expression to synthesize the metal binding peptides (PCs). We used the soybean SRS1pt and the PC synthesizing enzyme coding sequences were cloned into the SRS1pt vector.

We obtained extremely high level arsenic resistance from most *Arabidopsis* lines overexpressing gamma-ECS from the ACT2pt vector. The ACT2pt-ECS plant lines are significantly more resistant to arsenate than wild type over a 5 fold range in arsenic concentrations (100 µM-500 µM) that are lethal to the wild type. These plants grow about half as fast as unchallenged controls with 250 µM arsenate in the medium. While all the control plants died at that about of arsenate (about 19 ppm), most of the ACT2pt-ECS plants lived and went on to flower and set seed. Western blots confirmed that the protein was expressed at high levels in plants. Presumably the arsenite binds to the gamma-EC C (the immediate product of the gamma ECS enzyme) or the downstream products GSH or PCs. Plants were grown for 5 weeks at 24° C. with 16 hours light/8 hours dark.

We have generated specific monoclonal antibodies for functional studies as rapidly as we cloned genes of interest and expressed them in transgenic *Arabidopsis* plants as described herein. Sensitive and reliable detection of heterologous protein expressed in genetically modified organisms such as transgenic plants allows monitoring protein levels, tracking of potential unauthorized use and identifying the potential spread of a transgene outside cultivated areas which were actually planted with the genetically modified organism. Synthetic peptide immunogens were designed from the amino acid sequences of the three PC synthesizing enzymes, γECS, GS, and PS, obtained from GenBank (FIG. 6A). The first two were derived from *E. coli* sequences and PS from *S. pombe* sequence. They were synthesized as multiple antigenic peptides (MAPs, FIG. 6B), with 29-30 N-terminal amino acid residues (FIG. 6C), and designated ECS-NMAP, GS-NMAP, and PS-NMAP, respectively. Each MAP immunogen was injected three or more times into each of three mice, as described below.

The titers of antibodies in whole mouse serum were assayed against the three full-length proteins expressed from high copy vectors in *E. coli*. At least two of the three mice injected with each of the three immunogens (ECS-NMAP, GS-NMAP, PS-NMAP) gave significant titers to the bacterial extracts expressing the parent proteins, as shown in Table 5. While background was observed with the control bacterial extracts with the empty vector plasmid, the extracts expressing the corresponding antigen gave titer values 3.5-13 fold higher than background. The moderate background titers for the γECS and GS control extracts are to be expected, because these *E. coli* enzymes are expressed at low levels in wild-type *E. coli* cells. Even the best titers to whole fission yeast PS proteins for the mice injected with PS-NMAP were low, presumably due to low levels of PS protein expressed in the bacterial extracts. However, the background to the PS protein in control bacterial extracts was also lower, making the titers reproducible and easily interpreted. Mouse sera consistently gave very high titers to their corresponding immunogenic MAPs as shown for two mice immunized with PS-NMAP (Table 5).

The culture supernatants from hybridoma cells derived from mice with the highest titers were screened using the bacterial extracts expressing the three enzymes required for the synthesis of phytochelatins as the source of antigen in ELISAs as described hereinbelow. Several hybridoma pools secreting mAbs elicited with ECS-NMAP and GS-NMAP were easily identified as reacting with the over-expressed γECS and GS proteins in bacterial extracts. Data for four such hybridoma pools for each protein are presented in FIGS. 7A and 7B. Cell supernatants from these eight pools produced ELISA titers 10-30 fold over the background in control bacterial extracts. Several of these cell lines were further purified to homogeneity by limit dilution (Kohler and Milstein, 1975) using the same ELISA to identify positive hybridoma clones. The hybridomas making mAbs that were the most active against extracts expressing γECS and GS were selected for further analysis and designated mAbECS1, 2, and 3 and mAbGS1, 2, 3, and 4, respectively.

Putative hybridoma cells producing PS antibodies were also identified using the PS-NMAP and PS-containing bacterial extracts as antigens, as indicated in FIGS. 7C and 7D, respectively. From the 1082 hybridoma cell pools assayed in the ELISAs, 17 cell pools gave significant reactivity with PS-NMAP as antigen. Among these 17, four lines gave significant reactivity with bacterial PS extracts, mAbPS1, 2, 3, and 4 (FIG. 7D) and low background values with the control bacterial extract lacking PS. Two pools containing mAbPS5 and mAbPS10, had significant but low ratios of activity between PS and control extracts and were not examined further. The improved quantification of ELISAs with PS-NMAP, as antigen was essential during purification of the mAb-producing cell lines, because sensitive quantitative judgment is needed to distinguish pure cell lines from mixtures containing other undesired cell lines during limit dilution screening. The initial screening of hybridoma cell extracts with the NMAP antigen had been performed as a precaution due to concerns that the low titers obtained with PS protein extracts might result in our missing active pools. As shown in FIGS. 7C and 7D, this concern for the reliability of the protein ELISAs proved to be unfounded.

Figure 8A:
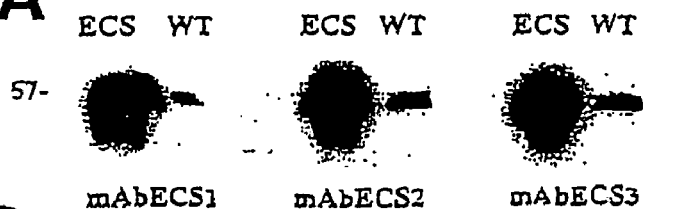
FIGS. 8A-8F are the results of Western analysis of monoclonal antibodies reactive with PC synthesizing enzymes.
Figure 8B:
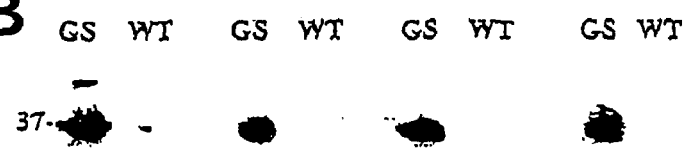
Figure 8C:
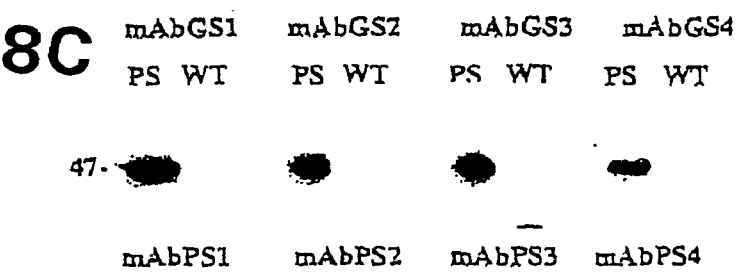

The reactivity of the mAbs from purified cell lines were each assayed on Western blots of extracts from bacteria expressing γECS, GS, and PS as shown in FIGS. 8A, 8B, and 8C, respectively. In each case, strong bands were observed in lanes with the high expression vector, which expressed the correct protein, and very little if any signal was observed in the control bacterial extract lane on short exposures of the autoradiograph. Each band migrated at the expected molecular weight position relative to standards. Because the γECS and GS genes cloned encode native *E. coli* proteins, relatively weak bands were observed in the correct molecular weight position in the control extracts on long exposures of the film, but the levels in the over-expression cells were significantly greater.

Figure 8D:
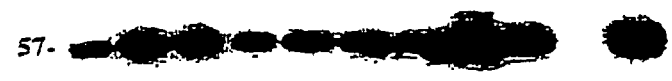
Figure 8E:
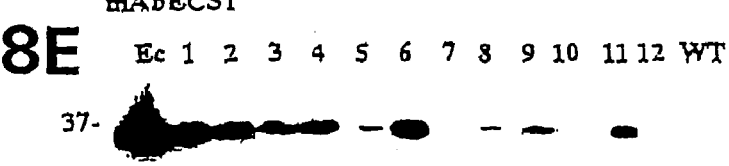
Figure 8F:
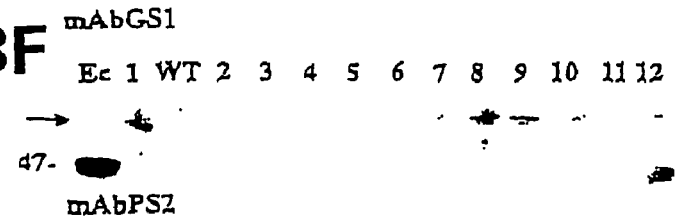

The reactivity of the mAbs from purified cell lines were also assayed on Western blots of extracts from plants. The three PC synthesizing enzymes were expressed in transgenic plants under the control of a constitutive *Arabidopsis* (actin) ACT2 promoter (An et al., 1996). The mAbs to γ-ECS and GS reacted strongly to proteins of the expected molecular weights in extracts of plants expressing these proteins as shown in FIGS. 8D and 8E. However, very weak bands were detected with mAbs to PS expressed in transgenic plants. The low level of PS protein detected may also result from the fact that many yeast genes are poorly expressed in plants due to cryptic polyadenylation sites within their coding regions (Grec et al., 2000).

Figures 9A, 9B, 9C, 9D:
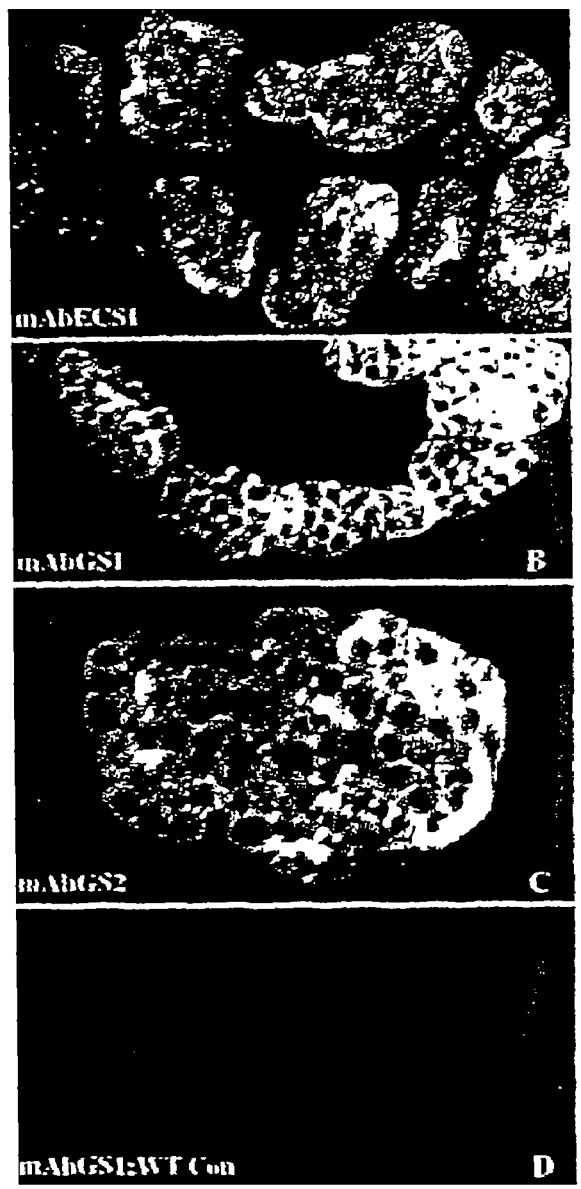
FIGS. 9A-9D show the results of immunofluorescence localization of ECS and GS proteins in transgenic *Arabidopsis*.
Figure 11:
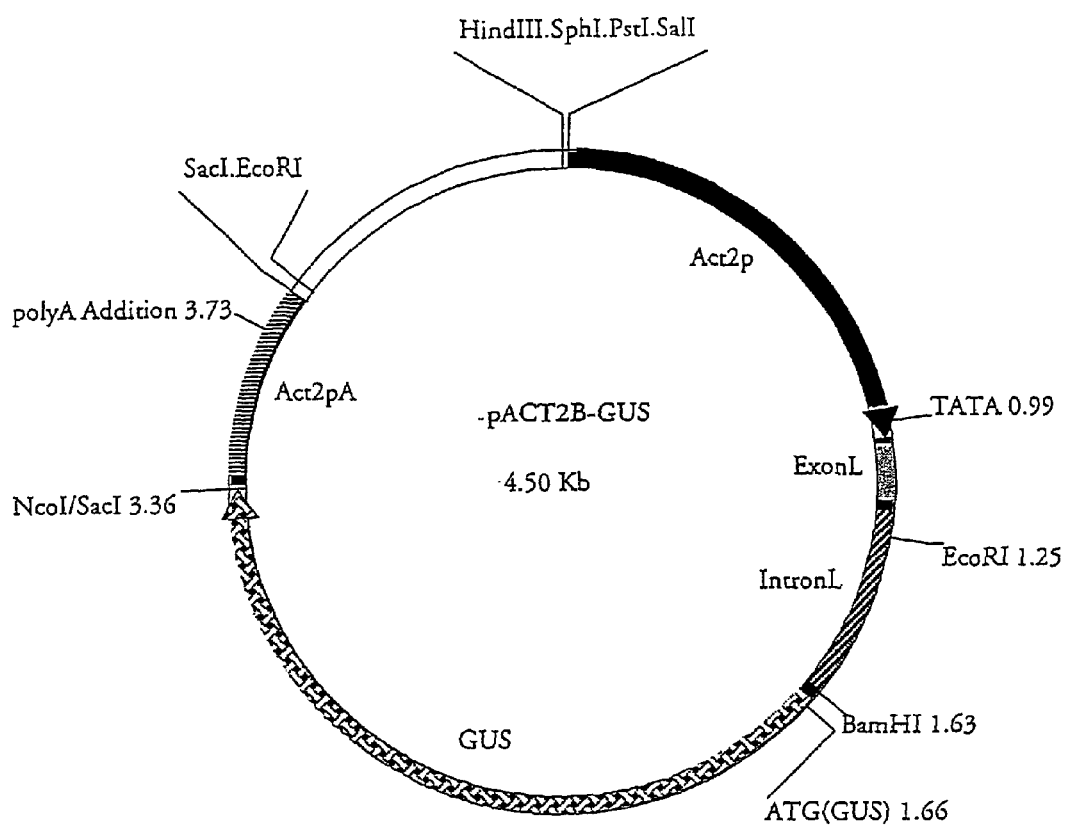
FIG. 11 illustrates pACT2B-GUS (4.5 kb). The 1.7 kb product containing the GUS coding sequence was excised from pBI101.2 (BamHI/SacI digested, blunted) and ligated to the plasmid pACT2 cut with BamHI and NcoI (blunted). See also SEQ ID NO:15.
Figure 12A:
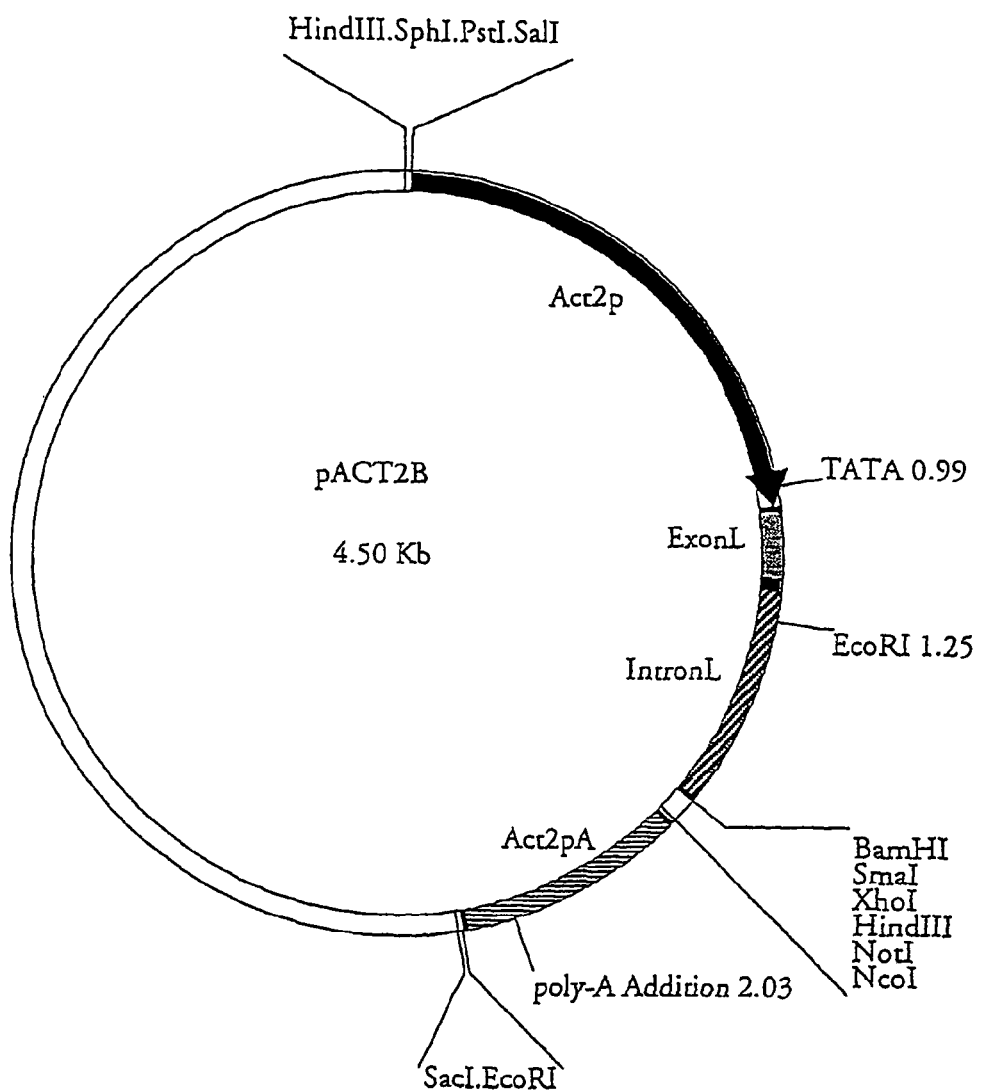
FIG. 12A illustrates pACT2B (4.5 kb). An approximately 1.5 kb 5' region (including the Act2 promoter, exon L and intron L) upstream of the ATG translation start site (ATG was replaced with a BamHI recognition site) of the actin 2 coding sequence plus multiple cloning sites and the approximately 0.5 kb PCR-amplified ACT2 promoter region was cloned into pUC19 using SalI and EcoRI digestion and subsequent ligation.
Figure 13A:
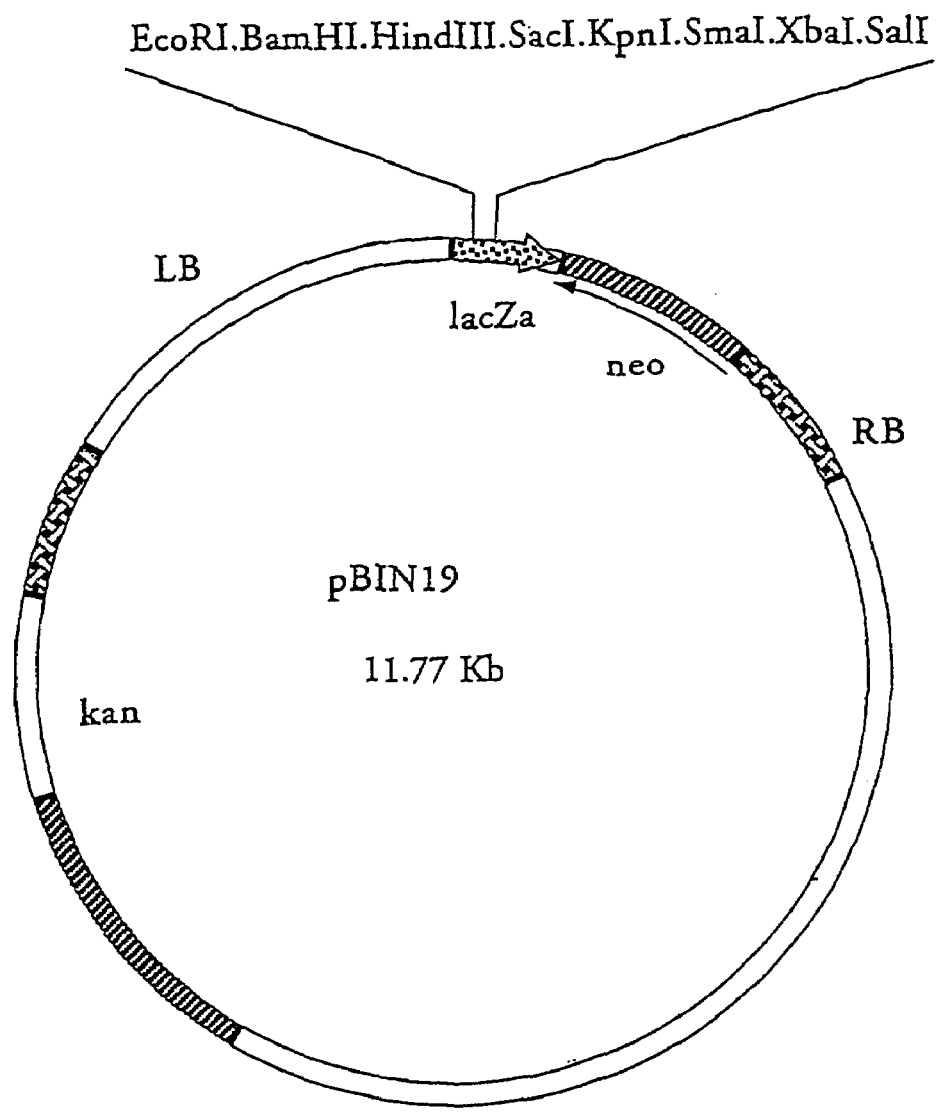
FIG. 13 shows pBIN19 (11.77 kb). See Bevan et al. (1984).
Figure 14:
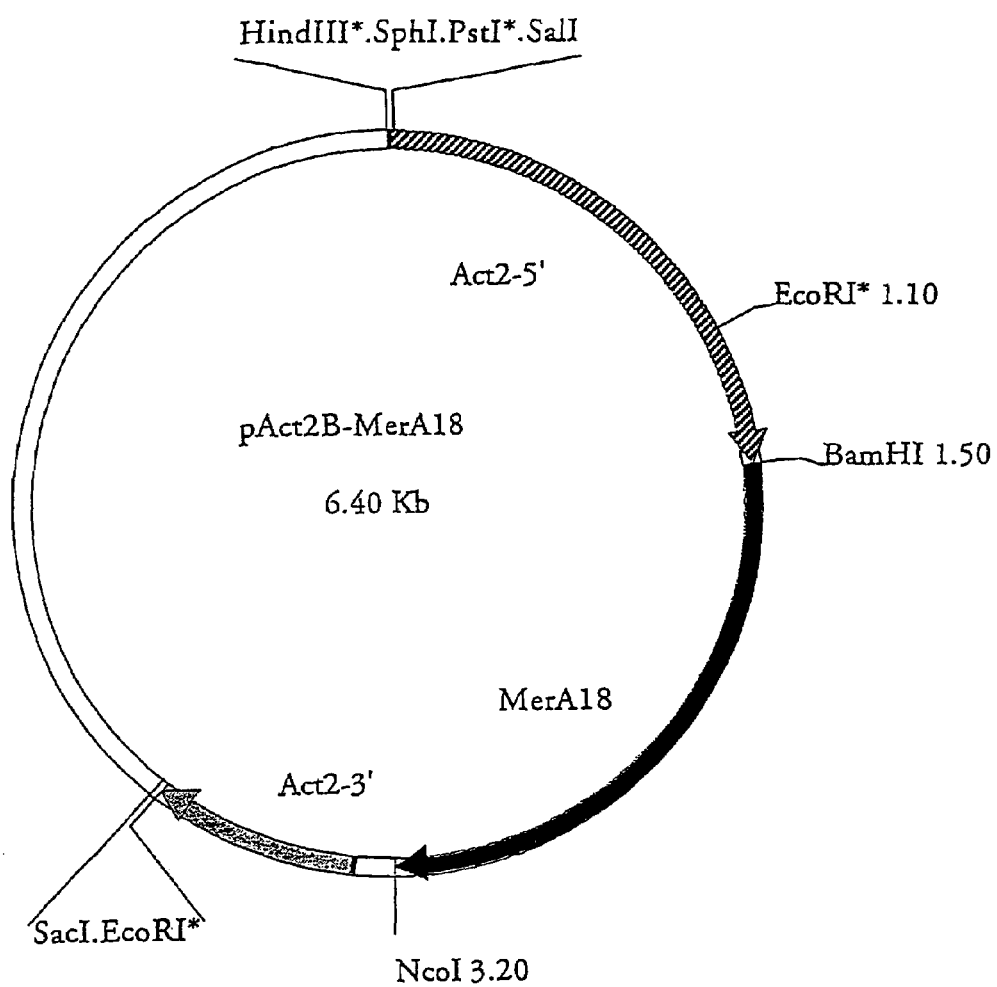
FIG. 14 shows pACT2B-MerA18 (6.4 kb). The MerA18 coding and amino acid sequences are available in U.S. Pat. No. 5,668,294.
Figure 15:
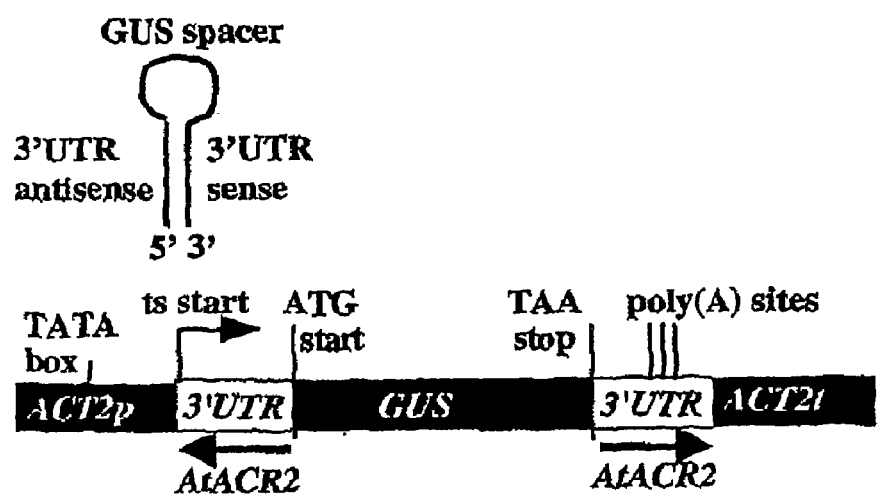
FIG. 15 shows the DNA construct for interfering RNA (RNAi) expression and the secondary structure of the RNAi for the endogenous plant arsenate reductase gene.
Figure 16:
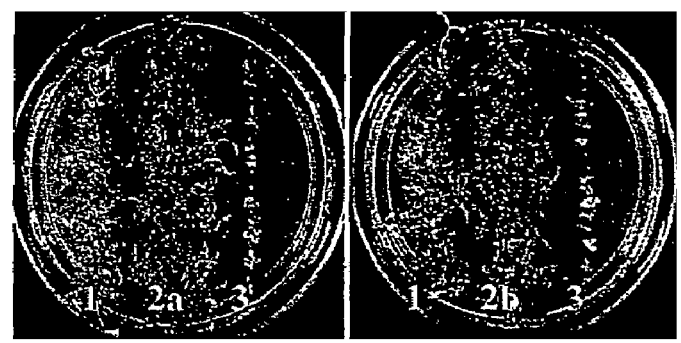
FIG. 16 shows that the expression of ECS complements the expression of ArsC to make arsenate super-resistant plants. Each arsenate-containing plate has a column of seeds from plants that constitutively express (1) ACT2p/γECS/ACT2t (left); (2a, 2b) genetic hybrid expressing both transgenes, γECS and ArsC (center); and (3) light regulated SRS1p/ArsC/ Nost (right). The hybrids (2a, 2b) are super-resistant to arsenate. Lines with γECS alone (1) are more resistant to arsenate that wild-type (not shown). Lines expressing light regulated ArsC are super sensitive to arsenate. Wild type (not shown) showed intermediate resistance between the two lines with single transgenes. The two double transgenic lines (2a, 2b) of super-resistant plants should hyperaccumulate arsenic. Seeds were germinated and grown for four weeks on 200 μM arsenate containing ½ strength MS media

Immunolabeling studies on paraformaldehyde fixed cells revealed cytoplasmic localization of γ-ECS and GS proteins as shown in FIGS. 9A-9D. MAbs to both γ-ECS (FIG. 9A) and GS (FIGS. 9B and 9C) antibodies reacted strongly, and their respective antigens were expressed in transgenic leaf cells. The fluorescence staining with mAbGS1 and mAbGS2 was uniform throughout the cytoplasm suggesting the expected distribution of soluble GS protein. In contrast, mAbECS1 exhibited punctate staining. The sublocalization of ECS suggest that the cytoplasmically expressed bacterial protein associated with small organelles or vesicles after synthesis. The mAbGS1 antibodies did not show any staining in the wild-type control plant cells (FIG. 9D). The mAbGS2 or mAbECS1 antibodies also showed no staining of plant cells (not shown). Similarly, the serum from non-immunized mice also showed no staining on transgenic leaf cells.

Several factors limit the ability to rapidly generate specific immune reagents. First, it is generally desirable to use a highly purified protein as immunogen to stimulate production of a specific antibody. Highly pure immunogens lower the chance of obtaining false positives on Western blots or misleading activities during screening of the hybridomas. Synthetic peptides can partially solve the requirement for pure protein immunogen, because they do not contain contaminating cellular antigens and can be rapidly synthesized at relatively low cost. They often stimulate the production of excellent polyclonal immune reagents (McLean et al., 1990). However, there are a few disadvantages to synthetic peptide immunogens. They must be coupled (haptenized) to carrier proteins, such as keyhole limpet hemocyanin or BSA, to fully stimulate the immune system. The need for chemical coupling to carriers has been partially circumvented, however, by the use of Multiple Antigenic Peptides (MAPs) first proposed for use in developing synthetic vaccines (Posnett et al., 1988; Tam, 1988). MAPs typically contain four (FIG. 6B) or eight redundant copies of the peptide of interest. MAPs are highly immunogenic, and in our lab nearly always give high titers of anti-MAP antibodies. We have nearly always obtained high quality anti-protein polyclonal antisera with MAPs as immunogens (Kandasamy and Meagher, 1999; Palanivelu et al., 2000) and with peptides conjugated to carrier protein as the immunogens (Condit et al., 1990; McLean et al., 1990; Kandasamy and Meagher, 1999; Palanivelu et al., 2000), when peptides were designed from mobile terminal regions of proteins (Tainer et al., 1984).

The use of synthetic peptides to produce antibodies, however, has other shortcomings that we have overcome. First, polyclonal antisera are comprised of antibodies to many target proteins and hence are inherently not as precise as mAbs. Laboratory animals eat commercial feed prepared from dried plants and undoubtedly make antibodies to some plant proteins in this material as they do to other plant-based, oral vaccines. We believe it is for this reason that many control animals already make antibodies to plant proteins before they are immunized, creating a common background problem with plant extracts. Using mAbs eliminates the high background problems of polyclonal sera. Second, synthetic peptides are not constrained by the rest of the native protein structure and fold into many novel conformations not found in the native protein. Hence, they stimulate the production of many antibodies that do not react with the whole protein and frequently fail to generate any antibody that reacts with the parent protein (McLean et al., 1990). This makes peptides less than ideal for generating and screening mAbs that react with native proteins. This is well illustrated by comparing FIGS. 7C and 7D. We believe that using N-terminally derived MAPs resembling the native terminal sequences circumvents this problem by giving a higher percentage of anti-protein antibodies. Third, short synthetic peptides containing B-cell epitopes and presented as MAPs may stimulate a good primary response, but they often do not contain T-cell epitopes necessary to stimulate a broader secondary response and production of anti-protein antibodies (Tam and Lu, 1989). This is another reason why synthetic peptide immunogens are often coupled to carrier proteins, because the carriers contain T-cell epitopes. Without wishing to be bound by any particular theory, we presume that the relatively long peptides (29-30 amino acids) used in this study included both B-cell and T-helper cell stimulating epitopes and lead to the successful production of anti-protein antibodies. Specific T-cell epitopes can be included in the peptide design (Cruz et al., 2000) if deemed advantageous.

In the study of the heterologous PC synthesizing enzymes expressed in transgenic plants, we explored one rapid method to circumvent the need for purified protein immunogens or purified protein antigens during screening of mAbs. We have shown that when MAPs comprised of long amino-terminal sequences are used as immunogens, antibodies to whole protein are seen in mouse sera and a reasonable portion of the hybridoma cell population produce antibodies to the whole protein. However, a large complement of cellular and secreted proteins are N-terminally processed as they pass into the lumen of the endoplasmic reticulum (ER) or are transported into mitochondria or chloroplasts. In *Arabidopsis* 26-43% of the 26,000 genes are predicted to encode such processed proteins (*Arabidopsis* Genome Initiative, 2000). The new N-termini generated as these proteins are processed are moderately predictable from sequence and this processing should be taken into account in peptide immunogen design (Murphy et al., 2000). However, some chemical modifications such as glycosylation in the ER may mask native epitopes, thus rendering N-terminal MAP immunogens ineffective at generating protein antibodies. In addition, we have shown that crude bacterial extracts containing the protein of interest can be used as the source of antigen during screening to identify those hybridomas producing specific anti-protein antibodies. While these assays with antigens in crude extracts have always worked in our laboratory with crude serum (Table 5), they work best and generally have lower background, when used with monoclonal antisera (FIG. 7). Using synthetic peptide immunogens and crude protein extracts expressing antigens circumvents the need for purified protein at any stage in the process of producing mAbs. Thus, it is anticipated that for most proteins, particularly those that are not drastically modified after translation, this approach will authenticate immune reactions with plant proteins that have not been purified or characterized previously.

Specific monoclonal antibody reagents were rapidly generated to all three enzymes required for phytochelatin synthesis. The antibodies reacted specifically with the proteins of interest on Western blots of crude extracts from both *E. coli* and transgenic *Arabidopsis* plants. The mAbs tested were effective histochemical reagents, reacting strongly with paraformaldehyde fixed proteins expressed in the transgenic plant cells. The combination of synthetic peptides as immunogens and recombinant proteins in crude extracts as antigens eliminated the need to purify any of the three proteins. This approach is broadly applicable beyond the specifically exemplified PC-*Arabidopsis* paradigm. It can be used in other transgenic plants for other transgenes and in genetically engineered organisms other than plants. This represents a substantial saving in time and labor in the production of mAb reagents. This streamlined method should be of general benefit to wide variety of fields including cell biology, molecular genetics, metabolic engineering, and proteomics.

It is understood that nucleic acid sequences other than that of arsC from GenBank Accession No. J02591 (nucleotides 3286-3711) (See SEQ ID NO:3 and SEQ ID NO:4 for coding sequence and deduced amino acid sequence) will function as coding sequences synonymous with the exemplified arsC coding sequence. See Table 3 for other bacterial sequences. Similarly, synonymous coding sequences can be readily substituted for the phytochelatin biosynthetic enzyme coding sequences provided herein. Nucleic acid sequences are synonymous if the amino acid sequences encoded by those nucleic acid sequences are the same. The degeneracy of the genetic code is well known to the art; i.e., for many amino acids, there is more than one nucleotide triplet which serves as the codon for the amino acid; for expression in plant cells or tissue it is desired that codon usage reflect that of plant genes and that CpG dinucleotides be kept low in frequency in the coding sequence. It is also well known in the biological arts that certain amino acid substitutions can be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Similarity between amino acid pairs has been assessed in the art in a number of ways. For example, Dayhoff et al. (1978) in *Atlas of Protein Sequence and Structure*, Vol. 5, Suppl. 3, pp. 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

A plant-expressible transcription and translation regulatory sequence can be operably linked to any promoter sequence functional in plants as understood by the skilled artisan; where a regulatory element is to be coupled to a promoter, generally a truncated (or minimal) promoter is used, for example, the truncated 35S promoter of Cauliflower Mosaic Virus, CaMV). Truncated versions of other constitutive promoters can also be used to provide CAAT and TATA-homologous regions; such promoter sequences can be derived from those of *A. tumefaciens* T-DNA genes such as nos, ocs and mas and plant virus genes such as the CaMV 19S gene or the Act2 gene of *Arabidopsis*. It will be understood that the goals of a skilled artisan will determine the choice of particular transcriptional (and translational) regulatory sequences. Translational control sequences specifically exemplified herein are the nucleotides between 8 and 13 upstream of the ATG translation start codon for bacterial signals and from nucleotides 1 to 7 upstream of the ATG translation start codon for plants. U.S. Pat. Nos. 5,668,294 and 5,874,242. (incorporated by reference herein) disclose translational control sequences suitable for plant gene expression.

A minimal promoter contains the DNA sequence signals necessary for RNA polymerase binding and initiation of transcription. For RNA polymerase II promoters the promoter is identified by a TATA-homologous sequences motif about 20 to 50 bp upstream of the transcription start site and a CAAT-homologous sequence motif about 50 to 120 bp upstream of the transcription start site. By convention, the skilled artisan often numbers the nucleotides upstream of the transcription start with increasingly large numbers extending upstream of (in the 5' direction) from the start site. Generally, transcription directed by a minimal promoter is low and does not respond either positively or negatively to environmental or developmental signals in plant tissue. An exemplary minimal promoter suitable for use in plants is the truncated CaMV 35S promoter, which contains the regions from −90 to +8 of the 35S gene. Where a minimal promoter is used, it is desired that for high levels of gene expression, transcription regulatory sequences which upregulate the levels of gene expression be operably linked thereto. Such quantitative regulatory sequences are exemplified by transcription enhancing regulatory sequences such as enhancers.

Operably linking transcription and translation regulatory sequences upstream of a promoter functional in a plant cell allows the expression of the cadmium resistance (ArsC protein) coding sequence operably fused just downstream of the promoter, and the skilled artisan understands spacing requirements and ribosome binding site requirements for translational expression of the coding sequence. The cadmium resistance coding sequence preferably encodes the ArsC protein of R773, as exemplified by the amino acid sequence in Table 2 and GenBank Accession No. J02591. Further improvement and broader resistance, especially for the thio-reactive metals, can be achieved by also introducing at least one plant-expressible phytochelatin biosynthetic enzyme coding sequence to be expressed in the same plant cells or plants.

In plants, the constitutive plant-expressible transcription and translation regulatory element effects the expression of a downstream plant-expressible metal resistance coding sequence. Constitutive promoters include the Act2 promoter of *Arabidopsis* and the 35S and 19S promoters from cauliflower mosaic virus. Data are presented for cadmium resistance in *Arabidopsis thaliana* genetically engineered to contain and express a plant-expressible arsenate reductase coding sequence, in particular, that encoding the ArsC of R773. Similar results are obtained in other plants, including monocots, dicots and gymnosperms, after stable transformation, as for the *Arabidopsis thaliana* experiments described herein.

Coding sequences suitable for expression in a plant are operably linked downstream of a constitutive or a regulated promoter construct which is functional in a plant. Transgenic plants can be constructed using the chimeric gene consisting essentially of the promoter, any additional transcription enhancing sequences, and the desired cadmium resistance coding sequence and/or at least one phytochelatin biosynthetic enzyme coding sequence and including the necessary sequence signals for its translation.

Additionally, or alternatively, induction of the regulated construct can be induced, for example, by treating the transgenic plant or tissue with an inducer suitable for regulating expression of the plant-expressible ArsC coding sequences of the present invention. The expression of the cadmium resistance (ArsC) coding sequence can also be regulated by tissue specific or light regulated transcription regulatory sequences. This disclosure specifically exemplifies the use of the SRS1 transcription regulatory sequence from soybean, but the chlorophyll A/B binding protein light-inducible transcription regulatory sequences (Castresana et al., 1988; McGrath et al., 1992) can also be used, for example.

The bacterial arsC coding sequence was placed under control of the lac operon promoter to separate it from its normal arsenic inducible expression (FIG. 1). To demonstrate that this clone made an active arsenate reductase enzyme, metal ion-sensitivity filter disk assays were performed to compare the growth of *E. coli* strains with and without the pNA1 construct in the presence of arsenate and other metal ions. The sizes of the zones of sensitivity around disks containing arsenate and cadmium ions are shown for various strains in Table 1. As expected, the AW10 cells were significantly more resistant to arsenate when transformed with pNA1 (Table 1). These results demonstrate that arsC encoded a fully functional arsenate reductase in *E. coli*.

Figure 2:
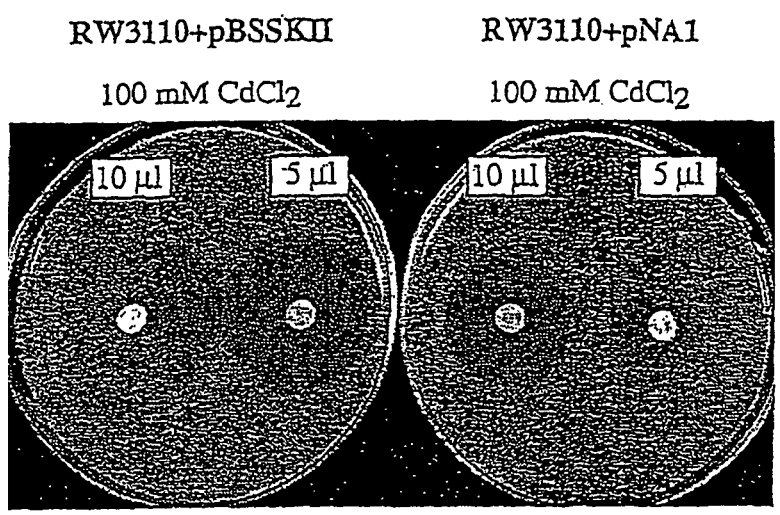
FIG. 2 demonstrates the increase in resistance of *E. coli* to cadmium chloride due to the expression of the ArsC protein (as expressed by pNA1; the control cells carry the pBSSKII vector without a resistance insert).

The effect of arsC gene on the resistance to other metal ions was tested in parental strains AW10 and RW3110. The AW10 strain failed to respond to Cd and showed no difference in cell growth with or without pNA1, whereas the RW3110 strain without pNA1 plasmid was supersensitive to Cd as evidenced by a large ring of growth inhibition ($Cd^{ss}$, 47mm). This strain has no Cd(II) transport system and therefore is sensitive to Cd. When the supersensitive strain contained the pNA1 plasmid, it showed a significant protection against Cd, and the zone of growth inhibition was smaller (RW3110+pNA1, 23 mm) (FIG. 2). The data clearly indicate that arsenate reductase provides at least partial resistance to Cd(II) in *E. coli*.

The arsC sequence from pNA1 was subcloned under the control of the soybean plant ribulose biphosphate carboxylase (rubisco) small subunit promoter SRS1 and the 3' nos terminator in pBluescript. This coding sequence and promoter were previously shown to be strongly transcriptionally induced in leaves by light (Shirley et al., 1987). Expression directed by this promoter is very low in roots. The entire chimeric gene including the SRS1 promoter, the arsC coding sequence, and the 3' nos transcription terminator sequence, was subcloned into the plant expression T-DNA binary vector pBIN19, which has the selectable kanamycin-resistance marker (NPTII). *A. thaliana* was transformed using vacuum infiltration technology, and the T1 generation seeds were screened for kanamycin resistance. Five kanamycin-resistant *Arabidopsis* lines were obtained after transformation with the pBIN/arsC construct and were designated arsC/N2, arsC/N7, arsC/N8, arsC/N9 and arsC/N10. Homozygous T2 lines were used for subsequent experiments. These transgenic plants did not show any phenotypic differences from the untransformed *Arabidopsis* plants except for their metal resistance phenotype.

Antibodies produced against the bacterial ArsC protein were used to analyze the ArsC expression in the transgenic lines at the protein level. Leaf extracts from all the kanamycin resistant transgenic lines tested (arsC/N2, arsC/N7, arsC/N8, arsC/N9 and arsC/N10) showed intense bands at 14 kDa, slightly lower than the expected size of 16 kDa of the *E. coli* enzyme (FIG. 3A). No band was detected in the wild type extracts. Transgenic lines arsC/N2 and arsC/N7 showed lower expression of ArsC protein than lines arsC/N8, arsC/N9, and arsC/N10 (FIG. 3A). Expression of the chimeric arsC gene is tightly regulated in leaves by the SRS1 promoter. For further experiments, one low level expression line arsC/N2 and two high level expression lines arsC/N8, and. arsC/N9 were used.

Figure 4A:
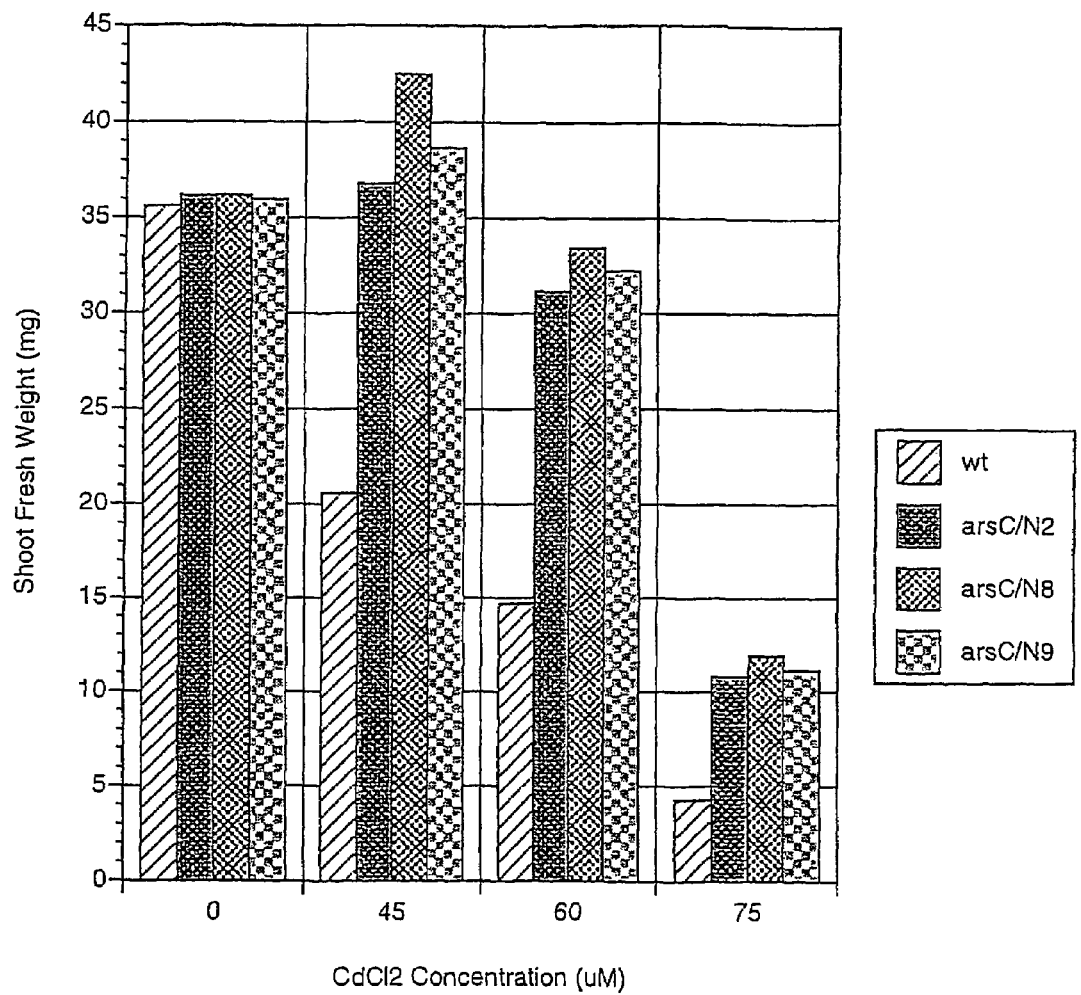
FIG. 4A graphically illustrates the effects of cadmium chloride exposure in wild-type *Arabidopsis* plants and in transgenic lines arsC/N2, arsC/N8 and arsC/N9 and wild-type *Arabidopsis* sown on agar media containing 0, 45, 60 and 75 μM $CdCl_2$. After seed germination, the plates were oriented in a vertical position in order to harvest shoot and root separately.
Figure 4B:
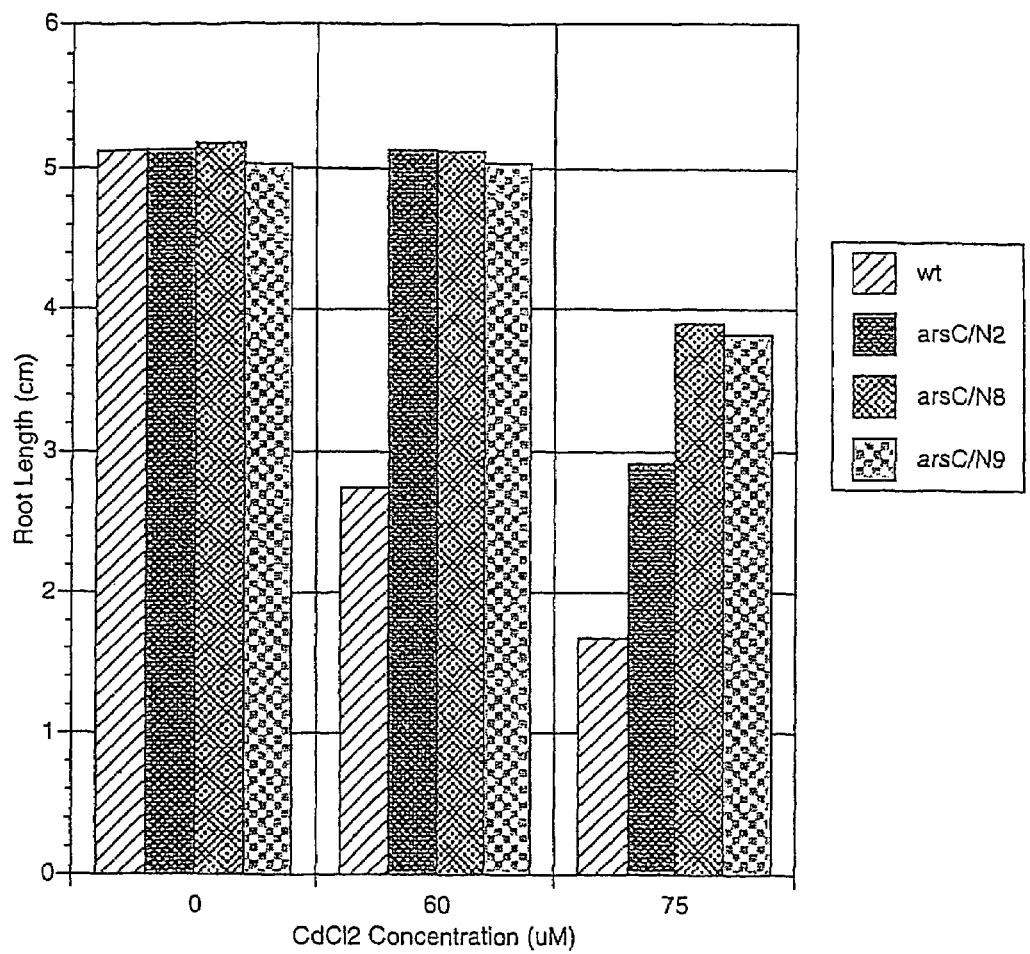
FIG. 4B shows the effects of cadmium chloride exposure on root length in the wild-type *Arabidopsis* plants and in transgenic lines arsC/N2, arsC/N8 and arsC/N9. After 4 weeks, root lengths of seedlings were measured and photographed, and shoots and roots were harvested separately. At 60 and 75 μM $CdCl_2$, ArsC transgenic seedlings had approximately 50% longer roots than the wild-type seedlings. The wild-type roots had few lateral branches and root hairs as compared to roots of ArsC transgenic plants. On control medium and media with up to 45 μM Cd, the ArsC transgenic and wild-type seedlings showed no difference in root length.

The seeds of transgenic lines arsC/N2, arsC/N8 and arsC/N9.and wild-type *Arabidopsis* were sown on agar media containing 0, 45, 60 and 75 $\mu$M $CdCl_2$. After seed germination, the plates were oriented in a vertical position in order to harvest shoots and roots separately. After 4 weeks, root lengths of seedlings were measured and photographed, and shoots and roots were harvested separately. At 60 and 75 $\mu$M $CdCl_2$, ArsC transgenic seedlings had approximately 50% longer roots than the wild-type seedlings (FIG. 4B). The wild-type root had few lateral branches and root hairs as compared to roots of ArsC transgenic plants. On control medium and media with up to 45 $\mu$M Cd, the ArsC transgenic and wild-type seedlings showed no difference in root length.

Figure 5:
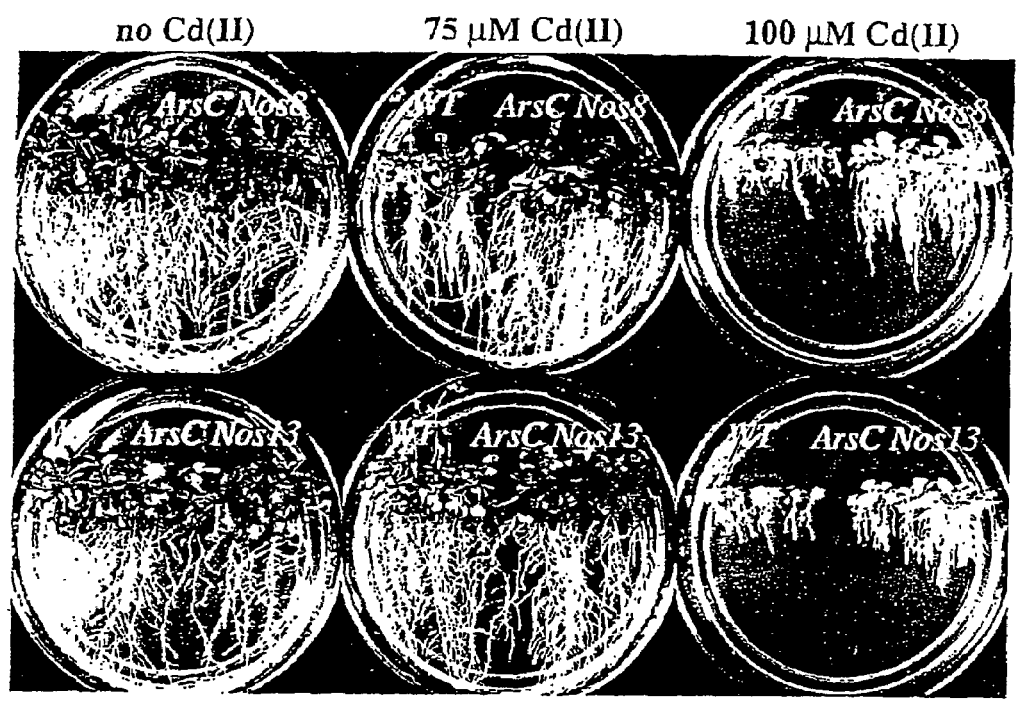
FIG. 5 presents photographs of wild-type *Arabidopsis* and three transgenic plants (35S/arsC/Nos8 or 35S/arsC/Nos13) grown for 4 weeks in the presence of 0.75 μM $CdCl_2$ or 100 μM $CdCl_2$ in agar medium.

After 4 weeks of growth on medium containing $CdCl_2$, transgenic seedlings of lines arsC/N2, arsC/N8 and arsC/N9 had attained a 2-3 fold higher fresh weight than the wild type (FIG. 4B). At 45 $\mu$M $CdCl_2$, transgenic lines arsC/N8 and arsC/N9 grew slightly better and had broader leaves as compared to their growth on media without $CdCl_2$. The ArsC transgenic plants suffered less growth inhibition than wild type plants at higher Cd concentrations (FIG. 5). Wild type plants had spindly shoots, lanceolate leaves and relatively fewer lateral roots. Also, these plants showed early flowering apparently brought on by toxic stress. At 75 $\mu$M Cd, wild-type plants were severely stressed and nearly died under these conditions. These plants had abnormal phenotypes and turned yellow with a pinkish tinge. In contrast, transgenic lines were much less affected, grew about 3-fold larger and did not die (FIG. 5). Transgenic *Arabidopsis* plants expressing the ArsC protein had a clear advantage over control plants at these concentrations of $CdCl_2$. The growth of arsC/N2 plants was less vigorous on Cd than arsC/N8 and arsC/N9 plants, in concordance with its lower ArsC expression levels (FIG. 3A). There was no significant difference in fresh weight between transgenic lines and wild type when grown on media not supplemented with $CdCl_2$.

In order to study whether the ArsC transgenic plants accumulate more Cd in shoots in accordance with the tolerance level, we extracted total Cd from transgenic and wild type: shoot tissues by acid digestion as described below. No significant difference in the accumulation level of Cd was observed between shoots of transgenic and wild type plants.

The ArsC plants of the present invention are useful in the revegetation of soils contaminated with divalent cadmium cations, and they are also useful for removing and reducing cadmium cations from water, wastewater, aqueous environments and soils contaminated with cadmium. The choice of plants into which the arsC is introduced is determined by the climate, soil and moisture conditions of the site where the plants are to be grown, as well understood by those of ordinary skill in the art. Desirably, te plant also expresses at least one phytochelatin biosynthetic enzyme coding sequence, e.g., γ-ECS, PS and/or GS.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment and subsequent selection and regeneration (see Davey et al. (1989) *Plant Mol. Biol.* 13:275; Walden and Schell (1990) *Eur. J. Biochem.* 192:563; Joersbo and Burnstedt (1991) *Physiol. Plant.* 81:256; Potrykus (1991) *Annu. Rev. Plant Physiol. Plant Mol. Biol.* 42:205; Gasser and Fraley (1989) *Sci.* 244:1293; Leemans (1993) *Bio/Technology.* 11:522; Beck et al. (1993) *Bio/Technology.* 11:1524; Koziel et al. (1993) *Bio/Technology.* 11:194; Vasil et al. (1993) *Bio/Technology.* 11:1533). Techniques are well known to the art for the introduction of DNA into monocots as well as dicots, as are the techniques for culturing such plant tissues and regenerating those tissues. Monocots which have been successfully transformed and regenerated include wheat, corn, rye, rice and asparagus. For efficient regeneration of transgenic plants, it is desired that the plant tissue used in the transformation possess a high capacity to produce shoots. For example, Aspen stem sections have good regeneration capacity. [Devillard, C. III et al. (1992) *C. R. Acad Sci. Ser. VIE* 314:291-298K; Nilsson et al. (1992) *Transgenic Research* 1:209-220; Tsai et al. (1994) *Plant Cell Rep.* 14:94-97] Poplars have been successfully transformed [Wilde et al. (1992) *Plant Physiol.* 98:114-120] and regenerated as have cottonwoods. The latter trees are useful for phytoremediation of contaminated environments, in part, because they grow rapidly.

Techniques and agents for introducing and selecting for the presence of heterologous DNA in plant cells and/or tissue are well-known. Genetic markers allowing for the selection of heterologous DNA in plant cells are well-known, e.g., genes carrying resistance to an antibiotic such as kanamycin, hygromycin, gentamycin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e., the chimeric gene containing nopaline synthetase promoter, Tn5 neomycin phosphotransferase II and nopaline synthetase 3' non-translated region described by Rogers et al., *Methods for Plant Molecular Biology*, A. Weissbach and H. Weissbach, eds., Academic Press, Inc., San Diego, Calif. (1988).

Other techniques for genetically engineering plant tissue to contain an expression cassette comprising a promoter and associated transcription regulatory sequences fused to the metal resistance coding sequence and optionally containing a transcription termination region are to be integrated into the plant cell genome by electroporation, co-cultivation, microinjection, particle bombardment and other techniques known to the art. The metal resistance plant expression cassette further contains a marker allowing selection of the expression cassette in the plant cell, e.g., genes carrying resistance to an antibiotic such as kanamycin, hygromycin, gentamycin, or bleomycin. The marker allows for selection of successfully transformed plant cells growing in the medium containing certain antibiotics because they will carry the expression cassette with resistance gene to the antibiotic.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g., calcium phosphate coprecipitation, viral vectors, and other techniques practiced in the art. Suitable plant transformation vectors include those derived from a Ti plasmid of *Agrobacterium tumefaciens*, such as those disclosed by Herrera-Estrella (1983), Bevan (1983), Klee (1985) and EPO publication 120,516 (Schilperoort et al.). In addition to plant transformation vectors derived from the Ti or root-inducing (Ri) plasmids of *Agrobacterium*, alternative methods can be used to insert the DNA constructs of this invention into plant cells.

The choice of vector in which the DNA of interest is operatively linked depends directly, as is well known in the at, on the functional properties desired, e.g., replication, protein expression, and the host cell to be transformed, these being limitations inherent in the art of constructing recombinant DNA molecules. The vector desirably includes a prokaryotic replicon, i.e., a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT and pBS available from Stratagene (La Jolla, Calif.). A vector of the present invention may also be a Lambda phage vector including those Lambda vectors described in *Molecular Cloning: A Laboratory Manual, Second Edition*, Maniatis et al., eds., Cold Spring Harbor Press (1989) and the Lambda ZAP vectors available from Stratagene (La Jolla, Calif.). Other exemplary vectors include pCMU [Nilsson et al. (1989) *Cell* 58:707]. Other appropriate vectors may also be synthesized, according to known methods; for example, vectors pCMU/$K^b$ and pCMUII used in various applications herein are modifications of pCMUIV (Nilson et al., supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens* described by Rogers et al. (1987) *Meth. in Enzymol.* 153:253-277, and several other expression vector systems known to function in plants. See for example, Verma et al., No. WO87/00551; Cocking and Davey (1987) *Science* 236:1259-1262.

A transgenic plant can be produced by any means known to the art, including but not limited to *Agrobacterium tumefaciens*-mediated DNA transfer, preferably with a disarmed T-DNA vector, electroporation, direct DNA transfer, and particle bombardment (See Davey et al. (1989) *Plant Mol. Biol.* 13:275; Walden and Schell (1990) *Eur. J. Biochem.* 192:563;

Joersbo and Burnstedt (1991) *Physiol Plant.* 81:256; Potrykus (1991) *Annu. Rev. Plant Physiol. Plant Mol. Biol.* 42:205; Gasser and Fraley (1989) *Science* 244:1293; Leemans (1993) *Bio/Technology.* 11:522; Beck et al. (1993) *Bio/Technology.* 11:1524; Koziel et al. (1993) *Bio/Technology.* 11:194; and Vasil et al. (1993) *Bio/Technology.* 11:1533.). Techniques are well-known to the art for the introduction of DNA into monocots as well as dicots, as are the techniques for culturing such plant tissues and regenerating those tissues.

Polymerase Chain Reaction (PCR) is a repetitive, enzymatic, primed synthesis of a nucleic acid sequence. This procedure is well known and commonly used by those skilled in this art [see Mullis, U.S. Pat. Nos. 4,683,195, 4,683,202, and 4,800,159; Saiki et al. (1985) *Science* 230:1350-1354]. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Bal31 exonuclease can be conveniently used for time-controlled limited digestion of DNA. See, for example, Maniatis (1982) *Molecular Cloning: A Laboratory Manual*, Cold Spring Harbor Laboratory, New York, pages 135-139, incorporated herein by reference. See also Wei et al. (1983 *J. Biol. Chem.* 258:13006-13512. By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original ACT2 or SRS1 sequences. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3):349-59; Shortle, D, DiMaio, D., and Nathans, D. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain promoter activity and also appropriate constitutive or regulated transcription of downstream sequence, and similarly, phytochelatin biosynthetic enzyme (PCS and γECS) or arsenate reductase coding sequences functionally equivalent to those specifically exemplified can also be isolated and identified using techniques well known to those of ordinary skill in the art.

Monoclonal or polyclonal antibodies, preferably monoclonal, specifically reacting with a protein of interest can be made by methods well known in the art. See, e.g., Harlow and Lane (1988) *Antibodies: A Laboratory Manual*, Cold Spring Harbor Laboratories; Goding (1986) *Monoclonal Antibodies: Principles and Practice,* 2d ed., Academic Press, New York; and Ausubel et al. (1993) *Current Protocols in Molecular Biology*, Wiley Interscience/Greene Publishing, New York, N.Y.

The following examples use many techniques well known and accessible to those skilled in the arts of molecular biology, in the manipulation of recombinant DNA in plant tissue and in the culture and regeneration of transgenic plants. Enzymes are obtained from commercial sources and are used according to the vendors' recommendations or other variations known to the art Reagents, buffers and culture conditions are also known to the art. References providing standard molecular biological procedures include Sambrook et al. (1989) *Molecular Cloning*, second edition, Cold Spring Harbor Laboratory, Plainview, N.Y., R. Wu (ed.) (1993) *Methods in Enzymology* 218, Wu et al. (eds.) *Methods in Enzymology* 100, 101, Glover (ed.) (1985) *DNA Cloning*, Vols. I and II, IRL Press, Oxford, UK; and Hames and Higgins (eds.) (1985) *Nucleic Acid Hybridization*, IRL Press, Oxford, UK. References related to the manipulation and transformation of plant tissue include R. A. Dixon (ed.) (1985) *Plant Cell Culture: A Practical Approach*, IRL Press, Oxford, UK; Schuler and Zielinski (1989) *Methods in Plant Molecular Biology*, Academic Press, San Diego, Calif.; Weissbach and Weissbach (eds.) (1988) *Methods for Plant Molecular Biology*, Academic Press, San Diego, Calif.; I. Potrykus (1991) *Ann. Rev. Plant Physiol. Plant Mol. Biol.* 42:205; Weising et al. (1988) *Annu. Rev. Genet.* 22:421, van Wordragen et al. (1992) *Plant Mol. Biol. Rep.* 19:12, Davey et al. (1989) *Plant Mol. Biol.* 13:273, Walden and Schell (1990) *Eur. J. Biochem.* 192:563, Joersbo and Brunstedt (1991) *Physiol. Plant.* 81:256 and references cited in those references. Abbreviations and nomenclature, where employed, are deemed standard in the filed and are commonly used in professional journals such as those cited herein.

All references cited in the present application are expressly incorporated by reference herein to the extent that they are not inconsistent with the present disclosure.

The following examples are provided for illustrative proposes and are not intended to limit the scope of the invention as claimed herein. Any variations in the exemplified compositions and methods, which occur to the skilled artisan, are intended to fall within the scope of the present invention.

EXAMPLES

Example 1

Strains and Plasmids

*Escherichia coli* strain AW10 contains plasmid pArsAB200 which has the arsA and arsB genes, *E. coli* JM109 contains plasmid pAlter-C which bears the arsC gene, and *E. coli* RW3110 is a strain in which a Zn (II)/Cd (II) pump gene termed as zntA is knocked out, as described previously (Carlin et al., 1995; Rensing et al., 1997). The pBluescriptSK (−)

plasmid (Stratagene, La Jolla, Calif.) and promoterless binary vector pBIN19 (Clontech, Palo Alto, Calif.), designed for expressing genes under promoter of interest by *Agrobacterium*-mediated transformations, were obtained commercially.

Example 2

Reconstruction of arsC for Plant Expression

The 141-codon arsC gene was amplified by PCR using long synthetic primers that modified the arsC flanking sequences as shown in FIG. 1A. The sense primer, ArsC1S consisted of the 56 nt sequence 5'-TACGTCGGATCCGAAT-TCGTCGACTAAGGAGGAGCCACAATGAG-CAACATCACTAT-3' (SEQ ID NO:1) and contained BamHI, EcoRI and SAII cloning sites, a TAA stop codon to end the translation of an upstream β-galactosidase fusion protein in *E. coli*, a GGAGGA bacterial translation signal to improve expression in *E. coli*, an AGCCACA consensus sequence for plant translation (Heidecker and Menning, 1986), an ATG start codon and the first 17nt of the arsC coding sequence to prime the forward PCR reaction (Rugh et al., 1996). The antisense primer, ArsC141A, had the 40 nt sequence 5'-TAG-GTCGGATCCGAATTCAAGCTTAT-TATTTCAGCCGTTT-3' (SEQ ID NO:2), with HindIII, EcoRI and BamHI cloning sites and anticodons to the last 4 arsC codons to prime the reverse PCR reaction. PCR was carried out for 45 cycles with denaturing, annealing and extending temperatures and times of 94° C. for 1 min, 48° C. for 1 min, and 72° C. for 1 min. The plasmid pAlterC (10 ng) bearing the arsC gene was used as template. *E. coli* containing the plasmid pR773 which contains the arsA, arsB, and arsC genes, and the AW10 strain containing arsA and arsB but lacking the arsC gene were used as positive and negative controls, respectively, for the PCR reaction. The amplified fragment, arsC, was cleaved in the flanking BamHI and HindIII sites and ligated into the multilinker of pBluescript SK (−) to make plasmid pNA1 as shown in FIG. 1. The pNA1 construct was electroporated into the AW10 and RW3110 strains of *E. coli*. The same *E. coli* strains were also transformed with the pBluescript SK (−) plasmid lacking an insertion to serve as a negative control in metal ion-sensitivity filter disk assays.

Figure 3:
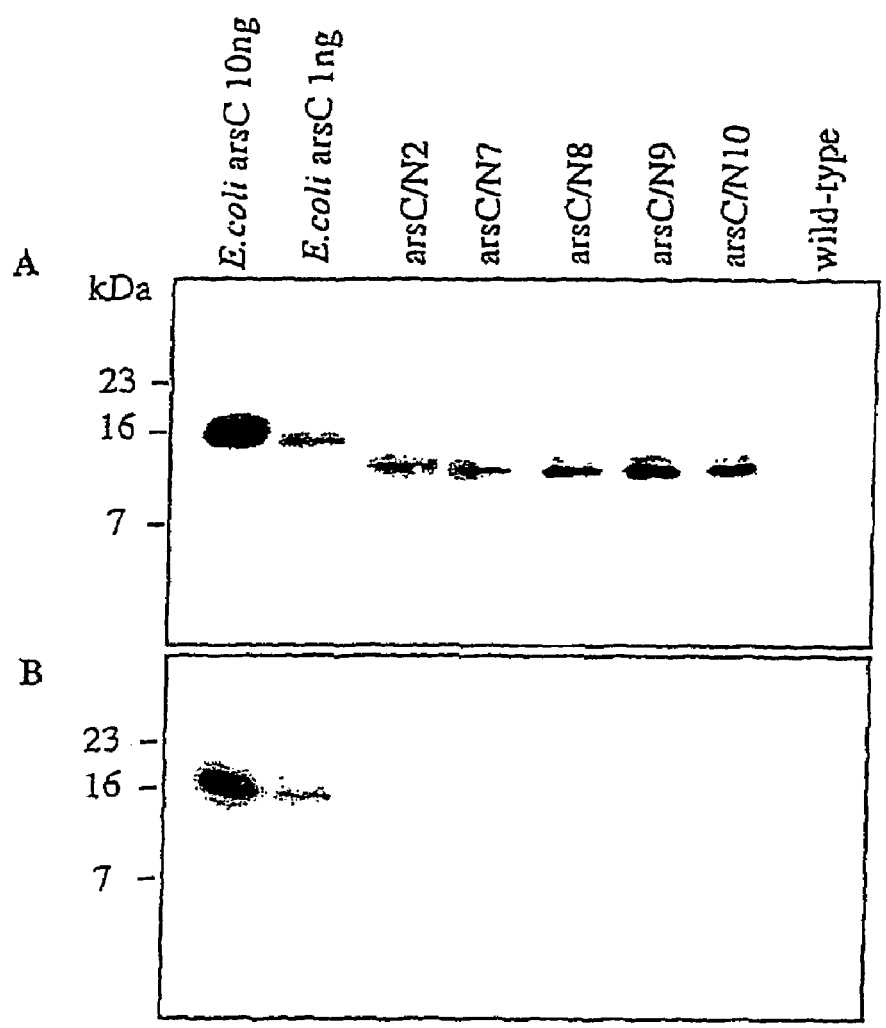
FIG. 3 illustrates the results of Western blots using antibodies produced against the bacterial ArsC protein and leaf extracts from kanamycin resistant transgenic plant lines (arsC/N2, arsC/N7, arsC/N8, arsC/N9 and arsC/N10). These extracts showed intense bands at 14 kDa, slightly lower than the expected size of 16 kDa of the *E. coli* enzyme. No immunoreactive band was detected in the wild type extracts. Expression of the chimeric arsC gene is tightly regulated in leaves by the SRS1 promoter.

For plant expression, the arsC sequence was subcloned under the regulatory control of the 1.5 kb rubisco small subunit SRS1 promoter (see, e.g., Shirley et al., 1987; Shirley et al., 1990; and GenBank Accession No. X58684) and the nopaline synthase (nos) 3' terminator by using BamHI and XhoI sites in the Bluescript multilinker to create pSRSP/arsC/nos (FIG. 1). The entire cassette containing the SRS1 promoter, arsC coding sequence and nos 3' terminator, was subcloned into pBIN19 (Bevan, 1984) by using 5' SacI and 3' XhoI/SmaI blunt ends to create pBIN/arsC (FIG. 3).

Example 3

Disk Sensitivity Assays

Sodium arsenate and cadmium chloride (Sigma Chemical Co., St. Louis, Mo.) solutions were prepared in sterile water. Because of the extreme toxicity membrane permeability of these chemicals, dry stocks, and stock solutions were handled using protective clothing, eye protection, and double layers of gloves. All metal ion-sensitivity filter disk assays were performed in the presence of ampicillin to maintain the pBSSKII plasmid, as described in Rugh et al., 1996. The data reported are the average results of three replicates. Approximately $2\times10^8$ cells carrying the lac-regulated arsC sequence were plated in top agar on LB medium containing IPTG (1 mM final concentration) and appropriate antibiotics. 5 or 10 μl aliquots of metal ion solution (100 mM $CdCl_2$ or 250 mM $As_2O_5$) was pipetted onto 6 mm diameter sterile 3 mm Whatman paper disks, which were placed on solidified top agar containing the strains of interest. The plates were incubated overnight at 37° C., and the zones of growth inhibition were then measured.

Example 4

Construction of Transgenic Plants

Plasmid pBIN/arsC, carrying the chimeric arsC gene (SRS1P:arsC:nos3'), was electroporated into cells of the C58 *Agrobacterium tumefaciens* strain (GIBCO/BRL, Gaithersburg, Md.). Transformants were verified by using Southern blotting and grown up in YEP medium (10 g/liter Bacto peptone (Difco, Detroit, Mich.)/10 g/liter yeast extract/5 g/liter NaCl) in the presence of streptomycin and kanamycin to maintain the T-DNA and pBIN19 plasmids, respectively. Wild-type *A. thaliana* (ecotype Columbia) tissue was transformed with this *A. tumefaciens* strain using the vacuum infiltration procedure (Bent et al., 1994).

Example 5

Germination, Growth and Metal Analysis

Wild-type (columbia) and transgenic ArsC *Arabidopsis* seeds were sterilized by rinsing in 70% ethanol for 1 minutes, then in 30% Clorox (Clorox is a trademark of The Clorox Company, and it is 5.25% sodium hypochlorite) for 30 minutes with frequent shaking, followed by 4 rinses in sterile water. Sterilized seeds were sown on one half strength MS medium containing 30 g/liter sucrose, 0.8% Phytagar (purified agar) (GIBCO/BRL, Invitrogen, Carlsbad, Calif.), pH 5.7 and different concentrations of $CdCl_2$ (0, 45, 60 and 75 μM). The seeds plated on media were vernalized at 4° C. for at least 25 h. Seedlings were grown at 22° C. with a daily regime of 16 h light/8 h darkness. Shoots and roots of four-week old individual seedlings were harvested separately, rinsed with sterile water, dry-blotted, weighed and root length was measured. Harvested tissues were frozen in liquid nitrogen, lyophilized and stored at −80° C. until needed.

Samples of 0.5 g fresh weight of each line were dried at 70° C. for 3 days, ground in 15 ml tubes with a homogenizer and digested for 48 h in 10 ml of 1:3 (v/v) of 37% HCl and 65% $HNO_3$ in EPA vials closed with Teflon caps. Extracts were centrifuged at 12,000×g for 10 minutes, and the liquid fractions were analyzed for Cd content by inductively coupled plasma mass spectroscopy (ICP-MS). Standards (National Institute of Standards and Technology) and blanks were run with all samples for quality control.

Example 6

Sodium Dodecyl Sulfate-Polyacrylamide Gel Electrophoresis and Western Blots

Polyclonal anti-ArsC antibodies prepared as described previously (Rosen et al., 1991) were used for quantitative Western analysis. Leaves and root of transgenic and control *Arabidopsis* plants were ground in liquid nitrogen and extracted in a buffer containing 3 mM EDTA/10 mM $MgCl_2$/10 mM NaCl/25 mM Tris-HCl, pH 7.5/1 mM phenylmethylsulfonyl fluoride. The homogenate was then centrifuged at 4° C., 12000×g for 15 minutes. After measurement of total protein concentration (Bradford, 1976), 10 µg of protein from each sample was denatured by adding an equal volume of 2×SDS sample buffer and boiling for 5 min, and then the proteins were size-separated using SDS/12% PAGE (Laemmli, 1970). The resolved protein was electroblotted onto an Immobilon-P (polyvinylidene fluoride) membrane (Millipore, Beverly, Mass.). The anti-ArsC antibody was incubated with membrane-bound plant protein for 90 min after blocking for 1 h with 5% dry milk/10% goat serum (Sigma Chemical Co., St. Louis, Mo.) TBS-T buffer. Anti-rabbit Ig horseradish peroxidase-linked whole antibody from donkey was used as a secondary antibody.

In PC expression experiments, the bacterial and plant protein extracts were separated on 10% SDS-PAGE gels (Laemmli, 1970) and Western membrane imprints were prepared as described in Bizily et al. (1999). The membrane was blocked for 2 h in TBST (10 mM Tris-HCl pH 7.5, 150 mM NaCl, 0.05% Tween 20) containing 5% dry milk and 20% goat serum and probed with the primary antibody in the blocking buffer for 2 h at room temperature. Either the hybridoma cell supernatant was used directly at 0.1-0.2 ml/ml or the purified mAbs were used at 1 µg/ml final concentration (~1:2000 dil). After washing (3×5 min), the blot was incubated with horseradish peroxidase conjugated, anti-mouse, secondary antibody (Amersham) at 1:2000 dilution in blocking buffer for 30 min. After washing again in TBST (3×8 min), the blots were treated with the ECL detection solution (Amersham), and exposed for 1-5 min to x-ray film (Amersham, Hyperfilm).

After resolution of the crude bacterial or plant protein extracts by SDS-PAGE, approximate protein expression levels in the gels were compared by Coomassie staining to make sure protein levels were equivalent for ELISAs or Western blots. The levels of bacterially expressed γ-ECS from a pET15b vector and GS expressed from a pBluescript KS(II) vector were detectable over and above the complement of resident bacterial proteins (not shown). Bands of PS protein were not visible over the complement of E. coli proteins when the PS gene was expressed from either vector suggesting that PS synthesis was very inefficient. Regardless of these low levels, crude extracts with PS synthesized from the pET15b vector was used in subsequent studies. ELISAs and Western blots later confirmed the presence of PS protein.

Example 7

Production of Monoclonal Antibodies(mAbs)

Monoclonal antibodies were prepared essentially as described in Kohler and Milstein (1975) with the following modifications. Multiple antigenic peptides (MAPs) were synthesized in an Advanced Chemtech MPS350 peptide synthesizer (Louisville, Ky.). Three six-week-old female mice were given multiple injections of MAP immunogens (Tam, 1988) at three-week intervals. The first injection (100 µg) was given intraperitoneally and subcutaneously with the immunogen emulsified with complete Freund's adjuvant. Three to five booster injections of the MAP (100 µg) were given intraperitoneally mixed with incomplete Freund's adjuvant. Seven days after the third and subsequent injections, a test bleed was performed and serum antibody levels were evaluated by ELISA (see below). Mice showing the highest antibody titers were selected and again injected intraperitoneally with 50 µg of the MAP in PBS, three days before fusion. Splenocytes were isolated from these mice, fused with the myeloma cell line SP2/O, and the resulting hybridoma cells were plated over macrophages in 96-well plates. Ten days after fusion, media from wells showing cell growth were tested by ELISA. Monoclonal cell lines producing antibodies were identified and then expanded to flasks to prepare large quantities of hybridoma supernatant. Antibodies from the supernatant were then isolated by ammonium sulfate precipitation and purified by using the Affi-Gel Protein A kit (Bio-Rad/Invitrogen, Carlsbad, Calif.) following the manufacturer's instructions.

Example 8

Cloning γ-ECS, GS, and PS for Bacterial Expression

The γ-ECS (GenBank Accession no. X03954) and GS (GenBank Accession no. 28377) genes were amplified by PCR, using synthetic primers listed in Table 4, from genomic DNA of E. coli SK1592. The fission yeast Schizosaccharomyces pombe PS gene (GenBank Accession no. Z68144) was amplified from a plasmid PsPC/YES clone provided by Julian Schroeder (University of California, San Diego, Calif.). The two oligonucleotide primers for each gene added synthetic flanking sequences necessary for cloning and bacterial expression. The sense primers contained restriction endonuclease cloning sites XhoI and NcoI, a TAA stop codon, and bacterial translation signals (Rugh et al., 1996). The antisense primers contained cloning sites BamHI and HindIII. The PCR products encoding all three genes were cloned first into the XhoI/BamHI replacement region of pBluescript KS(II) (Stratagene, La Jolla, Calif.) and electroporated into E. coli strain Top10F (Invitrogen, Carlsbad, Calif.). Sequencing confirmed the fidelity of the amplified coding sequences. To express higher levels of protein the three genes were subcloned into the NdeI (blunt end)/BamHI replacement region of the expression vector pET15b (Novagen, Madison, Wis.) using post-ligation-digestion with XhoI to select against the parent pET15b vector. These plasmids were expressed in E. coli strain BL121 (Novagen) as per the manufacturer's instructions.

Example 9

Protein Extraction

E. coli strains containing recombinant pBluescript plasmids were cultured overnight at 37° C. with 0.4 mM IPTG and 200 mg/l ampicillin, whereas E. coli strain BL121 with recombinant pET15b plasmids was cultured overnight at 28° C. with 1 mM IPTG and 300 mg/l ampicillin. The overnight cultures were centrifuged at 4° C. To prepare protein extracts for ELISA the cold pellet was washed with borate saline buffer, BSB (100 mM boric acid, 25 mM $Na_2B_4O_7$, and 75 mM NaCl, pH=8.5), resuspended in 2 volumes of BSB plus 5 mg/ml EDTA-free protease inhibitor Tablet™ (Boehringer Mannheim, Indianapolis, Ind.), and immediately sonicated in ice to break the cells. After centrifugation at 10,000×g for 10 min at 4° C., the supernatant (approximately 1.5 µg protein/µl) was divided into aliquots and kept at −70° C. for further use as antigen. The quantification of protein in bacterial extracts was performed using Nano Orange™ Protein Quantitation Kit (Molecular Probes Inc., Eugene, Oreg.). Protein samples for Western blots were prepared by mixing the BSB extract with equal volume of 2×SDS sample buffer (Laemmli, 1970).

Example 10

ELISA Measurement of Antibody Titers

For protein ELISAs equal amounts of total bacterial protein extracts with and without the protein antigen (500-1000 ng/well in 50 µl BSB) were adsorbed overnight to each well in paired wells of ELISA plates. For peptide ELISAs wells were coated with MAP peptides at 20 ng/well in 50 µl BSB. The remaining steps for ELISAs were carried out as described previously (Tam, 1988).

Example 11

Expression of γ-ECS, GS, and PS in *Arabidopsis*

The three cDNAs encoding γ-ECS, GS, and PS were cloned under control of the constitutive ACT2 promoter described previously (An et al., 1996). *Arabidopsis* plants were transformed by vacuum infiltration (Bariola et al., 1999). T1 seeds were sterilized and germinated on solid MS medium supplied with 0.8% Phytagar, kanamycin (50 mg/l), and timentin (300 mg/l). Seedlings that survived the selection were transplanted into soil, and the leaf tissues were collected and kept at −70° C. Wild type and transgenic plant protein extracts were prepared as described earlier (Kandasamy et al., 1999).

Example 12

Immunofluorescence Microscopy

In order to analyze the subcellular localization of the PC synthesizing enzymes, and the reactivity of the antibodies against chemically fixed proteins, we performed immunofluorescence microscopy of two-week-old transgenic *Arabidopsis* seedlings expressing these enzymes. Samples were fixed in 4% paraformaldehyde in PME (50 mM Pipes, 5 mM EGTA, 1 mM $MgSO_4$, 0.5% casein) containing the protease inhibitor cocktail (Boehringer Mannheim, Germany) for 1 h at room temperature and processed for immunolabeling as described previously (Kandasamy et al. 1999). Tissues on slides were blocked for 1 h in TBST-BSA-GS (10 mM Tris-HCl pH 7.5, 150 mM NaCl, 0.05% Tween 20, 5% BSA and 10% goat serum) and then incubated in the primary antibody diluted (5-10 µg/ml) in TBST-BSA-GS overnight. After thorough rinsing in PBS, the slides were incubated for 2-3 h with FITC (Sigma) conjugated anti-mouse IgG at 1:100 dilution. The slides were mounted in 80% glycerol in PBS containing 1 mg/ml p-phenylenediamine (an inhibitor of photo bleaching, Sigma) and observed with a Bio-Rad MRC-600 confocal-scanning microscope.

REFERENCES CITED

An et al. (1996) *Plant J.* 10, 107-121.
Ayers, R. U. (1992) *Proc. Natl. Acad. Sci. USA* 89, 815-820.
Baker, A. J. (2000) *Phytoremediation of contaminated soil and water*, (Terry, N. and Banuelos, G. S., eds.). Boca Raton Fla.: CRC Press LLC. P. 85-107.
Baker et al. (1989) *Biorecovery.* 1, 81-126.
Bariola et al. (1999) *Plant Physiol.* 119, 331-342.
Bent et al. (1994) *Science* 265, 1856-1860.
Bevan et al. (1984) *Nucl. Acids Res.* 12, 811-8721.
Bhattacharjee and Rosen (1996) *J. Biol. Chem.* 271, 24465-24470.
Bizily et al. (1999) *Proc. Natl. Acad. Sci. USA* 96, 6808-6813.
Bradford, M. M. (1976) *Anal. Biochem.* 72, 248-254.
Brown et al. (1995a) *Environ. Sci. Technol.* 29, 1581-1585.
Brown et al. (1995b) *Soil Science Society* 59, 125-133.
Carlin et al. (1995) *J. Bacteriol.* 177, 981-986.
Castresana et al. (1988) *EMBO J.* 7, 1929-1936.
Chen et al. (1986) *J. Biol. Chem.* 261, 15030-15038.
Condit et al. (1990) *Plant Physiol.* 93, 596-602.
Cruz et al. (2000) *J. Pept. Sci.* 65, 217-224.
Dey et al. (1994) *Molec. Biochem. Parasitol.* 67, 49-57.
Dittmer, H. J. (1937) *Am. J. Bot.* 24,417-420.
Ebbs et al. (1997) *J. Environ. Quality* 26, 1424-1430.
Gladysheva et al. (1994) *Biochemistry* 33,7288-7293.
Goldsbrough, P. (1998) *Phytoremediation of Contaminated Soil and Water*, (Terry, N. and Banuelos, G., eds.). CRC Press, Boca Raton, Fla. pp. 221-233.
Grec et al. (2000) *Gene* 242, 87-95.
Heidecker et al. (1986) *Ann. Rev. Plant Phys.* 37, 451-462.
Kandasamy and Meagher (1999) *Cell Motility Cytoskeleton* 44, 110-118.
Kohler and Milstein (1975) *Nature* 256, 495.
Laemmli, U. K. (1970) *Nature* 227, 680-685.
Liu et al. (1995) *Biochemistry* 34, 13472-13476.
McGrath et al. (1992) *Plant Mol. Biol.* 19, 725-733.
McGrath et al. (1993) *Integrated Soil and Sediment Research: a basis for proper prediction*, (Eijsackers, H. J. P. and Hamers, T., eds.). Dordrecht, The Netherlands: Kluwer Academic Publishers. pp. 673-676.
McLean et al. (1990) *Plant Cell* 2, 335-344.
Meagher, R. B. (2000) *Curr. Opin. Plant Biol.* 3, 153-162.
Mobley et al. (1983) *Mol. Gen. Genet.* 191, 421-426.
Murphy et al. (2000) *Proc. Int. Conf. Intell. Syst. Mol. Biol.* 8, 251-259.
Nicholson et al. (1994) *Environ. Sci. Technol.* 28, 2170-2175.
Nriagu, J. O. (1980) *Cadmium in the Environment. Part 1: Ecological Cycling.* John Wiley and Sons, New York, N.Y.
Oden et al. (1994) *Molec. Microbiol.* 12, 301-306.
Palanivela et al. (2000) *Plant J.* 199-210.
Posnett et al. (1988) *J. Biol. Chem.* 263, 1719-1725.
Raskin, I. (1996) *Proc. Natl. Acad. Sci. USA* 93, 3164-3166.
Rensing et al. (1997) *Proc. Natl. Acad. Sci. USA* 94, 14326-31.
Robinson et al. (1997) *J. Geochem. Explor.* 60, 115-126.
Rosen, B. P. (1999) *Trends Microbiol.* 7, 207-212.
Rosen et al. (1991) *Arch. Biochem Biophys.* 284, 381-385.
Rosenstein et al. (1992) *J. Bacteriol.* 174, 3676-3683.
Rugh et al. (1998) *Nature Biotechnol.* 16, 925-928
Rugh et al. (1996) *Proc. Natl. Acad. Sci. USA* 93, 3182-3187.
Ryan et al. (1982) *Environmental Research* 28, 251-302.
Salt et al. (1995) *Biotechnology.* 13, 468-474.
Sherlock, J. (1984) *Experientia.* 40, 152-156.
Shi et al. (1994) *J. Biol. Chem.* 269, 19826-19829.
Shirley et al. (1987) *Nuc. Acids Res.* 15, 6501-6514.
Shirley et al. (1990) *Plant Mol. Biol.* 14, 909-925
Stone et al. (1991) *Forest Ecol. and Management*, Elsevier Science Publishers. pp. 59-102.
Tainer et al. (1984) *Nature* 312, 127-134.
Tam, J. P. (1988) *Proc. Natl. Acad. Sci. USA* 85, 5409-5413.
Tam and Lu (1989) *Proc. Natl. Acad. Sci. USA* 86, 9084-9088.
Tsai et al. (1997) *Zoological Studies* 36, 1-16.
Wu and Rosen (1993) *J. Biol. Chem.* 268, 52-58.
Zhu et al. (1999) *Plant Physiol.* 119, 73-79.
Zhu et al. (1999) *Plant Physiol* 121, 1169-1177.

TABLE 1

Filter disk assay for metal ion sensitivity in E. coli

| Strain and plasmid(s) | Size of sensitivity zone (mm) | |
|---|---|---|
| | 10 µl | 5 µl |
| CdCl$_2$, 100 mM | | |
| W3110 + pBSSKII | 26 | 22 |
| Aw3110 + pBSSKII | 26 | 21 |
| Aw3110 + pNA1 | 27 | 18 |
| Rw3110 + pBSSKII | 47 | 39 |
| RW3110 + pNA1 | 23 | 19 |
| As$_2$O$_5$, 250 mM | | |
| AW10 + pBSSKII | 20 | 16 |
| AW10 + pNA1 | 10 | 8 |

TABLE 2

```
LOCUS            R77ARO 4347 bp DNA BCT 26-AUG-1994
DEFINITION       Plasmid R773 arsenical resistance operon genes, arsA, arsB and
                 arsC, complete cds.
GENBANK ACCESSION J02591; VERSION J02591.1 GI: 151856
ORGANISM         Plasmid R773
AUTHORS          Chen, C. M., Misra, T. K., Silver, S. and Rosen, B. P.
TITLE            Nucleotide sequence of the structural genes for an anion pump.
The
                 plasmid-encoded arsenical resistance operon
JOURNAL          J. Biol. Chem. 261 (32), 15030-15038 (1986)
RBS              3275 . . . 3278
                 /gene = "arsC"
                 /note = "putative"
gene             3275 . . . 3711
                 /gene = "arsC"
CDS              3286 . . . 3711
                 /gene = "arsC"
                 /note = "arsenical pump modifier"
                 /codon_start = 1
                 /transl_table = 11
                 /product = "ArsC"
                 /protein_id = "AAA21096.1"
                 /db_xref = "GI: 151859"
translation = "MSNITIYHNPACGTSRNTLEMIRNSGTEPTIILYLENPPSRDEL
VKLIADMGISVRALLRKNVEPYEQLGLAEDKFTDDQLIDFMLQHPILINRPIVVTPLG
TRLCRPSEVVLDILQDAQKGAFTKEDGEKVVDEAGKRLK"
BASECOUNT        979 a 1082 c 1165 g 1121 t
ORIGIN           HindIII site.
    1 agcttccggg gcagaaggtc tgccattgtt gttactggat ggcgaaacag tgatggccgg
   61 gcgttacccg aaacgcgctg agctggctcg ctggtttggc attccactgg ataaagtggg
  121 attagcgcct tcaggttgct gtggtggtaa tacttcttgt tgttaagtat atcaggagga
```

TABLE 2-continued

```
 181   catatgcaat tcttacagaa tatccccct  tatctgtttt ttacgggtaa aggaggcgtg
 241   ggtaaaacct ctatttcctg cgccacggcg atccgtctgg cagaacaggg gaaacgggtg
 301   ctgctggtca gtaccgatcc ggcctcaaac gtaggccagg tgtttagcca gacgattggc
 361   attaccattc aggcaatagc ctctgttcct ggattgtcgg ctcttgagat tgatcctcag
 421   gctgctgcac aacagtaccg ggccagaatc gttgaccta  ttaaaggcgt cctgcctgat
 481   gacgttgttt ccagcatcaa cgaacaactg tcaggtgcat gcacaacaga gattgcggct
 541   tttgatgaat ttaccggatt actgacagat gcctctctgc tgacgcggtt tgaccatatc
 601   attttgata  ccgcgccgac gggtcacacc attcgccttc tgcagttgcc gggcgcctgg
 661   agtagcttta ttgacagcaa tcccgagggc gcgtcctgtc tcggcccaat ggcggggctg
 721   gaaaagcagc gtgaacagta tgcctatgct gttgaagcgt tgtctgatcc aaagcgtacc
 781   cgactggtat tagttgctcg tctgcaaaaa tccacgttgc aggaagtcgc ccggactcat
 841   ctggaacttg ccgccatcgg ccttaaaaat cagtacctgg ttattaatgg cgttctgccc
 901   aaaactgaag cggcaaacga tacactggct gctgcaatat gggagcgtga acaggaggcg
 961   ctggccaatc ttcccgctga tcttgcaggt tgccaactga acacattatt tctccagccg
1021   gtcaataggg tcggtgtgtc tgcgctcagc aggcttctct ccactcagcc tgtagcgtcg
1081   ccatcctcgg atgaatacct gcaacagcgg cctgatattc gtcactttc  tgcgttggtt
1141   gatgatattg cccgtaatga acatggcctg attatgctga tgggtaaagg tggcgtgggg
1201   aaaaccacga tggctgctgc cattgctgtc aggctggccg acatgggatt tgatgtccat
1261   ctgacaacat ctgatcctgc ggcgcatctc agcatgaccc tgaacggtag ccttaacaac
1321   ctgcaggtca gcaggatcga tcctcacgag gaaacggaac gctatcgtca gcatgttctt
1381   gaaacaaagg gaaaagaact ggacgaagcg ggaaaacgcc tgctggaaga ggacttacgc
1441   tcaccttgca ctgaggaaat tgctgttttc caggcctttt cacgggtgat tcgtgaagcg
1501   ggtaaacgtt tcgtggtgat ggatacggct ccgaccggac acacgctgtt gctgctggat
1561   gctacaggcg cgtaccaccg cgaaattgcg aagaaaatgg gagaaaaagg ccatttcacc
1621   acaccgatga tgctgcttca ggatccggag cgcactaaag tgttactggt cacgctgccg
1681   gaaaccacgc ccgtgcttga agcggcaaat ttacaggccg accttgagcg tgcaggcatt
1741   cacccctggg gctggattat caataacagc ctttccattg cggatacccg ttcgccactg
1801   cttcgtatgc gggcacaaca ggaacttccg cagatagaga gcgttaaacg ccagcacgcc
1861   agccgtgtcg ctcttgttcc cgtactggcg tcagaaccaa ccggcatcga caaactcaaa
1921   caacttgctg ggtaaaattat tgtcatcacg tagggcagca aagctgccct gtcaggaggt
1981   tttatgttac tggcaggagc cattttatc  ctgaccatcg ttttggttat ctggcagccg
2041   aaaggattag ggattggctg gagcgccacg ttggggggctg tactggctct ggcgtcgggt
2101   gtgatacaca ttgctgatat tccggtggtg tggaatattg tctggaacgc gacggcaaca
2161   tttatcgccg ttattatcat cagcctgttg ctggatgagt caggcttttt cgaatgggca
2221   gcgttgcacg tttctcgctg ggggaacggt cgtggccgcc tgctgtttac gtatattgtt
2281   ctgctcggcg cggcagtggc ggcactgttt gccaacgatg gtgcggctct tattctgacg
2341   ccgattgtta tcgccatgct gctggcgctt ggcttcagta aaagcaccac actggcattc
2401   gtgatggctg ccgggttat  ttccgatact gctagcttgc cgcttatcgt atcgaacttg
2461   gtcaatatcg tttcagctga tttcttcaaa ctgggattca cggagtatgc ttcggtgatg
```

TABLE 2-continued

```
2521  gtgccggtgg atatcgccgc cattatcgcc acgctggtga tgctgcatct ttttttccgc
2581  aaagatatcc cccccactta tgagctggcg cgactgaaag aacctgcaaa agccatcaaa
2641  gatcctgcga cgttcagaac cggctgggtt gttctcctcc ttctgctggt cggttttttt
2701  gtccttgagc cgatggggat ccctgtgagt gcgattgcag cagtgggggc ggcagtcctg
2761  tttgcggtgg ccaaaaaagg tcatggtatt aacaccggta aagtgctgcg cggcgcgccc
2821  tggcagatcg tgatcttctc tctggggatg tatctggtga tctacgggtt gcgtaacgcc
2881  ggtctgacag attatctctc tgacgtgctg aacgaactgg cagataaagg actgtgggcc
2941  gccacgctgg ggacgggatt cctgacagca ttactctctt ctattatgaa caatatgccg
3001  acagtattga ttggcgcatt gtcaattgat ggcagcaccg cgaccggtgt tatcaaagag
3061  gcgatgattt atgccaacgt cattggctgc gatctggggc gaaaatcac ccctattggt
3121  agcctggcaa cactgctctg gctgcatgta ctttcacaga gaacatgac catcacttgg
3181  ggatactatt ccgcaccgg gatcgtcatg actctgcctg tgctgtttgt aacgctggcc
3241  gcgctggcgc tacgtctctc tgtcacattg taatgagatt ctgatatgag caacatcact
3301  atttatcata cccagcctg cggcacctcg cgtaatacg tggagatga ccgcaacagc
3361  ggtaccgagc cgaccattat tctttacctt gaaaacccgc cttcgaggga tgagctggtt
3421  aaacttattg ccgatatggg tatttcagta cgagcgctgc tgcgtaaaaa cgttgaacct
3481  tacgagcaac tgggtcttgc agaagataaa tttactgacg atcagctcat cgactttatg
3541  ttgcaacacc caattctgat taaccgtccg atcgtggtta cgccgctggg aaccagactg
3601  tgccgtcctt ctgaagtggt tctggatatc ctacaggatg cgcagaaagg ggctttcact
3661  aaggaagacg gtgaaaaagt cgttgatgaa gcaggaaaac ggctgaaata aataataagg
3721  gggcgaatgc cccttattc gtacctcaga gcatcatgcc tgaatccgat ggtaacgtgc
3781  tgttcccttc gcccagattt cgttgcagca cactgtgtc aagccaacga ccatgcttga
3841  agccaatatt tttcagcgta ccaatctcag taaatccaac ctgctgatgg actttcagcg
3901  aaccttgatt attgctatcg ccgacaatag caatcatctg ccgatagccg tgagttttg
3961  cccaggaaat gacgtagcgc agcaacgctt ttcctgtccc ccgacgctgt gcgtccgggt
4021  gaatataaat cgaatcttcg agagtgtggc ggtaggcgta gcgttcacgg taacgagtga
4081  gataacaata cccgataacc ttttcttcct ctaacgtgac aacccacggt agctcctgat
4141  tgcggatctt tttcaggcgg gcaagcatct cgtgggtatc cggaggttca gtttcaaagc
4201  tggcggtacc gtgaagaaca tgatgggcgt agatatcgcg tatagcgggg atgtgctttt
4261  cttctgcgtt aacgattttc attgttctgt tcccgttggc atcttttttca aggttacttg
4321  aaaatccaga ggaaaggtaa atacaaa
```

TABLE 3

Bacterial Arsenate Reductase Sequences

| | | |
|---|---|---|
| 1: | NC 000917<br>*Archaeoglobus fulgidus*, complete genome<br>gi\|11497621\|ref\|NC_000917.1\|[11497621] | PubMed, Protein, |
| 2: | AE000426<br>*Escherichia coli* K12 MG1655 section 316 of 400 of the complete genome<br>gi\|1789910\|gb\|AE000426.1\|AE000426[1789910] | PubMed, Protein, Related Sequences, Genome, |
| 4: | NC 002120<br>*Yersinia enterocolitica* plasmid pYVe227, complete sequence<br>gi\|10955536\|ref\|NC_002120.1\|[10955536] | PubMed, Protein, |

TABLE 3-continued

Bacterial Arsenate Reductase Sequences

5: NC 001869  
*Halobacterium* sp. NRC-1 plasmid pNRC100, complete sequence  
gi|10803547|ref|NC_001869.1|[10803547]  
PubMed, Protein, 6: AL445066  
*Thermoplasma acidophilum* complete genome; segment 4/5  
gi|10640244|emb|AL445066.1|TACID4[10640244]  
PubMed, Protein, Related Sequences, Genome, 7: AP001518  
*Bacillus halodurans* genomic DNA, section 12/14  
gi|10175792|dbj|AP001518.1|AP001518[10175792]  
PubMed, Protein, Related Sequences, Genome, 8: AP001517  
*Bacillus halodurans* genomic DNA, section 11/14  
gi|10175500|dbj|AP001517.1|AP001517[10175500]  
PubMed, Protein, Related Sequences, Genome, 9: AL355740  
*Streptomyces coelicolor* cosmid 3H12  
gi|7799215|emb|AL355740.1|SC3H12[7799215]  
PubMed, Protein, Related Sequences, 10: AE004529  
*Pseudomonas aeruginosa* PA01, section 90 of 529 of the complete genome  
gi|9946851|gb|AE004529.1|AE004529[9946851]  
PubMed, Protein, Related Sequences, Genome, 11: AE004288  
*Vibrio cholerae* chromosome I, section 196 of 251 of the complete chromosome gi|9656710|gb|AE004288.1|AE004288[9656710]  
PubMed, Protein, Genome, 12: AF168737  
*Klebsiella oxytoca* plasmid pMH12 arsenical resistance operon, complete sequence  
gi|9622142|gb|AF168737.1|AF168737[9622142]  
Protein, 13: AE002359  
*Neisseria meningitidis* serogroup B strain MC58 section 1 of 206 of the complete genome  
gi|7225225|gb|AE002359.1|AE002359[7225225]  
PubMed, Protein, Related Sequences, Genome, 14: AL355752  
*Streptomyces coelicolor* cosmid 10B7  
gi|7799230|emb|AL355752.1|SC10B7[7799230]  
PubMed, Protein, Related Sequences, 15: U76418  
*Neisseria gonorrhoeae* glutamyl-tRNA synthetase (gltX) gene, partial cds; arsenate reductase, thioredoxin-like protein, FtsE-like protein, and FtsX-like protein genes, complete cds; and 3-phosphoglycerate kinase (pgk) gene, partial cds  
gi|1684777|gb|U76418.1|NGU76418[1684777]  
PubMed, Protein, 16: AF173880  
*Thiobacillus ferrooxidans* arsenate reductase (arsC), ArsR-like protein, arsenite membrane pump (arsB), ArsH-like protein, signal recognition particle protein like protein, 30S ribosomal protein S16-like protein, and 16S ribosomal RNA processing protein RIMM-like protein genes, complete cds; and unknown genes gi|7769066|gb|AF173880.1|AF173880[7769066]  
PubMed, Protein, 17: AJ288983  
*Serratia marcescens* plasmid R478 (IncHI2 family) arsenical resistance operon (arsRBCH)  
gi|7636044|emb|AJ288983.1|SMA288983[7636044]  
Protein, 18: AL162752  
*Neisseria meningitidis* serogroup A strain Z2491 complete genome; segment 1/7  
gi|7378778|emb|AL162752.2|NMA1Z2491[7378778]  
PubMed, Protein, Related Sequences, Genome, 19: D90914  
*Synechocystis* sp. PCC6803 complete genome, 16/27, 1991550–2137258  
gi|1653477|dbj|D90914.1|D90914[1653477]  
PubMed, Protein, Related Sequences, Genome, 20: AL138667  
*Streptomyces coelicolor* cosmid 3D9  
gi|6900901|emb|AL138667.1|SC3D9[6900901]  
PubMed, Protein, Related Sequences, 21: AE000666  
*Methanobacterium thermoautotrophicum* delta H complete genome  
gi|6626257|gb|AE000666.1|MTHE[6626257]  
PubMed, Protein, 22: L42023  
*Haemophilus influenzae* Rd complete genome  
gi|6626252|gb|L42023.1|L42023[6626252]  
PubMed, Protein, 23: U00096  
*Escherichia coli* K-12 MG1655 complete genome  
gi|6626251|gb|U00096.1|U00096[6626251]  
PubMed, Protein, 24: AE000657  
*Aquifex aeolicus* complete genome  
gi|6626248|gb|AE000657.1|AE000657[6626248]  
PubMed, Protein, 25: AE000782  
*Archaeoglobus fulgidus* complete genome  
gi|6626247|gb|AE000782.1|AE000782[6626247]  
PubMed, Protein, 26: AE001862  
*Deinococcus radiodurans* R1 section 1 of 2 of the complete chromosome 2  
gi|6460468|gb|AE001862.1|AE001862[6460468]  
PubMed, Protein, Related Sequences, Genome, TABLE 3-continued Bacterial Arsenate Reductase Sequences 27: AJ251005  
*Streptomyces coelicolor* arsC gene, trxB gene and arsR gene (partial)  
gi|6448621|emb|AJ251005.1|SCO251005[6448621]  
Protein, Related Sequences, 28: AF178758  
*Sinorhizobium* sp. As4 arsenical resistance operon, complete sequence  
gi|5802940|gb|AF178758.1|AF178758[5802940]  
Protein, 29: AL078610  
*Streptomyces coelicolor* cosmid H35  
gi|5019320|emb|AL078610.1|SCH35[5019320]  
PubMed, Protein, Related Sequences, 30: Y13833  
*Streptomyces coelicolor* arsC (partial), glnII genes, ORF2, ORF3 & ORF  
gi|4972275|emb|Y13833.1|SCY13833[4972275]  
Protein, Related Sequences, 31: AF102990  
*Yersinia enterocolitica* plasmid pYVe227, complete sequence  
gi|4324323|gb|AF102990.1|AF102990[4324323]  
PubMed, Protein, Related Sequences, 32: AF016485  
*Halobacterium* sp. NRC-1 plasmid pNRC100, complete plasmid sequence  
gi|2822278|gb|AF016485.1|AF016485[2822278]  
PubMed, Protein, Related Sequences, 34: AF010234  
*Pseudomonas aeruginosa* ars operon, regulator (arsR), membrane pump (arsB) and arsenate reductase (arsC) genes, complete cds  
gi|3095049|gb|AF010234.1|AF010234[3095049]  
PubMed, Protein, Related Sequences, 35: Z80225  
*Mycobacterium tuberculosis* H37Rv complete genome; segment 118/162  
gi|3242265|emb|Z80225.1|MTCY441[3242265]  
PubMed, Protein, Related Sequences, Genome, 36: U32710  
*Haemophilus influenzae* Rd section 25 of 163 of the complete genome  
gi|1573200|gb|U32710.1|U32710[1573200]  
PubMed, Protein, Related Sequences, Genome, 37: AF010496  
*Rhodobacter capsulatus* strain SB1003, partial genome  
gi|3128256|gb|AF010496.1|AF010496[3128256]  
PubMed, Protein, Related Sequences, 38: AF047036  
*Pseudomonas fluorescens* arsenate reductase enzyme (ars) gene sequence  
gi|3002964|gb|AF047036.1|AF047036[3002964]

39: AE000702  
*Aquifex aeolicus* section 34 of 109 of the complete genome  
gi|2983276|gb|AE000702.1|AE000702[2983276]  
PubMed, Protein, Genome, 40: AB004659  
*Acidiphilium multivorum* plasmid pKW301 gene for ArsR, ArsD, ArsA, ArsB ArsC, complete cds  
gi|2879916|dbj|AB004659.1|AB004659[2879916]  
PubMed, Protein, 41: AE001010  
*Archaeoglobus fulgidus* section 97 of 172 of the complete genome  
gi|2689333|gb|AE001010.1|AE001010[2689333]  
PubMed, Protein, Related Sequences, 42: Z99120  
*Bacillus subtilis* complete genome (section 17 of 21)  
gi|2635613|emb|Z99120.1|BSUB0017[2635613]  
PubMed, Protein, Related Sequences, Genome, 43: Z99117  
*Bacillus subtilis* complete genome (section 14 of 21)  
gi|2634966|emb|Z99117.1|BSUB0014[2634966]  
PubMed, Protein, Related Sequences, Genome, 44: AE000898  
*Methanobacterium thermoautotrophicum* from bases 1211967 to 1222915 (section 104 of 148) of the complete genome  
gi|2622453|gb|AE000898.1|AE000898[2622453]  
PubMed, Protein, Related Sequences, Genome, 45: D32216  
*Bacillus subtilis* 48 kb region including a skin element which is located between spoIVCB and spoIIIC  
gi|556476|dbj|D32216.1|BACSKIN[556476]  
PubMed, Protein, Related Sequences.

46: D90889  
*E. coli* genomic DNA, Kohara clone #442(59.7–60.0 min.)  
gi|1800027|dbj|D90889.1|D90889[1800027]  
PubMed, Protein, Related Sequences, 47: D90878  
*E. coli* genomic DNA, Kohara clone #425(56.2–56.5 min.)  
gi|1805551|dbj|D90878.1|D90878[1805551]  
PubMed, Protein, Related Sequences, 48: U58366  
*Yersinia enterocolitica* Tn2502 transposon defective transposase (tnpA), resolvase (tnpR), arsenate reductase (arsC), transmembrane protein of arsenite pump (arsB), arsenite inducible repressor (arsR), and ArsH (arsH) genes, complete cds  
gi|1545989|gb|U58366.1|YEU58366[1545989]  
PubMed, Protein, Related Sequences, 49: U38947  
Plasmid R46 arsenical resistance operon, repressor protein (arsR), repressor protein (arsD), arsenite activated ATPase (arsA), arsenite transport protein (arsB), and arsenate reductase (arsC) genes, complete cds  
gi|1061413|gb|U38947.1|PRU38947[1061413]  
PubMed, Protein, TABLE 3-continued Bacterial Arsenate Reductase Sequences 50: X80057  
   *E. coli* genes arsR, arsB, arsC  
   gi|510824|emb|X80057.1|ECARSRBC[510824]  
   PubMed, Protein, Related Sequences,
51: M80565  
   *Staphylococcus xylosus* arsenic efflux pump protein (arsB) arsenate reductase (arsC) and operon regulatory protein (arsR) genes, complete operon  
   gi|155343|gb|M80565.1|X26ARSOPRN[155343]  
   PubMed, Protein, Related Sequences,
52: M86824  
   Plasmid pI258 arsenic resistance operon (arsRBC) genes, complete cds  
   gi|150725|gb|M86824.1|PI2ARSRBC[150725]  
   PubMed, Protein, Related Sequences,

TABLE 4

Oligonucleotide primers used to amplify the γECS, GS, and PS genes by PCR

| Gene | Sense Primer | Antisense Primer |
|------|--------------|------------------|
| ECS | <u>CACAGCCTCGAGTAAGG AGGAGGAGCCACCATGG</u> CAATCCCGGACGTATCA CAGGCGCT (SEQ ID NO: 5) | <u>GAGTCGGGATCCAAGCTTTCA</u> GGCGTGTTTTTCCAGCCACAC CGCAA (SEQ ID NO: 6) |
| GS | <u>CGAGCCCTCGAGTAAGGA GCCACCATGGCAATCAAG</u> CTCGGCATCGTGATGGACC CCAT (SEQ ID NO: 7) | <u>ACGTGCGGATCCAAGCTTATT</u> ACTGCTGCTGTAAACGTGCTT CGAT (SEQ ID NO: 8) |
| PS | <u>CGAGCGCTCGAGTAAGGA GGAGCCACCATGGCAACC</u> AATGCAACACCAAATATC GGT (SEQ ID NO: 9) | <u>CGAGCGGGATCCGAGCTCTCA</u> CGTATTTTTACAGCAGCTTGA ACTA (SEQ ID NO: 10) |

Sequences are listed 5' to 3'. The underlined segments contain restriction sites and clamps.

TABLE 5

Titers of mouse[a] serum against three PC synthesizing enzymes

| Mouse # | γECS extract | GS- extract | PS- extract | Control extract | Ratio[b] extracts | PS[c] NMAP | BSA[c] Control |
|---------|------|------|------|------|------|------|------|
| ECS-NMAP-#1 | 1.89 | | | 0.144 | 13.1 | | |
| ECS-NMAP-#2 | 1.83 | | | 0.159 | 11.5 | | |
| GS-NMAP-#1 | | 2.20 | | 0.229 | 9.6 | | |
| GS-NMAP-#2 | | 2.12 | | 0.335 | 6.3 | | |
| PS-NMAP-#1 | | | 0.28 | 0.048 | 5.8 | 1.50 | .021 |
| PS-NMAP-#2 | | | 0.24 | 0.070 | 3.5 | 2.28 | .030 |

[a] Data are for the two mice with the best activities that were used as the sources of splenic B-cells for hybridoma fusions. Titer values are given as optical density units taken at $A_{405}$ minus the background at $A_{485}$. They are typical of several independent measurements that were made on a 1/3000 dilution of serum.
[b] Ratio of the titer values for the recombinant protein extracts relative to control extracts
[c] Titers against PS-NMAP are compared to controls where the ELISA wells were treated with BSA.

TABLE 6

*Arabidopsis phytochelatins* synthase (AtPCS) coding sequence (1515 nucleotides) was cloned into NcoI/BamH1 restriction sites between ACT2 promoter and ACT2 terminater in pBluescript (II) KS  
(SEQ ID NO: 16)

1  AAGCTTGCAT GCTGATCTCA AATACATTGA TACATATCTC
       ATCTAGATCT
   51  AGGTTATCAT TATGTAAGAA AGTTTTGACG AATATGGCAC
       GACAAAATGG
  101  CTAGACTCGA TGTAATTGGT ATCTCAACTC AACATTATAC
       TTATACCAAA
  151  CATTAGTTAG ACAAAATTTA AACAACTATT TTTTATGTAT
       GCAAGAGTCA
  201  GCATATGTAT AATTGATTCA GAATCGTTTT GACGAGTTCG
       GATGTAGTAG
  251  TAGCCATTAT TTAATGTACA TACTAATCGT GAATAGTGAA
       TATGATGAAA
  301  CATTGTATCT TATTGTATAA ATATCCATAA ACACATCATG
       AAAGACACTT
  351  TCTTTCACGG TCTGAATTAA TTATGATACA ATTCTAATAG
       AAAACGAATT
  401  AAATTACGTT GAATTGTATG AAATCTAATT GAACAAGCCA
       ACCACGACGA
  451  CGACTAACGT TGCCTGGATT GACTCGGTTT AAGTTAACCA
       CTAAAAAAAC
  501  GGAGCTGTCA TGTAACACGC GGATCGAGCA GGTCACAGTC
       ATGAAGCCAT

TABLE 6-continued

```
 551  CAAAGCAAAA GAACTAATCC AAGGGCTGAG ATGATTAATT
      AGTTTAAAAA

601  TTAGTTAACA CGAGGGAAAA GGCTGTCTGA CAGCCAGGTC
      ACGTTATCTT

651  TACCTGTGGT CGAAATGATT CGTGTCTGTC GATTTTAATT
      ATTTTTTTGA

701  AAGGCCGAAA ATAAAGTTGT AAGAGATAAA CCCGCCTATA
      TAAATTCATA

751  TATTTTCCTC TCCGCTTTGA ATTGTCTCGT TGTCCTCCTC
      ACTTTCATCA

801  GCCGTTTTGA ATCTCCGGCG ACTTGACAGA GAAGAACAAG
      GAAGAAGACT

851  AAGAGAGAAA GTAAGAGATA ATCCAGGAGA TTCATTCTCC
      GTTTTGAATC

901  TTCCTCAATC TCATCTTCTT CCGCTCTTTC TTTCCAAGGT
      AATAGGAACT

951  TTCTGGATCT ACTTTATTTG CTGGATCTCG ATCTTGTTTT
      CTCAATTTCC

1001  TTGAGATCTG GAATTCGTTT AATTTGGATC TGTGAACCTC
      CACTAAATCT

1051  TTTGGTTTTA CTAGAATCGA TCTAAGTTGA CCGATCAGTT
      AGCTCGATTA

1101  TAGCTACCAG AATTTGGCTT GACCTTGATG GAGAGATCCA
      TGTTCATGTT

1151  ACCTGGGAAA TGATTTGTAT ATGTGAATTG AAATCTGAAC
      TGTTGAAGTT

1201  AGATTGAATC TGAACACTGT CAATGTTAGA TTGAATCTGA
      ACACTGTTTA

1251  AGGTTAGATG AAGTTTGTGT ATAGATTCTT CGAAACTTTA
      GGATTTGTAG

1301  TGTCGTACGT TGAACAGAAA GCTATTTCTG ATTCAATCAG
      GGTTTATTTG

1351  ACTGTATTGA ACTCTTTTTG TGTGTTTGCA GCTCATAAAC
      CATGGcagct 1401  atggcgagtt tatatcggcg atctcttcct tctcctccgg
      ccattgactt 1451  ttcttccgcc gaaggcaagc taatcttcaa tgaagcgctt
      caaaaaggaa 1501  ctatggaagg atttttcagg ttgatttcgt attttcagac
      acaatccgaa 1551  cctgcgtatt gtggtttggc tagtctctca gtggtgttga
      atgctctttc 1601  tatcgatcct ggacgtaaat ggaaagggcc ttggaggtgg
      tttgatgaat 1651  caatgttgga ttgctgcgaa cctctggaag tagtgaagga
      aaaaggcatt 1701  tcatttggaa aagttgtctg tttggctcat tgttcaggag
      caaaagttga 1751  ggctttccgt acaagtcaga gcaccattga tgatttccgc
      aaatttgtcg 1801  tcaaatgcac gagttctgag aattgtcata tgatctcaac
      atatcaccga 1851  agtgtattta agcagactgg gaatggtcac ttttcaccta
      ttggtggcta 1901  taatgctgag agagatatgg ctttgattct tgatgttgct
      cgtttcaagt 1951  atccccctca ctgggttcct cttaaacttc tttgggaagc
      catggacagt 2001  attgatcagt caacagggaa acgtagaggg ttcatgctca
      tatctagacc 2051  acacagagaa cccggattgc tctatactct gagctgcaag
      gatgaaagct 2101  ggatcgaaat agccaagtat ttgaaggaag atgttcctcg
      tcttgtaagt 2151  tcacagcatg tagattctgt ggagaaaatc atatcagttg
      tgttcaagtc 2201  acttccatca aatttcaacc aattcatcag atgggtggct
      gagatccgaa 2251  ttacagagga ctcaaaccaa aatctcagcg cagaggagaa
      gtctaggctg 2301  aaactaaagc aattggtgct gaaggaagtg cacgaaactg
      aactgttcaa 2351  acacatcaat aagttcttat ccacagtggg ttatgaagac
      agtctgactt 2401  atgctgctgc aaaggcttgt tgccaaggag ctgaaatctt
      atccggaagc 2451  ccatcaaaag agttttgttg tcgggaaact gcgtgaaat
      gcatcaaagg 2501  tcctgatgac tctgaaggca cggtggtgac tggagttgtg
      gtgcgtgatg 2551  ggaatgaaca aaaggttgat ctgttagtgc catcgacgca
      aactgagtgt 2601  gaatgtggtc ctgaagcaac ttatccagca ggaaacgatg
      tgttcactgc 2651  acttctattg gctttacctc cacagacatg gtcagggatc
      aaagaccaag 2701  ctcttatgca tgaaatgaag cagctcattt ccatggcttc
      cctcccaact 2751  ttgcttcaag aagaggtatt gcatcttcga cggcaacttc
      agctgctaaa 2801  acgatgccaa gagaacaagg aagaggatga tctcgctgct
      cctgcctatt 2851  agttcattgt cccaaatcct ctctcttccc catttgaatc
      ccacgttctc 2901  tacacttaaG GATCCTCTAG ACTCGGAGGC TCTCAAGATC
      AAAGGCTTAA

2951  AAAGCTGGGG TTTTATGAAT GGGATCAAAG TTTCTTTTTT
      TCTTTTATAT

3001  TTGCTTCTCC ATTTGTTTGT TTCATTTCCC TTTTTGTTTT
      CGTTTCTATG

3051  ATGCACTTGT GTGTGACAAA CTCTCTGGGT TTTTACTTAC
      GTCTGCGTTT

3102  CAAAAAAAAA AACCGCTTTC GTTTTGCGTT TTAGTCCCAT
      TGTTTTGTAG

3151  CTCTGAGTGA TCGAATTGAT GCCTCTTTAT TCCTTTTGTT
      CCCTATAATT

3201  TCTTTCAAAA CTCAGAAGAA AAACCTTGAA ACTCTTTGCA
      ATGTTAATAT
```

TABLE 6-continued

```
3251 AAGTATTGTA TAAGATTTTT ATTGATTTGG TTATTAGTCT
     TACTTTTGCT

3301 ACCTCCATCT TCACTTGGAA CTGATATTCT GAATAGTTAA
     AGCGTTACAT

3351 GTCTTCCATT CACAAATGAA CTTAAACTAG CACAAAGTCA
     GATATTTTAA

3401 GAGAATTC
```

TABLE 7

Bacterial gamma-glutamyl cysteine synthetase (g-ECS) coding sequence (1560 nucleotides) was cloned into NcoI/BamH1 restriction sites between ACT2 promoter and ACT2 terminator in pBluescript (II) KS (SEQ ID NO: 17)

```
   1 AAGCTTGCAT GCTGATCTCA AATACATTGA TACATATCTC
     ATCTAGATCT

51 AGGTTATCAT TATGTAAGAA AGTTTTGACG AATATGGCAC
     GACAAAATGG

101 CTAGACTCGA TGTAATTGGT ATCTCAACTC AACATTATAC
     TTATACCAAA

151 CATTAGTTAG ACAAAATTTA AACAACTATT TTTTATGTAT
     GCAAGAGTCA

201 GCATATGTAT AATTGATTCA GAATCGTTTT GACGAGTTCG
     GATGTAGTAG

251 TAGCCATTAT TTAATGTACA TACTAATCGT GAATAGTGAA
     TATGATGAAA

301 CATTGTATCT TATTGTATAA ATATCCATAA ACACATCATG
     AAAGACACTT

351 TCTTTCACGG TCTGAATTAA TTATGATACA ATTCTAATAG
     AAAACGAATT

401 AAAATTACGTT GAATTGTATG AAATCTAATT GAACAAGCCA
     ACCACGACGA

451 CGACTAACGT TGCCTGGATT GACTCGGTTT AAGTTAACCA
     CTAAAAAAAC

501 GGAGCTGTCA TGTAACACGC GGATCGAGCA GGTCACAGTC
     ATGAAGCCAT

551 CAAAGCAAAA GAACTAATCC AAGGGCTGAG ATGATTAATT
     AGTTTAAAAA

601 TTAGTTAACA CGAGGGAAAA GGCTGTCTGA CAGCCAGGTC
     ACGTTATCTT

651 TACCTGTGGT CGAAATGATT CGTGTCTGTC GATTTTAATT
     ATTTTTTTGA

701 AAGGCCGAAA ATAAAGTTGT AAGAGATAAA CCCGCCTATA
     TAAATTCATA

751 TATTTTCCTC TCCGCTTTGA ATTGTCTCGT TGTCCTCCTC
     ACTTTCATCA

801 GCCGTTTTGA ATCTCCGGCG ACTTGACAGA AGAACAAG
     GAAGAAGACT

851 AAGAGAGAAA GTAAGAGATA ATCCAGGAGA TTCATTCTCC
     GTTTTGAATC

901 TTCCTCAATC TCATCTTCTT CCGCTCTTTC TTTCCAAGGT
     AATAGGAACT
```

TABLE 7-continued

Bacterial gamma-glutamyl cysteine synthetase (g-ECS) coding sequence (1560 nucleotides) was cloned into NcoI/BamH1 restriction sites between ACT2 promoter and ACT2 terminator in pBluescript (II) KS (SEQ ID NO: 17)

```
 951 TTCTGGATCT ACTTTATTTG CTGGATCTCG ATCTTGTTTT
     CTCAATTTCC

1001 TTGAGATCTG GAATTCGTTT AATTTGGATC TGTGAACCTC
     CACTAAATCT

1051 TTTGGTTTTA CTAGAATCGA TCTAAGTTGA CCGATCAGTT
     AGCTCGATTA

1101 TAGCTACCAG AATTTGGCTT GACCTTGATG GAGAGATCCA
     TGTTCATGTT

1151 ACCTGGGAAA TGATTTGTAT ATGTGAATTG AAATCTGAAC
     TGTTGAAGTT

1201 AGATTGAATC TGAACACTGT CAATGTTAGA TTGAATCTGA
     ACACTGTTTA

1251 AGGTTAGATG AAGTTTGTGT ATAGATTCTT CGAAACTTTA
     GGATTTGTAG

1301 TGTCGTACGT TGAACAGAAA GCTATTTCTG ATTCAATCAG
     GGTTTATTTG

1351 ACTGTATTGA ACTCTTTTTG TGTGTTTGCA GCTCATAAAC
     CATGGcaatc 1401 ccggacgtat cacaggcgct ggcctggctg gaaaaacatc
     ctcaggcgtt 1451 aaaggggata cagcgtgggc tggagcgcga aactttgcgt
     gttaatgctg 1501 atggcacact ggcaacaaca ggtcatcctg aagcattagg
     ttccgcactg 1551 acgcacaaat ggattactac cgattttgcg gaagcattgc
     tggaattcat 1601 tacaccagtg gatggtgata ttgaacatat gctgaccttt
     atgcgcgatc 1651 tgcatcgtta tacggcgcgc aatatgggcg atgagcggat
     gttgccgtta 1701 agtatgccat gctacatcgc agaaggtcag gacatcgaac
     tggcacagta 1751 cggcacttct aacaccggac gctttaaaac gctgtatcgt
     gaagggctga 1801 aaaatcgcta cggcgcgctg atgcaaacca tttccggcgt
     gcactacaat 1851 ttctctttgc caatggcatt ctggcaagcg aagtgcggtg
     atatctcggg 1901 cgctgatgcc aaagagaaaa tttctgcggg ctatttccgc
     gttatccgca 1951 attactatcg tttcggttgg gtcattcctt atctgtttgg
     tgcatctccg 2001 gcgatttgtt cttcttctcct gcaaggaaaa ccaacgtcgc
     tgccgtttga 2051 gaaaaccgag tgcggtatgt attacctgcc gtatgcgacc
     tctcttcgtt 2101 tgagcgatct cggctatacc aataaatcgc aaagcaatct
     tggtattacc
```

TABLE 7-continued

Bacterial gamma-glutamyl cysteine synthetase (g-ECS) coding sequence (1560 nucleotides) was cloned into NcoI/BamH1 restriction sites between ACT2 promoter and ACT2 terminater in pBluescript (II) KS (SEQ ID NO: 17)

| | |
|---|---|
| 2151 | ttcaacgatc tttacgaata cgtagcgggc cttaaacagg caatcaaaac |
| 2201 | gccatcggaa gagtacgcga agattggtat tgagaaagac ggtaagaggc |
| 2251 | tgcaaatcaa cagcaacgtg ttgcagattg aaaacgaact gtacgcgccg |
| 2301 | attcgtccaa aacgcgttac ccgcagcggc gagtcgcctt ctgatgcgct |
| 2351 | gttacgtggc ggcattgaat atattgaagt gcgttcgctg gacatcaacc |
| 2401 | cgttctcgcc gattggtgta gatgaacagc aggtgcgatt cctcgacctg |
| 2451 | tttatggtct ggtgtgcgct ggctgatgca ccggaaatga gcagtagcga |
| 2501 | acttgcctgt acacgcgtta actggaaccg ggtgatcctc gaaggtcgca |
| 2551 | aaccgggtct gacgctgggt atcggctgcg aaaccgcaca gttcccgtta |
| 2601 | ccgcaggtgg gtaaagatct gttccgcgat ctgaaacgcg tcgcgcaaac |
| 2651 | gctggatagt attaacggcg gcgaagcgta tcagaaagtg tgtgatgaac |
| 2701 | tggttgcctg cttcgataat cccgatctga cttttctctg ccgtatctta |
| 2751 | aggtctatga ttgatactgg tattggcgga acaggcaaag catttgcaga |
| 2801 | agcctaccgt aatctgctgc gtgaagagcc gctggaaatt ctgcgcgaag |
| 2851 | aggattttgt agccgagcgc gagggcttcg aacgccgtca gcaggaaatg |
| 2901 | gaagccgctg ataccgaacc gtttgcggtg tggctggaaa aacacgcctg |
| 2951 | aGGATCCTCT AGACTCGGAG GCTCTCAAGA TCAAAGGCTT AAAAAGCTGG |
| 3001 | GGTTTTATGA ATGGGATCAA AGTTTCTTTT TTTCTTTTAT ATTTGCTTCT |
| 3051 | CCATTTGTTT GTTTCATTTC CCTTTTTGTT TTCGTTTCTA TGATGCACTT |
| 3101 | GTGTGTGACA AACTCTCTGG GTTTTTACTT ACGTCTGCGT TTCAAAAAAA |
| 3151 | AAAACCGCTT TCGTTTTGCG TTTTAGTCCC ATTGTTTTGT AGCTCTGAGT |
| 3201 | GATCGAATTG ATGCCTCTTT ATTCCTTTTG TTCCCTATAA TTTCTTTCAA |
| 3251 | AACTCAGAAG AAAAACCTTG AAACTCTTTG CAATGTTAAT ATAAGTATTG |
| 3301 | TATAAGATTT TTATTGATTT GGTTATTAGT CTTACTTTTG CTACCTCCAT |
| 3351 | CTTCACTTGG AACTGATATT CTGAATAGTT AAAGCGTTAC ATGTCTTCCA |
| 3401 | TTCACAAATG AACTTAAACT AGCACAAAGT CAGATATTTT AAGAGAATTC |

TABLE 8

Bacterial glutathione synthetase (Gs) coding sequence (954 nucleotides) was cloned into NcoI/BamH1 restriction sites between ACT2 promoter and ACT2 terminater in pBluescript (II) KS (SEQ ID NO: 18)

| | |
|---|---|
| 1 | AAGCTTGCAT GCTGATCTCA AATACATTGA TACATATCTC ATCTAGATCT |
| 51 | AGGTTATCAT TATGTAAGAA AGTTTTGACG AATATGGCAC GACAAAATGG |
| 101 | CTAGACTCGA TGTAATTGGT ATCTCAACTC AACATTATAC TTATACCAAA |
| 151 | CATTAGTTAG ACAAAATTTA AACAACTATT TTTTATGTAT GCAAGAGTCA |
| 201 | GCATATGTAT AATTGATTCA GAATCGTTTT GACGAGTTCG GATGTAGTAG |
| 251 | TAGCCATTAT TTAATGTACA TACTAATCGT GAATAGTGAA TATGATGAAA |
| 301 | CATTGTATCT TATTGTATAA ATATCCATAA ACACATCATG AAAGACACTT |
| 351 | TCTTTCACGG TCTGAATTAA TTATGATACA ATTCTAATAG AAAACGAATT |
| 401 | AAATTACGTT GAATTGTATG AAATCTAATT GAACAAGCCA ACCACGACGA |
| 451 | CGACTAACGT TGCCTGGATT GACTCGGTTT AAGTTAACCA CTAAAAAAAC |
| 501 | GGAGCTGTCA TGTAACACGC GGATCGAGCA GGTCACAGTC ATGAAGCCAT |
| 551 | CAAAGCAAAA GAACTAATCC AAGGGCTGAG ATGATTAATT AGTTTAAAAA |
| 601 | TTAGTTAACA CGAGGGAAAA GGCTGTCTGA CAGCCAGGTC ACGTTATCTT |
| 651 | TACCTGTGGT CGAAATGATT CGTGTCTGTC GATTTTAATT ATTTTTTTGA |
| 701 | AAGGCCGAAA ATAAAGTTGT AAGAGATAAA CCCGCCTATA TAAATTCATA |
| 751 | TATTTTCCTC TCCGCTTTGA ATTGTCTCGT TGTCCTCCTC ACTTTCATCA |
| 801 | GCCGTTTTGA ATCTCCGGCG ACTTGACAGA GAAGAACAAG GAAGAAGACT |
| 851 | AAGAGAGAAA GTAAGAGATA ATCCAGGAGA TTCATTCTCC GTTTTGAATC |
| 901 | TTCCTCAATC TCATCTTCTT CCGCTCTTTC TTTCCAAGGT AATAGGAACT |

TABLE 8-continued

Bacterial glutathione synthetase (Gs) coding sequence (954 nucleotides) was cloned into NcoI/ BamH1 restriction sites between ACT2 promoter and ACT2 terminater in pBluescript (II) KS
(SEQ ID NO: 18)

```
 951 TTCTGGATCT ACTTTATTTG CTGGATCTCG ATCTTGTTTT
     CTCAATTTCC

1001 TTGAGATCTG GAATTCGTTT AATTTGGATC TGTGAACCTC
     CACTAAATCT

1051 TTTGGTTTTA CTAGAATCGA TCTAAGTTGA CCGATCAGTT
     AGCTCGATTA

1101 TAGCTACCAG AATTTGGCTT GACCTTGATG GAGAGATCCA
     TGTTCATGTT

1151 ACCTGGGAAA TGATTTGTAT ATGTGAATTG AAATCTGAAC
     TGTTGAAGTT

1201 AGATTGAATC TGAACACTGT CAATGTTAGA TTGAATCTGA
     ACACTGTTTA

1251 AGGTTAGATG AAGTTTGTGT ATAGATTCTT CGAAACTTTA
     GGATTTGTAG

1301 TGTCGTACGT TGAACAGAAA GCTATTTCTG ATTCAATCAG
     GGTTTATTTG

1351 ACTGTATTGA ACTCTTTTTG TGTGTTTGCA GCTCATAAAC
     CATGGcaatc 1401 aagctcggca tcgtgatgga ccccatcgca aacatcaaca
     tcaagaaaga 1451 ttccagtttt gctatgttgc tggaagcaca gcgtcgtggt
     tacaacttca ACT2pG5ACT2term.txt 1501 ctatatggag atgggcgatc tgtatctgat caatggtgaa
     gcccgcgccc 1551 atcccgcacg ctgaacgtga agcagaacta cgaagagtgg
     ttttcgttcg 1601 tcggtgaaca gatctgccgc tggccgatct cgatgtgatc
     ctgatgcgta 1651 aagacccgcc gtttgatacc agtttatcta cgcgacctat
     attctggaac 1701 gtgccgaaga gaaagggacg ctgatcgtta caagccgcag
     agcctgcgcg 1751 actgtaacga gaaactgttt accgcctggt tctctgacta
     acgccagaaa 1801 cgctggttac gcgcaataaa gcgcagctaa aagcgttctg
     ggagaaaaca 1851 gcgacatcat tcttaagccg ctggacggta tgggcggcgc
     gtcgattttc 1901 cgcgtgaaga aggcgatcca aacctcggcg tgattgccga
     aaccctgact 1951 gagcatggca ctcgcactgc atggcgcaaa attacctgcc
     agccattaaa 2001 gatggcgaca aacgcgtgct ggtgtggatg gcgagccggt
     accgtactgc 2051 ctggcgcgta ttccgcaggg gggcgaaacc cgtgcaatct
     ggctgccggt 2101 ggtcgcggtg aacctcgtcc gctgacggaa agtgactgga
     aatcgcccgt 2151 cagatcgggc cgacgctgaa agaaaaaggg ctgattttg
     ttggtctgga 2201 ttcatcggcg accgtctgac tgaaattaac gtcaccagcc
     caacctgtat 2251 tcgtgagatt aagcagagtt ccggtgtcg atcaccggaa
     tgttaatgga 2301 tgccatcgaa gcacgtttaa gcagcagtaa cccacccttag
     cgagaaggat 2351 ctcgttgaGG ATCCTCTAGA CTCGGAGGCT CTCAAGATCA
     AAGGCTTAAA

2401 AGCTGGGGT TTTATGAATG GGATCAAAGT TTCTTTTTTT
     CTTTTATATT

2451 TGCTTCTCCA TTTGTTTGTT TCATTTCCCT TTTTGTTTTC
     GTTTCTATGA

2501 TGCACTTGTG TGTGACAAAC TCTCTGGGTT TTTACTTACG
     TCTGCGTTTC

2551 AAAAAAAAAA ACCGCTTTCG TTTTGCGTTT TAGTCCCATT
     GTTTTGTAGC

2601 TCTGAGTGAT CGAATTGATG CCTCTTTATT CCTTTTGTTC
     CCTATAATTT

2651 CTTTCAAAAC TCAGAAGAAA AACCTTGAAA CTCTTTGCAA
     TGTTAATATA

2701 AGTATTGTAT AAGATTTTTA TTGATTTGGT TATTAGTCTT
     ACTTTTGCTA

2751 CCTCCATCTT CACTTGGAAC TGATATTCTG AATAGTTAAA
     GCGTTACATG

2801 TCTTCCATTC ACAAATGAAC TTAAACTAGC ACAAAGTCAG
     ATATTTTAAG

2851 AGAATTC
```

What is claimed is:

1. A method for producing a transgenic plant which is resistant to at least one metal ion, said method comprising the steps of:
   (a) introducing a nucleic acid molecule comprising a bacterial arsenate reductase coding sequence operably linked to a plant expressible transcription regulatory sequence, into a plant cell or into plant tissue to produce a transformed plant cell or transformed plant tissue;
   (b) introducing at least one plant expressible phytochelatin biosynthetic enzyme coding sequence into the transgenic plant cell or transgenic tissue, wherein said phytochelatin biosynthetic enzyme is selected from the group consisting of gamma-glutamyl-cysteine synthase, phytochelatin synthase or glutathione synthase; and
   (c) regenerating a transgenic plant from the transgenic plant cell or transgenic plant tissue, whereby a metal ion resistant plant is produced.

2. The method of claim 1, wherein the metal ion is arsenate and wherein the transcription regulatory sequence is a light regulated promoter.

3. The method of claim 1, wherein the at least one phytochelatin biosynthetic enzyme coding sequence is expressed under the regulatory control of a plant ACT2 promoter or a plant SRS1 promoter.

4. The method of claim 3, wherein the at least one phytochelatin biosynthetic enzyme coding sequence is expressed under the regulatory control of an *Arabidopsis thaliana* ACT2 promoter.

5. The method of claim 4, wherein an arsenate reductase coding sequence is expressed under the control of a plant promoter which directs expression in an above ground plant part.

6. The method of claim 5, wherein the arsenate reductase coding sequence is expressed under the control of a *Glycine max* SRS1 promoter, whereby a plant resistant to arsenate is produced.

7. The method of claim 2, wherein the transgenic plant is further resistant to cadmium, cobalt, copper, mercury, zinc, and arsenite ions.

8. A transgenic plant produced by the method of claim 1.

9. A method for phytoremediation of soil, groundwater, industrial waste or water contaminated with at least one metal ion selected from the group consisting of copper, cobalt, zinc, mercury, arsenate and arsenite, said method comprising the step of contacting the plant of claim 8 with the soil, groundwater, industrial waste or water contaminated with at least one metal ion selected from the group consisting of copper, cobalt, zinc, mercury, arsenate and arsenite; whereby the plant hyperaccumulates the at least one metal ion.

10. The method of claim 9, wherein said transgenic plant is a dicotyledonous plant.

11. The method of claim 10, wherein said transgenic plant is a member of the Solanaceae.

12. The method of claim 10, wherein said transgenic plant is *Arabidopsis*.

13. The method of claim 10, wherein the plant is a poplar or a cottonwood.

14. The method of claim 9, wherein said transgenic plant is a monocotyledonous plant.

15. The method of claim 9, wherein said transgenic plant is a gymnosperm.

16. The method of claim 11, wherein said transgenic plant is a member of the Coniferae.

* * * * *

SEQUENCE LISTING

<160> NUMBER OF SEQ ID NOS: 18

<210> SEQ ID NO 1
<211> LENGTH: 56
<212> TYPE: DNA

<213> ORGANISM: Artificial Sequence
<220> FEATURE:
<223> OTHER INFORMATION: Description of Artificial Sequence: Synthetic
      nucleotide primer

<400> SEQUENCE: 1
tacgtcggat ccgaattcgt cgactaagga ggagccacaa tgagcaacat cactat         56

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      nucleotide primer

<400> SEQUENCE: 2
taggtcggat aagaattcaa gcttattatt tcagccgttt                           40

<210> SEQ ID NO 3
<211> LENGTH: 4347
<212> TYPE: DNA
<213> ORGANISM: Plasmid R773
<220> FEATURE:
<221> NAME/KEY: CDS
<222> LOCATION: (3286)..(3708)
<223> OTHER INFORMATION: This CDS encodes for ArsC, arsenate reductase.

<400> SEQUENCE: 3
agcttccggg gcagaaggtc tgccattgtt gttactggat ggcgaaacag tgatggccgg      60
gcgttacccg aaacgcgctg agctggctcg ctggtttggc attccactgg ataaagtggg     120
attagcgcct tcaggttgct gtggtggtaa tacttcttgt tgttaagtat atcaggagga     180
catatgcaat tcttacagaa tatccccccct tatctgtttt ttacgggtaa aggaggcgtg     240
ggtaaaacct ctatttcctg cgccacggcg atccgtctgg cagaacaggg gaaacgggtg     300
ctgctggtca gtaccgatcc ggcctcaaac gtaggccagg tgtttagcca gacgattggc     360
attaccattc aggcaatagc ctctgttcct ggattgtcgg ctcttgagat tgatcctcag     420
gctgctgcac aacagtaccg ggccagaatc gttgaccta ttaaaggcgt cctgcctgat     480
gacgttgttt ccagcatcaa cgaacaactg tcaggtgcat gcacaacaga gattgcggct     540
tttgatgaat ttaccggatt actgacagat gcctctctgc tgacgcggtt tgaccatatc     600
atttttgata ccgcgccgac gggtcacacc attcgccttc tgcagttgcc gggcgcctgg     660
agtagcttta ttgacagcaa tcccgagggc gcgtcctgtc tcggcccaat ggcggggctg     720
gaaaagcagc gtgaacagta tgcctatgct gttgaagcgt tgtctgatcc aaagcgtacc     780
cgactggtat tagttgctcg tctgcaaaaa tccacgttgc aggaagtcgc ccggactcat     840
ctggaacttg ccgccatcgg ccttaaaaat cagtacctgg ttattaatgg cgttctgccc     900
aaaactgaag cggcaaacga tacactggct gctgcaatat gggagcgtga acaggaggcg     960
ctggccaatc ttcccgctga tcttgcaggt ttgccaactg acacattatt tctccagccg    1020
gtcaatatgg tcggtgtgtc tgcgctcagc aggcttctct ccactcagcc gtagcgtcg     1080 ccatcctcgg atgaatacct gcaacagcgg cctgatattc cgtcactttc tgcgttggtt    1140
gatgatattg cccgtaatga acatggcctg attatgctga tgggtaaagg tggcgtgggg    1200
aaaaccacga tggctgctgc cattgctgtc aggctggccg acatgggatt tgatgtccat    1260
ctgacaacat ctgatcctgc ggcgcatctc agcatgaccc tgaacggtag ccttaacaac    1320
ctgcaggtca gcaggatcga tcctcacgag gaaacggaac gctatcgtca gcatgttctt    1380

-continued

```
gaaacaaagg gaaagaact  ggacgaagcg ggaaaacgcc tgctggaaga ggacttacgc   1440
tcaccttgca ctgaggaaat tgctgttttc caggcctttt cacgggtgat tcgtgaagcg   1500
ggtaaacgtt tcgtggtgat ggatacggct ccgaccggac acacgctgtt gctgctggat   1560
gctacaggcg cgtaccaccg cgaaattgcg aagaaaatgg gagaaaaagg ccatttcacc   1620
acaccgatga tgctgcttca ggatccggag cgcactaaag tgttactggt cacgctgccg   1680
gaaaccacgc ccgtgcttga agcggcaaat ttacaggccg accttgagcg tgcaggcatt   1740
cacccctggg gctggattat caataacagc ctttccattg cggatacccg ttcgccactg   1800
cttcgtatgc gggcacaaca ggaacttccg cagatagaga gcgttaaacg ccagcacgcc   1860
agccgtgtcg ctcttgttcc cgtactggcg tcagaaccaa ccggcatcga caaactcaaa   1920
caacttgctg gtaaattat  tgtcatcacg tagggcagca aagctgccct gtcaggaggt   1980
tttatgttac tggcaggagc cattttatc  ctgaccatcg ttttggttat ctggcagccg   2040
aaaggattag ggattggctg gagcgccacg ttggggctg  tactggctct ggcgtcgggt   2100
gtgatacaca ttgctgatat tccggtggtg tggaatattg tctggaacgc gacggcaaca   2160
tttatcgccg ttattatcat cagcctgttg ctggatgagt caggcttttt cgaatgggca   2220
gcgttgcacg tttctcgctg ggggaacggt cgtggccgcc tgctgtttac gtatattgtt   2280
ctgctcggcg cggcagtggc ggcactgttt gccaacgatg tgcggctct  tattctgacg   2340
ccgattgtta tcgccatgct gctggcgctt ggcttcagta aaagcaccac actggcattc   2400
gtgatggctg ccgggtttat ttccgatact gctagcttgc cgcttatcgt atcgaacttg   2460
gtcaatatcg tttcagctga tttcttcaaa ctgggattca cggagtatgc ttcggtgatg   2520
gtgccggtgg atatcgccgc cattatcgcc acgctggtga tgctgcatct ttttttccgc   2580
aaagatatcc cccccactta tgagctggcg cgactgaaag aacctgcaaa agccatcaaa   2640
gatcctgcga cgttcagaac cggctgggtt gttctcctcc ttctgctggt cggttttttt   2700
gtccttgagc cgatggggat ccctgtgagt gcgattgcag cagtggggc  ggcagtcctg   2760
tttgcggtgg ccaaaaaagg tcatggtatt aacaccggta agtgctgcg  cggcgcgccc   2820
tggcagatcg tgatcttctc tctggggatg tatctggtga tctacggggtt gcgtaacgcc   2880
ggtctgacag attatctctc tgacgtgctg aacgaactgg cagataaagg actgtgggcc   2940
gccacgctgg ggacgggatt cctgacagca ttactctctt ctattatgaa caatatgccg   3000
acagtattga ttggcgcatt gtcaattgat ggcagcaccg cgaccggtgt tatcaaagag   3060
gcgatgattt atgccaacgt cattggctgc gatctggggc cgaaaatcac ccctattggt   3120
agcctggcaa cactgctctg gctgcatgta ctttcacaga agaacatgac catcacttgg   3180
ggatactatt tccgcaccgg gatcgtcatg actctgcctg tgctgtttgt aacgctggcc   3240
gcgctggcgc tacgtctctc tgtcacattg taatgagatt ctgat atg agc aac atc   3297
                                              Met Ser Asn Ile
                                               1
act att tat cat aac cca gcc tgc ggc acc tcg cgt aat acg ctg gag   3345
Thr Ile Tyr His Asn Pro Ala Cys Gly Thr Ser Arg Asn Thr Leu Glu
  5                  10                  15                  20
atg atc cgc aac agc ggt acc gag ccg acc att att ctt tac ctt gaa   3393
Met Ile Arg Asn Ser Gly Thr Glu Pro Thr Ile Ile Leu Tyr Leu Glu
             25                  30                  35
aac ccg cct tcg agg gat gag ctg gtt aaa ctt att gcc gat atg ggt   3441
Asn Pro Pro Ser Arg Asp Glu Leu Val Lys Leu Ile Ala Asp Met Gly
         40                  45                  50
```

```
att tca gta cga gcg ctg ctg cgt aaa aac gtt gaa cct tac gag caa    3489
Ile Ser Val Arg Ala Leu Leu Arg Lys Asn Val Glu Pro Tyr Glu Gln
        55                  60                  65 ctg ggt ctt gca gaa gat aaa ttt act gac gat cag ctc atc gac ttt    3537
Leu Gly Leu Ala Glu Asp Lys Phe Thr Asp Asp Gln Leu Ile Asp Phe
 70                  75                  80 atg ttg caa cac cca att ctg att aac cgt ccg atc gtg gtt acg ccg    3585
Met Leu Gln His Pro Ile Leu Ile Asn Arg Pro Ile Val Val Thr Pro
 85                  90                  95                 100 ctg gga acc aga ctg tgc cgt cct tct gaa gtg gtt ctg gat atc cta    3633
Leu Gly Thr Arg Leu Cys Arg Pro Ser Glu Val Val Leu Asp Ile Leu
                105                 110                 115 cag gat gcg cag aaa ggg gct ttc act aag gaa gac ggt gaa aaa gtc    3681
Gln Asp Ala Gln Lys Gly Ala Phe Thr Lys Glu Asp Gly Glu Lys Val
        120                 125                 130 gtt gat gaa gca gga aaa cgg ctg aaa taataataa gggggcgaat           3728
Val Asp Glu Ala Gly Lys Arg Leu Lys
        135                 140 gccccttat tcgtacctca gagcatcatg cctgaatccg atggtaacgt gctgttccct    3788
tcgcccagat ttcgttgcag caacactgtg tcaagccaac gaccatgctt gaagccaata    3848
tttttcagcg taccaatctc agtaaatcca acctgctgat ggactttcag cgaaccttga    3908
ttattgctat cgccgacaat agcaatcatc tgccgatagc cgtgagtttt tgcccaggaa    3968
atgacgtagc gcagcaacgc ttttcctgtc ccccgacgct gtgcgtccgg gtgaatataa    4028
atcgaatctt cgagagtgtg gcggtaggcg tagcgttcac ggtaacgagt gagataacaa    4088
tacccgataa cctttcttc ctctaacgtg acaacccacg gtagctcctg attgcggatc     4148
tttttcaggc gggcaagcat ctcgtgggta tccggaggtt cagtttcaaa gctggcggta    4208
ccgtgaagaa catgatgggc gtagatatcg cgtatagcgg ggatgtgctt tcttctgcg    4268 ttaacgattt tcattgttct gttcccgttg gcatcttttt caaggttact tgaaaatcca    4328
gaggaaaggt aaatacaaa                                                 4347

<210> SEQ ID NO 4
<211> LENGTH: 141
<212> TYPE: PRT
<213> ORGANISM: Plasmid R773

<400> SEQUENCE: 4

Met Ser Asn Ile Thr Ile Tyr His Asn Pro Ala Cys Gly Thr Ser Arg
 1               5                  10                  15

Asn Thr Leu Glu Met Ile Arg Asn Ser Gly Thr Glu Pro Thr Ile Ile
            20                  25                  30

Leu Tyr Leu Glu Asn Pro Pro Ser Arg Asp Glu Leu Val Lys Leu Ile
        35                  40                  45

Ala Asp Met Gly Ile Ser Val Arg Ala Leu Leu Arg Lys Asn Val Glu
    50                  55                  60

Pro Tyr Glu Gln Leu Gly Leu Ala Glu Asp Lys Phe Thr Asp Asp Gln
65                  70                  75                  80

Leu Ile Asp Phe Met Leu Gln His Pro Ile Leu Ile Asn Arg Pro Ile
                85                  90                  95

Val Val Thr Pro Leu Gly Thr Arg Leu Cys Arg Pro Ser Glu Val Val
            100                 105                 110

Leu Asp Ile Leu Gln Asp Ala Gln Lys Gly Ala Phe Thr Lys Glu Asp
        115                 120                 125

Gly Glu Lys Val Val Asp Glu Ala Gly Lys Arg Leu Lys
    130                 135                 140
```

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: Synthetic
      nucleotide primer

<400> SEQUENCE: 5
cacagcctcg agtaaggagg aggagccacc atggcaatcc cggacgtatc acaggcgct    59

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: Synthetic
      nucleotide primer

<400> SEQUENCE: 6
gagtcgggat ccaagctttc aggcgtgttt ttccagccac accgcaa                 47

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      nucleotide primer

<400> SEQUENCE: 7
cgagccctcg agtaaggagc caccatggca atcaagctcg gcatcgtgat ggaccccat    59

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      nucleotide primer

<400> SEQUENCE: 8
acgtgcggat ccaagcttat tactgctgct gtaaacgtgc ttcgat                  46

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      nucleotide primer

<400> SEQUENCE: 9
cgagcgctcg agtaaggagg agccaccatg gcaaccaatg caacaccaaa tatcggt      57

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      nucleotide primer

<400> SEQUENCE: 10
cgagcgggat ccgagctctc acgtattttt acagcagctt gaacta                  46

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ile Pro Asp Val Ser Gln Ala Leu Ala Trp Leu Glu Lys His Pro Gln
 1               5                  10                  15
Ala Leu Lys Gly Ile Gln Arg Gly Leu Glu Arg Glu Thr Leu
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ile Lys Leu Gly Ile Val Met Asp Pro Ile Ala Asn Ile Asn Ile Lys
 1               5                  10                  15
Lys Asp Ser Ser Phe Ala Met Leu Leu Glu Ala Gln Arg Arg
            20                  25                  30

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Asn Ile Val Lys Arg Ala Val Pro Glu Leu Leu Arg Gly Met Thr Asn
 1               5                  10                  15
Ala Thr Pro Asn Ile Gly Leu Ile Lys Asn Lys Val Val
            20                  25

<210> SEQ ID NO 14
<211> LENGTH: 4526
<212> TYPE: DNA
<213> ORGANISM: Artificial Sequence
<220> FEATURE:
<223> OTHER INFORMATION: Description of Artificial Sequence: Plasmid pACT2B
<220> FEATURE:
<221> NAME/KEY: misc_feature
<222> LOCATION: (1)..(4526)
<223> OTHER INFORMATION: N is A, T, G or C and R is A or T.

<400> SEQUENCE: 14
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagcttgc     240
atgcctgcag gtcgacatta tgatctcaaa tacattgata catatctcat ctagatctag     300
gttatcatta tgtaagaaag ttttgacgaa tatgnnacga caaaatggct agactcgatg     360

-continued

```
taattggtat ctcaactcaa cattatactt ataccaaaca ttagttagca aaatttaaac    420 aactatttt  atgtatgcaa gagtcagcat atgtataatt gattcagaat cgttttgacg    480
agttcggatg tagtagtagc cattatttaa tgtacatact aatcgtgaat agtgatatga    540
tgaaacattg tatcttattg tataaatatc cataaacaca tcatgaaaga cactttcttt    600
cacggtctga attaattatg atacaattct aatagaaaac gaattaaatt acgttgaatt    660
gtatgaaatc taattgaaca agccaaccac gacgacgact aacgttgcct ggattgactc    720
ggtttaagtt aaccactaaa aaacggagc  tgtcatgtaa cacgcggatc gagcaggtca    780
cagtcatgaa gccatcaaag caaagaact   aatccaaggg ctgagatgat taattagttt    840
aaaaattagt taacacgagg gaaaaggctg tctgacagcc aggtcacgtt atctttacct    900
gtggtcgaaa tgattcgtgt ctgtcgattt taattatttt tttgaaaggc cgaaaataaa    960
gttgtaagag ataaacccgc ctatataaat tcatatattt tcctctccgc tttgaattgt   1020
ctcgttgtcc tcctcacttt catcagccgt tttgaatctc cggcgacttg acagagaaga   1080
acaaggaaga agactaagag agaaagtaag agataatcca ggagattcat tctccgtttt   1140
gaatcttcct caatctcatc ttcttccgct ctttctttcc aaggtaatag gaactttctg   1200
gatctacttt atttgctgga tctcgatctt gttttctcaa tttccttgag atctggaatt   1260
cgtttaattt ggatctgtga acctccacta aatcttttgg ttttactaga atcgatctaa   1320
gttgaccgat cagttagctc gattatagct accagaattt ggcttgacct tgatggagag   1380
atccatgttc atgttacctg ggaaatgatt tgtatatgtg aattgaaatc tgaactgttg   1440
aagttagatt gaatctgaac actgtcaatg ttagattgaa tctgaacact gtttaagtta   1500
gatgaagttt gtgtatagat tcttcgaaac tttaggatt  gtagtgtcgt acgttgaaca   1560
gaaagctatt tctgattcaa tcagggttta tttgactgta ttgaactctt tttgtgtgtt   1620
tgcagctcat aaaggatccc gggctcgaga agcttgcggc cgccatggta agctctcaag   1680
atcaaaggct taaaaagctg gggttttatg aatgggatca aagtttcttt ttttcttta    1740 tatttgcttc tccatttgtt tgtttcattt ccctttttgt tttcgtttct atgatgcact   1800
tgtgtgtgac aaactctctg ggttttact  tacgtctgcg tttcaaaaaa aaaaaccgct   1860
ttcgttttgc gttttagtcc cattgttttg tagctctgag tgatcgaatt gatgcctctt   1920
tattcctttt gttccctata atttctttca aaactcagaa raaaaacctt gaaactcttt   1980
gcaatgttaa tataagtatt gtataagatt tttattgatt tggttattag tcttactttt   2040
gctacctcca tcttcacttg gaactgatat tctgaatagt taaagcgtta catgtcttcc   2100
attcacaaat gaacttagag ctcgaattca ctggccgtcg ttttacaacg tcgtgactgg   2160
gaaaaccctg gcgttaccca acttaatcgc cttgcagcac atccccctt  cgccagctgg   2220 cgtaatagcg aagaggcccg caccgatcgc ccttcccaac agttgcgcag cctgaatggc   2280
gaatggcgcc tgatgcggta ttttctcctt acgcatctgt gcggtatttc acaccgcata   2340
tggtgcactc tcagtacaat ctgctctgat gccgcatagt taagccagcc ccgacacccg   2400
ccaacacccg ctgacgcgcc ctgacgggct tgtctgctcc cggcatccgc ttacagacaa   2460
gctgtgaccg tctccgggag ctgcatgtgt cagaggtttt caccgtcatc accgaaacgc   2520
gcgagacgaa agggcctcgt gatacgccta tttttatagg ttaatgtcat gataataatg   2580
gtttcttaga cgtcaggtgg cacttttcgg ggaaatgtgc gcggaacccc tatttgttta   2640
tttttctaaa tacattcaaa tatgtatccg ctcatgagac aataaccctg ataaatgctt   2700
caataatatt gaaaaaggaa gagtatgagt attcaacatt tccgtgtcgc ccttattccc   2760
```

```
tttttttgcgg cattttgcct tcctgttttt gctcacccag aaacgctggt gaaagtaaaa      2820
gatgctgaag atcagttggg tgcacgagtg ggttacatcg aactggatct caacagcggt      2880
aagatccttg agagttttcg ccccgaagaa cgttttccaa tgatgagcac ttttaaagtt      2940
ctgctatgtg gcgcggtatt atcccgtatt gacgccgggc aagagcaact cggtcgccgc      3000
atacactatt ctcagaatga cttggttgag tactcaccag tcacagaaaa gcatcttacg      3060
gatggcatga cagtaagaga attatgcagt gctgccataa ccatgagtga taacactgcg      3120
gccaacttac ttctgacaac gatcggagga ccgaaggagc taaccgcttt tttgcacaac      3180
atgggggatc atgtaactcg ccttgatcgt tgggaaccgg agctgaatga agccatacca      3240
aacgacgagc gtgacaccac gatgcctgta gcaatggcaa caacgttgcg caaactatta      3300
actggcgaac tacttactct agcttcccgg caacaattaa tagactggat ggaggcggat      3360
aaagttgcag gaccacttct gcgctcggcc cttccggctg gctggtttat tgctgataaa      3420
tctggagccg gtgagcgtgg gtctcgcggt atcattgcag cactggggcc agatggtaag      3480
ccctcccgta tcgtagttat ctacacgacg gggagtcagg caactatgga tgaacgaaat      3540
agacagatcg ctgagatagg tgcctcactg attaagcatt ggtaactgtc agaccaagtt      3600
tactcatata tactttagat tgatttaaaa cttcattttt aatttaaaag gatctaggtg      3660
aagatccttt ttgataatct catgaccaaa atcccttaac gtgagttttc gttccactga      3720
gcgtcagacc ccgtagaaaa gatcaaagga tcttcttgag atcctttttt tctgcgcgta      3780
atctgctgct tgcaaacaaa aaaaccaccg ctaccagcgg tggtttgttt gccggatcaa      3840
gagctaccaa ctctttttcc gaaggtaact ggcttcagca gagcgcagat accaaatact      3900
gtccttctag tgtagccgta gttaggccac cacttcaaga actctgtagc accgcctaca      3960
tacctcgctc tgctaatcct gttaccagtg gctgctgcca gtggcgataa gtcgtgtctt      4020
accgggttgg actcaagacg atagttaccg gataaggcgc agcggtcggg ctgaacgggg      4080
ggttcgtgca cacagcccag cttggagcga acgacctaca ccgaactgag atacctacag      4140
cgtgagctat gagaaagcgc cacgcttccc gaagggagaa aggcggacag gtatccggta      4200
agcggcaggg tcggaacagg agagcgcacg agggagcttc caggggggaaa cgcctggtat      4260 ctttatagtc ctgtcgggtt tcgccacctc tgacttgagc gtcgattttt gtgatgctcg      4320
tcaggggggc ggagcctatg gaaaaacgcc agcaacgcgg cctttttacg gttcctggcc      4380
ttttgctggc cttttgctca catgttcttt cctgcgttat cccctgattc tgtggataac      4440
cgtattaccg cctttgagtg agctgatacc gctcgccgca gccgaacgac cgagcgcagc      4500
gagtcagtga gcgaggaagc ggaaga                                          4526
```

```
<210> SEQ ID NO 15
<211> LENGTH: 6385
<212> TYPE: DNA
<213> ORGANISM: Artificial Sequence
<220> FEATURE:
<223> OTHER INFORMATION: Description of Artificial Sequence: Plasmid
      pACT2B-GUS
<220> FEATURE:
<221> NAME/KEY: misc_feature
<222> LOCATION: (1)..(6385)
<223> OTHER INFORMATION: N is A, T, G or C and R is A or T.

<400> SEQUENCE: 15
gcgcccaata cgcaaaccgc ctctccccgc gcgttggccg attcattaat gcagctggca        60
cgacaggttt cccgactgga aagcgggcag tgagcgcaac gcaattaatg tgagttagct       120
```

-continued

```
cactcattag gcaccccagg ctttacactt tatgcttccg gctcgtatgt tgtgtggaat    180
tgtgagcgga taacaatttc acacaggaaa cagctatgac catgattacg ccaagcttgc    240
atgcctgcag gtcgacatta tgatctcaaa tacattgata catatctcat ctagatctag    300
gttatcatta tgtaagaaag ttttgacgaa tatgnnacga caaaatggct agactcgatg    360
taattggtat ctcaactcaa cattatactt ataccaaaca ttagttagca aaatttaaac    420
aactattttt atgtatgcaa gagtcagcat atgtataatt gattcagaat cgttttgacg    480
agttcggatg tagtagtagc cattatttaa tgtacatact aatcgtgaat agtgatatga    540
tgaaacattg tatcttattg tataaatatc cataaacaca tcatgaaaga cactttcttt    600
cacggtctga attaattatg atacaattct aatagaaaac gaattaaatt acgttgaatt    660
gtatgaaatc taattgaaca agccaaccac gacgacgact aacgttgcct ggattgactc    720
ggtttaagtt aaccactaaa aaacggagc tgtcatgtaa cacgcggatc gagcaggtca    780
cagtcatgaa gccatcaaag caaaagaact aatccaaggg ctgagatgat taattagttt    840
aaaaattagt taacacgagg gaaaaggctg tctgacagcc aggtcacgtt atctttacct    900
gtggtcgaaa tgattcgtgt ctgtcgattt taattatttt tttgaaaggc cgaaaataaa    960
gttgtaagag ataaacccgc ctatataaat tcatatattt tcctctccgc tttgaattgt   1020
ctcgttgtcc tcctcacttt catcagccgt tttgaatctc cggcgacttg acagagaaga   1080
acaaggaaga agactaagag agaaagtaag agataatcca ggagattcat tctccgtttt   1140
gaatcttcct caatctcatc ttcttccgct ctttctttcc aaggtaatag gaactttctg   1200
gatctacttt atttgctgga tctcgatctt gttttctcaa tttccttgag atctggaatt   1260
cgtttaattt ggatctgtga acctccacta aatcttttgg ttttactaga atcgatctaa   1320
gttgaccgat cagttagctc gattatagct accagaattt ggcttgacct tgatggagag   1380
atccatgttc atgttacctg ggaaatgatt tgtatatgtg aattgaaatc tgaactgttg   1440
aagttagatt gaatctgaac actgtcaatg ttagattgaa tctgaacact gtttaagtta   1500
gatgaagttt gtgtatagat tcttcgaaac tttaggattt gtagtgtcgt acgttgaaca   1560
gaaagctatt tctgattcaa tcagggttta tttgactgta ttgaactctt tttgtgtgtt   1620
tgcagctcat aaaggatccc cgggtaggtc agtcccttat gttacgtcct gtagaaaccc   1680
caacccgtga atcaaaaaa ctcgacggcc tgtgggcatt cagtctggat cgcgaaaact   1740
gtggaattga tcagcgttgg tgggaaagcg cgttacaaga aagccgggca attgctgtgc   1800
caggcagttt taacgatcag ttcgccgatg cagatattcg taattatgcg ggcaacgtct   1860
ggtatcagcg cgaagtcttt ataccgaaag gttgggcagg ccagcgtatc gtgctgcgtt   1920
tcgatgcggt cactcattac ggcaaagtgt gggtcaataa tcaggaagtg atggagcatc   1980
agggcggcta tacgccattt gaagccgatg tcacgccgta tgttattgcc gggaaaagtg   2040
tacgtatcac cgtttgtgtg aacaacgaac tgaactggca gactatcccg ccgggaatgg   2100
tgattaccga cgaaaacggc aagaaaaagc agtcttactt ccatgatttc tttaactatg   2160
ccggaatcca tcgcagcgta atgctctaca ccacgccgaa cacctgggtg acgatatca   2220
ccgtggtgac gcatgtcgcg caagactgta accacgcgtc tgttgactgg caggtggtgg   2280
ccaatggtga tgtcagcgtt gaactgcgtg atgcggatca acaggtggtt gcaactggac   2340
aaggcactag cgggactttg caagtggtga atcgcaccct ctggcaaccg ggtgaaggtt   2400
atctctatga actgtgcgtc acagccaaaa gccagacaga gtgtgatatc tcaaagcttc   2460
```

```
gcgtcggcat ccggtcagtg gcagtgaagg gccaacagtt cctgattaac cacaaaccgt    2520
tctactttac tggctttggt cgtcatgaag atgcggactt acgtggcaaa ggattcgata    2580
acgtgctgat ggtgcacgac cacgcattaa tggactggat tggggccaac tcctaccgta    2640
cctcgcatta cccttacgct gaagagatgc tcgactgggc agatgaacat ggcatcgtgg    2700
tgattgatga aactgctgct gtcggcttta acctctcttt aggcattggt ttcgaagcgg    2760
gcaacaagcc gaaagaactg tacagcgaag aggcagtcaa cggggaaact cagcaagcgc    2820
acttacaggc gattaaagag ctgatagcgc gtgacaaaaa ccacccaagc gtggtgatgt    2880
ggagtattgc caacgaaccg atacccgtc cgcaagtgca cgggaatatt cgccactgg     2940 cggaagcaac gcgtaaactc gacccgacgc gtccgatcac ctgcgtcaat gtaatgttct    3000
gcgacgctca caccgatacc atcagcgatc tctttgatgt gctgtgcctg aaccgttatt    3060
acggatggta tgtccaaagc ggcgatttgg aaacggcaga aaggtactg gaaaagaac     3120 ttctggcctg gcaggagaaa ctgcatcagc cgattatcat caccgaatac ggcgtggata    3180
cgttagccgg gctgcactca atgtacaccg acatgtggag tgaagagtat cagtgtgcat    3240
ggctggatat gtatcaccgc gtctttgatc gcgtcagcgc cgtcgtcggt gaacaggtat    3300
ggaatttcgc cgattttgcg acctcgcaag gcatattgcg cgttggcggt aacaagaaag    3360
ggatcttcac tcgcgaccgc aaaccgaagt cggcggcttt tctgctgcaa aaacgctgga    3420
ctggcatgaa cttcggtgaa aaaccgcagc agggaggcaa acaatgaatc aacaactctc    3480
ctggcgcacc atcgtcggct acagcctcgg gaattgctac cgcatggtaa gctctcaaga    3540
tcaaaggctt aaaaagctgg ggttttatga atgggatcaa agtttctttt tttcttttat    3600
atttgcttct ccatttgttt gtttcatttc ccttttttgtt ttcgtttcta tgatgcactt    3660
gtgtgtgaca aactctctgg gttttttactt acgtctgcgt ttcaaaaaaa aaaaccgctt    3720
tcgttttgcg tttagtccc attgttttgt agctctgagt gatcgaattg atgcctcttt     3780
attccttttg ttccctataa tttctttcaa aactcagaar aaaaaccttg aaactctttg    3840
caatgttaat ataagtattg tataagattt ttattgattt ggttattagt cttacttttg    3900
ctacctccat cttcacttgg aactgatatt ctgaatagtt aaagcgttac atgtcttcca    3960
ttcacaaatg aacttagagc tcgaattcac tggccgtcgt tttacaacgt cgtgactggg    4020
aaaaccctgg cgttacccaa cttaatcgcc ttgcagcaca tccccctttc gccagctggc    4080
gtaatagcga agaggcccgc accgatcgcc cttcccaaca gttgcgcagc ctgaatggcg    4140
aatggcgcct gatgcggtat tttctcctta cgcatctgtg cggtatttca caccgcatat    4200
ggtgcactct cagtacaatc tgctctgatg ccgcatagtt aagccagccc cgacacccgc    4260
caacacccgc tgacgcgccc tgacgggctt gtctgctccc ggcatccgct tacagacaag    4320
ctgtgaccgt ctccgggagc tgcatgtgtc agaggttttc accgtcatca ccgaaacgcg    4380
cgagacgaaa gggcctcgtg atacgcctat ttttataggt taatgtcatg ataataatgg    4440
tttcttagac gtcaggtggc acttttcggg gaaatgtgcg cggaacccct atttgtttat    4500
ttttctaaat acattcaaat atgtatccgc tcatgagaca ataaccctga taatgcttc     4560 aataatattg aaaaaggaag agtatgagta ttcaacattt ccgtgtcgcc cttattccct    4620
tttttgcggc attttgcctt cctgttttg ctcacccaga aacgctggtg aaagtaaaag     4680
atgctgaaga tcagttgggt gcacgagtgg gttacatcga actggatctc aacagcggta    4740
agatccttga gagttttcgc cccgaagaac gttttccaat gatgagcact tttaaagttc    4800
tgctatgtgg cgcggtatta tcccgtattg acgccgggca agagcaactc ggtcgccgca    4860
```

```
tacactattc tcagaatgac ttggttgagt actcaccagt cacagaaaag catcttacgg    4920
atggcatgac agtaagagaa ttatgcagtg ctgccataac catgagtgat aacactgcgg    4980
ccaacttact tctgacaacg atcggaggac cgaaggagct aaccgctttt ttgcacaaca    5040
tgggggatca tgtaactcgc cttgatcgtt gggaaccgga gctgaatgaa gccataccaa    5100
acgacgagcg tgacaccacg atgcctgtag caatggcaac aacgttgcgc aaactattaa    5160
ctggcgaact acttactcta gcttcccggc aacaattaat agactggatg gaggcggata    5220
aagttgcagg accacttctg cgctcggccc ttccggctgg ctggtttatt gctgataaat    5280
ctggagccgg tgagcgtggg tctcgcggta tcattgcagc actggggcca gatggtaagc    5340
cctcccgtat cgtagttatc tacacgacgg ggagtcaggc aactatggat gaacgaaata    5400
gacagatcgc tgagataggt gcctcactga ttaagcattg gtaactgtca gaccaagttt    5460
actcatatat actttagatt gatttaaaac ttcatttta atttaaaagg atctaggtga    5520 agatccttt tgataatctc atgaccaaaa tcccttaacg tgagttttcg ttccactgag    5580
cgtcagaccc cgtagaaaag atcaaaggat cttcttgaga tcctttttt ctgcgcgtaa    5640 tctgctgctt gcaaacaaaa aaaccaccgc taccagcggt ggtttgtttg ccggatcaag    5700
agctaccaac tctttttccg aaggtaactg gcttcagcag agcgcagata ccaaatactg    5760
tccttctagt gtagccgtag ttaggccacc acttcaagaa ctctgtagca ccgcctacat    5820
acctcgctct gctaatcctg ttaccagtgg ctgctgccag tggcgataag tcgtgtctta    5880
ccgggttgga ctcaagacga tagttaccgg ataaggcgca gcggtcgggc tgaacggggg    5940
gttcgtgcac acagcccagc ttggagcgaa cgacctacac cgaactgaga tacctacagc    6000
gtgagctatg agaaagcgcc acgcttcccg aagggagaaa ggcggacagg tatccggtaa    6060
gcggcagggt cggaacagga gagcgcacga gggagcttcc agggggaaac gcctggtatc    6120
tttatagtcc tgtcgggttt cgccacctct gacttgagcg tcgatttttg tgatgctcgt    6180
caggggggcg gagcctatgg aaaaacgcca gcaacgcggc ctttttacgg ttcctggcct    6240
tttgctggcc ttttgctcac atgttctttc ctgcgttatc ccctgattct gtggataacc    6300
gtattaccgc ctttgagtga gctgataccg ctcgccgcag ccgaacgacc gagcgcagcg    6360
agtcagtgag cgaggaagcg gaaga                                          6385
```

<210> SEQ ID NO 16
<211> LENGTH: 3408
<212> TYPE: DNA
<213> ORGANISM: Artificial Sequence
<220> FEATURE:
<223> OTHER INFORMATION: Description of Artificial Sequence: Plasmid
      pAtPCSACT2

<400> SEQUENCE: 16

```
aagcttgcat gctgatctca aatacattga tacatatctc atctagatct aggttatcat      60
tatgtaagaa agttttgacg aatatggcac gacaaaatgg ctagactcga tgtaattggt     120
atctcaactc aacattatac ttataccaaa cattagttag acaaaattta aacaactatt     180
ttttatgtat gcaagagtca gcatatgtat aattgattca gaatcgtttt gacgagttcg     240
gatgtagtag tagccattat ttaatgtaca tactaatcgt gaatagtgaa tatgatgaaa     300
cattgtatct tattgtataa atatccataa acacatcatg aaagacactt tctttcacgg     360
tctgaattaa ttatgataca attctaatag aaaacgaatt aaattacgtt gaattgtatg     420
aaatctaatt gaacaagcca accacgacga cgactaacgt tgcctggatt gactcggttt     480
```

```
aagttaacca ctaaaaaaac ggagctgtca tgtaacacgc ggatcgagca ggtcacagtc    540
atgaagccat caaagcaaaa gaactaatcc aagggctgag atgattaatt agtttaaaaa    600
ttagttaaca cgagggaaaa ggctgtctga cagccaggtc acgttatctt tacctgtggt    660
cgaaatgatt cgtgtctgtc gattttaatt attttttga aaggccgaaa ataaagttgt    720
aagagataaa cccgcctata taaattcata tattttcctc tccgctttga attgtctcgt    780
tgtcctcctc actttcatca gccgttttga atctccggcg acttgacaga agaacaag     840 gaagaagact aagagagaaa gtaagagata tccaggaga ttcattctcc gttttgaatc    900
ttcctcaatc tcatcttctt ccgctctttc tttccaaggt ataggaact ttctggatct    960 actttatttg ctggatctcg atcttgtttt ctcaatttcc ttgagatctg gaattcgttt   1020
aatttggatc tgtgaacctc cactaaatct tttggtttta ctagaatcga tctaagttga   1080
ccgatcagtt agctcgatta tagctaccag aatttggctt gaccttgatg gagagatcca   1140
tgttcatgtt acctgggaaa tgatttgtat atgtgaattg aaatctgaac tgttgaagtt   1200
agattgaatc tgaacactgt caatgttaga ttgaatctga acactgttta aggttagatg   1260
aagtttgtgt atagattctt cgaaacttta ggatttgtag tgtcgtacgt tgaacagaaa   1320
gctatttctg attcaatcag ggtttatttg actgtattga actcttttg tgtgtttgca    1380 gctcataaac catggcagct atggcgagtt tatatcggcg atctcttcct tctcctccgg   1440
ccattgactt tcttccgcc gaaggcaagc taatcttcaa tgaagcgctt caaaaggaa     1500 ctatggaagg attttttcagg ttgatttcgt attttcagac acaatccgaa cctgcgtatt  1560
gtggtttggc tagtctctca gtggtgttga atgctcttc tatcgatcct ggacgtaaat    1620
ggaaagggcc ttggaggtgg tttgatgaat caatgttgga ttgctgcgaa cctctggaag   1680
tagtgaagga aaaggcatt tcatttggaa aagttgtctg tttggctcat tgttcaggag    1740
caaaagttga ggctttccgt acaagtcaga gcaccattga tgatttccgc aaatttgtcg   1800
tcaaatgcac gagttctgag aattgtcata tgatctcaac atatcaccga agtgtattta   1860
agcagactgg gaatggtcac ttttcaccta ttggtggcta taatgctgag agagatatgg   1920
ctttgattct tgatgttgct cgtttcaagt atccccctca ctgggttcct cttaaacttc   1980
tttgggaagc catggacagt attgatcagt caacagggaa acgtagaggg ttcatgctca   2040
tatctagacc acacagagaa cccggattgc tctatactct gagctgcaag gatgaaagct   2100
ggatcgaaat agccaagtat ttgaaggaag atgttcctcg tcttgtaagt tcacagcatg   2160
tagattctgt ggagaaaatc atatcagttg tgttcaagtc acttccatca aatttcaacc   2220
aattcatcag atgggtggct gagatccgaa ttacagagga ctcaaaccaa aatctcagcg   2280
cagaggagaa gtctaggctg aaactaaagc aattggtgct gaaggaagtg cacgaaactg   2340
aactgttcaa acacatcaat aagttcttat ccacagtggg ttatgaagac agtctgactt   2400
atgctgctgc aaaggcttgt tgccaaggag ctgaaatctt atccggaagc ccatcaaaag   2460
agttttgttg tcgggaaact tgcgtgaaat gcatcaaagg tcctgatgac tctgaaggca   2520
cggtggtgac tggagttgtg gtgcgtgatg ggaatgaaca aaaggttgat ctgttagtgc   2580
catcgacgca aactgagtgt gaatgtggtc ctgaagcaac ttatccagca ggaaacgatg   2640
tgttcactgc acttctattg gctttacctc cacagacatg gtcagggatc aaagaccaag   2700
ctcttatgca tgaaatgaag cagctcattt ccatggcttc cctcccaact ttgcttcaag   2760
aagaggtatt gcatcttcga cggcaacttc agctgctaaa acgatgccaa gagaacaagg   2820
```

-continued

| | |
|---|---|
| aagaggatga tctcgctgct cctgcctatt agttcattgt cccaaatcct ctctcttccc | 2880 |
| catttgaatc ccacgttctc tacacttaag gatcctctag actcggaggc tctcaagatc | 2940 |
| aaaggcttaa aaagctgggg ttttatgaat gggatcaaag tttctttttt tcttttatat | 3000 |
| ttgcttctcc atttgtttgt ttcatttccc ttttttgtttt cgtttctatg atgcacttgt | 3060 |
| gtgtgacaaa ctctctgggt ttttacttac gtctgcgttt caaaaaaaaa aaccgctttc | 3120 |
| gttttgcgtt ttagtcccat tgttttgtag ctctgagtga tcgaattgat gcctcttat | 3180 |
| tccttttgtt ccctataatt tctttcaaaa ctcagaagaa aaaccttgaa actctttgca | 3240 |
| atgttaatat aagtattgta taagattttt attgatttgg ttattagtct tactttgct | 3300 |
| acctccatct tcacttggaa ctgatattct gaatagttaa agcgttacat gtcttccatt | 3360 |
| cacaaatgaa cttaaactag cacaaagtca gatattttaa gagaattc | 3408 |

<210> SEQ ID NO 17
<211> LENGTH: 3450
<212> TYPE: DNA
<213> ORGANISM: Artificial Sequence
<220> FEATURE:
<223> OTHER INFORMATION: Description of Artificial Sequence: Plasmid pECSACT2

<400> SEQUENCE: 17

| | |
|---|---|
| aagcttgcat gctgatctca aatacattga tacatatctc atctagatct aggttatcat | 60 |
| tatgtaagaa agttttgacg aatatggcac gacaaaatgg ctagactcga tgtaattggt | 120 |
| atctcaactc aacattatac ttataccaaa cattagttag acaaaattta aacaactatt | 180 |
| ttttatgtat gcaagagtca gcatatgtat aattgattca gaatcgtttt gacgagttcg | 240 |
| gatgtagtag tagccattat ttaatgtaca tactaatcgt gaatagtgaa tatgatgaaa | 300 |
| cattgtatct tattgtataa atatccataa acacatcatg aaagacactt tctttcacgg | 360 |
| tctgaattaa ttatgataca attctaatag aaaacgaatt aaaattacgtt gaattgtatg | 420 |
| aaatctaatt gaacaagcca accacgacga cgactaacgt tgcctggatt gactcggttt | 480 |
| aagttaacca ctaaaaaaac ggagctgtca tgtaacacgc ggatcgagca ggtcacagtc | 540 |
| atgaagccat caaagcaaaa gaactaatcc aagggctgag atgattaatt agtttaaaaa | 600 |
| ttagttaaca cgagggaaaa ggctgtctga cagccaggtc acgttatctt tacctgtggt | 660 |
| cgaaatgatt cgtgtctgtc gatttttaatt attttttttga aaggccgaaa ataaagttgt | 720 |
| aagagataaa cccgcctata taaattcata tattttcctc tccgctttga attgtctcgt | 780 |
| tgtcctcctc actttcatca gccgttttga atctccggcg acttgacaga gaagaacaag | 840 |
| gaagaagact aagagagaaa gtaagagata tccaggaga ttcattctcc gttttgaatc | 900 |
| ttcctcaatc tcatcttctt ccgctctttc tttccaaggt aataggaact ttctggatct | 960 |
| actttatttg ctggatctcg atcttgtttt ctcaatttcc ttgagatctg gaattcgttt | 1020 |
| aatttggatc tgtgaacctc cactaaatct tttggtttta ctagaatcga tctaagttga | 1080 |
| ccgatcagtt agctcgatta tagctaccag aatttggctt gaccttgatg gagagatcca | 1140 |
| tgttcatgtt acctgggaaa tgatttgtat atgtgaattg aaatctgaac tgttgaagtt | 1200 |
| agattgaatc tgaacactgt caatgttaga ttgaatctga acactgttta aggttagatg | 1260 |
| aagtttgtgt atagattctt cgaaacttta ggatttgtag tgtcgtacgt tgaacagaaa | 1320 |
| gctatttctg attcaatcag ggtttatttg actgtattga actctttttg tgtgtttgca | 1380 |
| gctcataaac catggcaatc ccggacgtat cacaggcgct ggcctggctg gaaaaacatc | 1440 |

-continued

```
ctcaggcgtt aaaggggata cagcgtgggc tggagcgcga aactttgcgt gttaatgctg      1500
atggcacact ggcaacaaca ggtcatcctg aagcattagg ttccgcactg acgcacaaat      1560
ggattactac cgattttgcg gaagcattgc tggaattcat tacaccagtg gatggtgata      1620
ttgaacatat gctgaccttt atgcgcgatc tgcatcgtta tacggcgcgc aatatgggcg      1680
atgagcggat gttgccgtta agtatgccat gctacatcgc agaaggtcag gacatcgaac      1740
tggcacagta cggcacttct aacaccggac gctttaaaac gctgtatcgt gaagggctga      1800
aaaatcgcta cggcgcgctg atgcaaacca tttccggcgt gcactacaat ttctctttgc      1860
caatggcatt ctggcaagcg aagtgcggtg atatctcggg cgctgatgcc aaagagaaaa      1920
tttctgcggg ctatttccgc gttatccgca attactatcg tttcggttgg gtcattcctt      1980
atctgtttgg tgcatctccg gcgatttgtt cttctttcct gcaaggaaaa ccaacgtcgc      2040
tgccgtttga gaaaccgag tgcggtatgt attacctgcc gtatgcgacc tctcttcgtt      2100
tgagcgatct cggctatacc aataaatcgc aaagcaatct tggtattacc ttcaacgatc      2160
tttacgaata cgtagcgggc cttaaacagg caatcaaaac gccatcggaa gagtacgcga      2220
agattggtat tgagaaagac ggtaagaggc tgcaaatcaa cagcaacgtg ttgcagattg      2280
aaaacgaact gtacgcgccg attcgtccaa aacgcgttac ccgcagcggc gagtcgcctt      2340
ctgatgcgct gttacgtggc ggcattgaat atattgaagt gcgttcgctg gacatcaacc      2400
cgttctcgcc gattggtgta gatgaacagc aggtgcgatt cctcgacctg tttatggtct      2460
ggtgtgcgct ggctgatgca ccggaaatga gcagtagcga acttgcctgt acacgcgtta      2520
actggaaccg ggtgatcctc gaaggtcgca aaccgggtct gacgctgggt atcggctgcg      2580
aaaccgcaca gttcccgtta ccgcaggtgg gtaaagatct gttccgcgat ctgaaacgcg      2640
tcgcgcaaac gctggatagt attaacggcg gcgaagcgta tcagaaagtg tgtgatgaac      2700
tggttgcctg cttcgataat cccgatctga ctttctctgc ccgtatctta aggtctatga      2760
ttgatactgg tattggcgga acaggcaaag catttgcaga agcctaccgt aatctgctgc      2820
gtgaagagcc gctggaaatt ctgcgcgaag aggattttgt agccgagcgc gagggcttcg      2880
aacgccgtca gcaggaaatg gaagccgctg ataccgaacc gtttgcggtg tggctggaaa      2940
aacacgcctg aggatcctct agactcggag gctctcaaga tcaaaggctt aaaaagctgg      3000
ggttttatga atgggatcaa agtttctttt tttcttttat atttgcttct ccatttgttt      3060
gtttcatttc cctttttgtt ttcgtttcta tgatgcactt gtgtgtgaca aactctctgg      3120 gttttttactt acgtctgcgt ttcaaaaaaa aaaccgcctt tcgttttgcg ttttagtccc      3180
attgttttgt agctctgagt gatcgaattg atgcctcttt attccttttg ttccctataa      3240
tttctttcaa aactcagaag aaaaaccttg aaactctttg caatgttaat ataagtattg      3300
tataagattt ttattgattt ggttattagt cttacttttg ctacctccat cttcacttgg      3360
aactgatatt ctgaatagtt aaagcgttac atgtcttcca ttcacaaatg aacttaaact      3420
agcacaaagt cagatatttt aagagaattc                                      3450
```

<210> SEQ ID NO 18
<211> LENGTH: 2857
<212> TYPE: DNA
<213> ORGANISM: Artificial Sequence
<220> FEATURE:
<223> OTHER INFORMATION: Description of Artificial Sequence: Plasmid
      pGSACT2

<400> SEQUENCE: 18

```
aagcttgcat gctgatctca aatacattga tacatatctc atctagatct aggttatcat      60
tatgtaagaa agttttgacg aatatggcac gacaaaatgg ctagactcga tgtaattggt     120
atctcaactc aacattatac ttataccaaa cattagttag acaaaattta aacaactatt     180
ttttatgtat gcaagagtca gcatatgtat aattgattca gaatcgtttt gacgagttcg     240
gatgtagtag tagccattat ttaatgtaca tactaatcgt gaatagtgaa tatgatgaaa     300
cattgtatct tattgtataa atatccataa acacatcatg aaagacactt tctttcacgg     360
tctgaattaa ttatgataca attctaatag aaaacgaatt aaattacgtt gaattgtatg     420
aaatctaatt gaacaagcca accacgacga cgactaacgt tgcctggatt gactcggttt     480
aagttaacca ctaaaaaaac ggagctgtca tgtaacacgc ggatcgagca ggtcacagtc     540
atgaagccat caaagcaaaa gaactaatcc aagggctgag atgattaatt agtttaaaaa     600
ttagttaaca cgagggaaaa ggctgtctga cagccaggtc acgttatctt tacctgtggt     660
cgaaatgatt cgtgtctgtc gattttaatt attttttga aaggccgaaa ataaagttgt      720
aagagataaa cccgcctata taaattcata tattttcctc tccgctttga attgtctcgt     780
tgtcctcctc actttcatca gccgttttga atctccggcg acttgacaga gaagaacaag     840
gaagaagact aagagagaaa gtaagagata atccaggaga ttcattctcc gttttgaatc     900
ttcctcaatc tcatcttctt ccgctctttc tttccaaggt aataggaact ttctggatct     960
actttatttg ctggatctcg atcttgtttt ctcaatttcc ttgagatctg gaattcgttt    1020
aatttggatc tgtgaacctc cactaaatct tttggtttta ctagaatcga tctaagttga    1080
ccgatcagtt agctcgatta tagctaccag aatttggctt gaccttgatg gagagatcca    1140
tgttcatgtt acctgggaaa tgatttgtat atgtgaattg aaatctgaac tgttgaagtt    1200
agattgaatc tgaacactgt caatgttaga ttgaatctga acactgttta aggttagatg    1260
aagtttgtgt atagattctt cgaaacttta ggatttgtag tgtcgtacgt tgaacagaaa    1320
gctatttctg attcaatcag ggtttatttg actgtattga actcttttg tgtgtttgca     1380 gctcataaac catggcaatc aagctcggca tcgtgatgga ccccatcgca acatcaaca     1440 tcaagaaaga ttccagtttt gctatgttgc tggaagcaca gcgtcgtggt tacaacttca    1500
ctatatggag atgggcgatc tgtatctgat caatggtgaa gcccgcgccc atcccgcacg    1560
ctgaacgtga agcagaacta cgaagagtgg ttttcgttcg tcggtgaaca gatctgccgc    1620
tggccgatct cgatgtgatc ctgatgcgta agacccgcc gtttgatacc agtttatcta     1680
cgcgacctat attctggaac gtgccgaaga gaaagggacg ctgatcgtta caagccgcag    1740
agcctgcgcg actgtaacga gaaactgttt accgcctggt tctctgacta acgccagaaa    1800
cgctggttac gcgcaataaa gcgcagctaa aagcgttctg ggagaaaaca gcgacatcat    1860
tcttaagccg ctggacggta tgggcggcgc gtcgattttc cgcgtgaaga aggcgatcca    1920
aacctcggcg tgattgccga acccctgact gagcatggca ctcgcactgc atggcgcaaa    1980
attacctgcc agccattaaa gatggcgaca acgcgtgct ggtgtggatg gcgagccggt     2040
accgtactgc ctggcgcgta ttccgcaggg gggcgaaacc cgtgcaatct ggctgccggt    2100
ggtcgcggtg aacctcgtcc gctgacggaa agtgactgga atcgcccgt cagatcgggc     2160 cgacgctgaa agaaaagggg ctgatttttg ttggtctgga ttcatcggcg accgtctgac    2220
tgaaattaac gtcaccagcc caacctgtat tcgtgagatt aagcagagtt ccggtgtcg     2280 atcaccggaa tgttaatgga tgccatcgaa gcacgtttaa gcagcagtaa cccaccttag    2340
cgagaaggat ctcgttgagg atcctctaga ctcggaggct ctcaagatca aaggcttaaa    2400
```

```
aagctggggt tttatgaatg ggatcaaagt ttctttttt cttttatatt tgcttctcca    2460
tttgtttgtt tcatttccct ttttgttttc gtttctatga tgcacttgtg tgtgacaaac    2520
tctctgggtt tttacttacg tctgcgtttc aaaaaaaaaa accgctttcg ttttgcgttt    2580
tagtcccatt gttttgtagc tctgagtgat cgaattgatg cctctttatt cctttgttc     2640 cctataattt ctttcaaaac tcagaagaaa aaccttgaaa ctctttgcaa tgttaatata    2700
agtattgtat aagatttta ttgatttggt tattagtctt acttttgcta cctccatctt     2760
cacttggaac tgatattctg aatagttaaa gcgttacatg tcttccattc acaaatgaac    2820
ttaaactagc acaaagtcag atattttaag agaattc                              2857
```